US012065490B2

(12) United States Patent
Cooper et al.

(10) Patent No.: US 12,065,490 B2
(45) **Date of Patent: *Aug. 20, 2024**

(54) CHIMERIC ANTIGEN RECEPTORS AND METHODS OF MAKING

(71) Applicant: BOARD OF REGENTS, THE UNIVERSITY OF TEXAS SYSTEM, Austin, TX (US)

(72) Inventors: Laurence J. N. Cooper, Houston, TX (US); Ana Beatriz Korngold, Houston, TX (US); Brian A. Rabinovich, Houston, TX (US); Harjeet Singh, Houston, TX (US); Simon Olivares, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 763 days.

This patent is subject to a terminal disclaimer.

(21) Appl. No.: 17/187,074

(22) Filed: Feb. 26, 2021

(65) Prior Publication Data

US 2021/0324071 A1 Oct. 21, 2021

Related U.S. Application Data

(63) Continuation of application No. 16/145,790, filed on Sep. 28, 2018, now abandoned, which is a continuation of application No. 15/118,245, filed as application No. PCT/US2015/016057 on Feb. 16, 2015, now Pat. No. 10,125,193.

(60) Provisional application No. 61/940,339, filed on Feb. 14, 2014.

(51) Int. Cl.

| | |
|---|---|
| ***C07K 14/725*** | (2006.01) |
| ***A61K 35/17*** | (2015.01) |
| ***C07K 14/47*** | (2006.01) |
| ***C07K 14/705*** | (2006.01) |
| ***C07K 16/28*** | (2006.01) |
| ***C12N 9/12*** | (2006.01) |
| ***C12N 15/85*** | (2006.01) |
| *A61K 35/12* | (2015.01) |

(52) U.S. Cl.

CPC .......... *C07K 16/2803* (2013.01); *A61K 35/17* (2013.01); *C07K 14/4746* (2013.01); *C07K 14/4748* (2013.01); *C07K 14/7051* (2013.01); *C07K 14/70517* (2013.01); *C07K 14/70521* (2013.01); *C07K 14/70578* (2013.01); *C12N 9/1241* (2013.01); *C12N 15/85* (2013.01); *C12Y 207/07* (2013.01); *A61K 2035/124* (2013.01); *C07K 2317/622* (2013.01); *C07K 2319/00* (2013.01); *C07K 2319/02* (2013.01); *C07K 2319/03* (2013.01)

(58) Field of Classification Search

CPC .......... C07K 14/7051; C07K 14/70517; C07K 14/70521

See application file for complete search history.

(56) References Cited

U.S. PATENT DOCUMENTS

| | | | |
|---|---|---|---|
| 6,489,458 B2 | 12/2002 | Hackett et al. | |
| 6,986,887 B2 | 1/2006 | Lawman et al. | |
| 7,435,596 B2 | 10/2008 | Campana et al. | |
| 7,446,179 B2 | 11/2008 | Jensen et al. | |
| 7,446,190 B2 | 11/2008 | Sadelain et al. | |
| 7,741,465 B1 | 6/2010 | Eshhar et al. | |
| 7,833,706 B2 | 11/2010 | Begovich et al. | |
| 7,888,121 B2 | 2/2011 | Urnov et al. | |
| 8,026,097 B2 | 9/2011 | Campana et al. | |
| 8,124,084 B2 | 2/2012 | Lefrancois et al. | |
| 8,173,786 B2 | 5/2012 | Weiner et al. | |
| 8,399,645 B2 | 3/2013 | Campana et al. | |
| 8,465,743 B2 | 6/2013 | Rosenberg et al. | |
| 8,507,222 B2 | 8/2013 | Wong et al. | |
| 8,906,682 B2 * | 12/2014 | June | A61K 45/06 435/372.3 |
| 8,927,518 B1 | 1/2015 | Heller et al. | |
| 8,945,868 B2 | 2/2015 | Collingwood et al. | |
| 8,956,828 B2 | 2/2015 | Bonini et al. | |
| 9,629,877 B2 | 4/2017 | Cooper et al. | |
| 9,657,105 B2 * | 5/2017 | Forman | A61P 35/00 |
| 9,708,384 B2 * | 7/2017 | Scholler | C07K 14/465 |
| 10,125,193 B2 | 11/2018 | Cooper et al. | |
| 2003/0171546 A1 | 9/2003 | Jensen | |
| 2003/0194704 A1 | 10/2003 | Penn et al. | |

(Continued)

FOREIGN PATENT DOCUMENTS

| | | |
|---|---|---|
| CA | 2874611 | 11/2013 |
| EP | 2173378 | 4/2010 |

(Continued)

OTHER PUBLICATIONS

Dotti et al. Immunol Rev (2014) 257(1): doi: 10.1111/imr.12131 (Year: 2014).*

(Continued)

*Primary Examiner* — Jessica H Roark

(74) *Attorney, Agent, or Firm* — Parker Highlander PLLC

(57) ABSTRACT

Provided are methods of generating chimeric antigen receptors (CAR). In some embodiments, library screening of CAR is performed by generating a vector encoding the CAR from random attachment of vectors from libraries of vectors encoding antigen-binding domains (e.g., scFv regions), hinge regions, and endodomains. In some embodiments, the vectors contain a transposon.

20 Claims, 43 Drawing Sheets

Specification includes a Sequence Listing.

(56) References Cited

U.S. PATENT DOCUMENTS

2004/0043401 A1 3/2004 Sadelain et al.
2004/0126363 A1 7/2004 Jensen et al.
2005/0113564 A1 5/2005 Campana et al.
2006/0286603 A1 12/2006 Kolkman et al.
2007/0032637 A1 2/2007 Yokoyama et al.
2007/0036773 A1 2/2007 Cooper et al.
2007/0066802 A1* 3/2007 Geiger ............. C07K 14/70521 435/325
2007/0283453 A1 12/2007 Cimadevilla et al.
2009/0197309 A1 8/2009 Sycheva et al.
2009/0258363 A1 10/2009 Gregory et al.
2011/0158957 A1 6/2011 Bonini et al.
2011/0236363 A1 9/2011 Chang et al.
2012/0093842 A1 4/2012 Eshhar et al.
2012/0282256 A1 11/2012 Campana et al.
2013/0101607 A1 4/2013 Kipps et al.
2013/0121960 A1 5/2013 Sadelain et al.
2013/0216509 A1 8/2013 Campana et al.
2013/0225668 A1 8/2013 Rosenberg et al.
2013/0266551 A1 10/2013 Campana et al.
2013/0280220 A1 10/2013 Ahmed et al.
2013/0288368 A1 10/2013 June et al.
2015/0024482 A1* 1/2015 Frigault ........... C07K 14/70521 536/23.53
2016/0008398 A1 1/2016 Sadelain et al.
2017/0088597 A1 3/2017 Wong et al.
2017/0151310 A1 6/2017 Felber et al.
2017/0202924 A1 7/2017 Felber et al.

FOREIGN PATENT DOCUMENTS

EP 1934353 10/2011
EP 1809321 3/2012
JP 2004-529636 9/2004
JP 2013-116891 6/2013
WO WO 2002/077029 10/2002
WO WO 2003/089618 10/2003
WO WO 2009/091826 7/2009
WO WO 2010/008564 1/2010
WO WO 2010/108127 9/2010
WO WO 2011/059836 5/2011
WO WO 2012/079000 6/2012
WO WO 2013/040557 3/2013
WO WO 2013/059593 4/2013
WO WO 2013/063419 5/2013
WO WO 2013/074916 5/2013
WO WO 2013/084147 6/2013
WO WO 2013/154760 10/2013
WO WO 2013/176915 11/2013
WO WO 2014/037807 3/2014
WO WO 2014/100385 6/2014
WO WO 2014/144622 9/2014
WO WO 2014/164554 10/2014
WO WO 2014/186469 11/2014
WO WO 2014/190273 11/2014
WO WO 2015/061694 4/2015
WO WO 2015/123642 8/2015
WO WO 2015/142675 9/2015
WO WO 2015/164594 10/2015
WO WO 2015/164740 10/2015
WO WO 2015/174928 11/2015
WO WO 2016/073629 5/2016
WO WO 2016/073755 5/2016
WO WO 2016/138091 9/2016
WO WO 2016/145146 9/2016
WO WO 2017/048902 3/2017
WO WO 2017/075147 5/2017
WO WO 2017/177063 10/2017

OTHER PUBLICATIONS

"Human leukocyte antigen", *Wikipedia*, downloaded on Jun. 3, 2016.

"Poster Abstract Book", Society for Immunotherapy of Cancer, 26$^{th}$ Annual Meeting, Nov. 2011.

Anderson et al., "Functional Characterization of the Human Interleukin-15 Receptorhain and Close Linkage of IL15RA and IL2RA Genes", *J Biol. Chem.*, 270(50):29862-29869, 1995.

Aronovich et al., "The Sleeping Beauty transposon system: a non-viral vector for gene therapy", *Hum. Mol Genet.*, 20:R14-20, 2011.

Beerli and Barbas, "Engineering polydactyl zinc-finger transcription factors", *Nature Biotechnol.*, 20:135-141, 2002.

Berger et al. 2008. Adoptive transfer of effector CD8+ T cells derived from central memory cells establishes persistent T cell memory in primates. J Clin Invest 118:294-305.

Bessard, A., V. Sole, G. Bouchaud, A. Quemener, and Y. Jacques. 2009. High antitumor activity of RLI, an interleukin-15 (IL-15)-IL-15 receptor alpha fusion protein, in metastatic melanoma and colorectal cancer. Mol Cancer Ther 8:2736-2745.

Beurdeley et al., "Compact designer TALENs for efficient genome engineering", *Nature Communications*, 4:1762 doi: 10.1038/ncomms2782, 2013.

Bhatnagar et al., "Turmor lysing genetically engineered T cless loaded with multi-modal imaging agents", *Sci Rep*, 4: 4502, 2014.

Boch et al., "Breaking the code of DNA binding specificity of TAL-type III effectors", *Science*, 326: 1509-1512, 2009.

Boissel et al., "megaTALs: a rare-cleaving nuclease architecture for therapeutic genome engineering", *Nucleic Acids Research*, 42(4): 2591-2601, 2014.

Bonas et al., "Genetic and structural characterization of the avirulence gene avrBs3 from *Xanthomonas campestris* pv. *vesicatoria", Mol Gen Genet.*, 218: 127-136, 1989.

Borrego et al., "Recognition of human histocompatibility leukocyte antigen (HLA)-E complexed with HLA class I signal sequence-derived peptides by CD94/NKG2 confers protection from natural killer cell-mediated lysis", *J Exp Med.*, 187(5): 813-8, 1998.

Braud et al., "HLA-E binds to natural killer cell receptors CD94/NKG2A, B and C", *Nature*, 391: 795-799, 1998.

Brentjens et al., "CD19-targeted T cells rapidly induce molecular remissions in adults with chemotherapy-refractory acute lymphoblastic leukemia", *Sci. Transl. Med.*, 5:177ra38, 2013.

Brentjens et al., "Safety and persistence of adoptively transferred autologous CD19-targeted T cells in patients with relapsed or chemotherapy refractory B-cell leukemias", *Blood*, 118:4817-4828, 2011.

Bukur et al., "The role of classical and non-classical HLA class I antigens in human tumors", *Seminars in Cancer Biology*, 22: 350-358, 2012.

Bullain et al., "Genetically engineered T cells to target EGFRvIII expressing glioblastoma", *Journal of Neuro-Oncology*, 94(3): 373-382, 2009 . . . .

Burkett, P. R., R. Koka, M. Chien, S. Chai, D. L. Boone, and A. Ma. 2004. Coordinate expression and trans presentation of interleukin (IL)-15Ralpha and IL-15 supports natural killer cell and memory CD8+ T cell homeostasis. J Exp Med 200:825-834.

Caruso, "CAR-modified T cells capably of distinguishing normal cells from malignant cells", *UT GBS Dissertations and Theses*, dated May 1, 2014, retrieved from digitalcommons.library.tmc.edu/cgi/viewcontent.cgi?article=1497&context=utgsbs_dissertations on Jul. 15, 2015.

Castillo and Schluns, "Regulating the Immune system via IL-15 Transpresentation", *Cytokine*, 59(3):479-490, 2012.

Cheever MA (2008) Twelve immunotherapy drugs that could cure cancers. Immunol Rev 222:357-368.

Chicaybam, Leonardo, et al. "An efficient low cost method for gene transfer to T lymphocytes." *PloS one* 8.3 (2013).

Chmielewski et al., "T cell activation by antibody-like immunorecepteros: increase in affinity of the single-chain fragment domain above threshold does not increase T cell activation against antigen-positive target cells but decrease selectivity", *Journal of Immunology*, 173(12): 7647-7653, 2004 . . . .

Choi et al., "A high throughput microelectroporation devise to introduce a chimeric antigen receptor to redirect the specificity of human T cells", *Biomed Microdevices*, 12(5): 855-63, 2010.

(56) References Cited

OTHER PUBLICATIONS

Choi et al., "Intercerebral delivery of a third generation EGFRvIII-specific chimeric antigen receptor is efficacious against human glioma", *Journal of Clinical Neuroscience*, 21(1): 189-190, 2014.
Choo and Isalan, "Advances in zinc finger engineering", *Curr Opin Struct Biol.*, 10(4): 411-6, 2000.
Cohen et al., "In vivo expression of MHC class I genes depends on the presence of a downstream barrier element", *PLoS ONE*, 4(8): e6748. Doi:10.1371/journal.pone.0006748, 2009. Figure 1.
Collin et al., "Concise review: putting a finger on stem cell biology: zinc finger nuclease-driven targeted genetic editing in human pluripotent stem cells", *Stem Cells* 19: 1021-1033, 2011.
Cooper et al., "Good T cells for bad B cells", *Blood*, 119: 2700-2702, 2012.
Cooper, "Adoptive cellular therapies utilizing gene modified lymphocytes", presentation delivered at ASCO Annual Meeting, 2010.
Cooper, "Clinical application of Sleeping Beauty system to engineer T-cell specificity", presentation delivered at European Society of Gene and Cell Therapy Annual Meeting, 2013.
Cooper, "Democratizing T-cell therapy—enabling children to receive T cells engineered to be tumor specific", presentation delivered at Children's Hospital Los Angeles, 2014.
Cooper, "Democratizing the process to engineer T-cell specificity so pediatric oncologists can both develop and implement new therapies", presentation delivered at The Pediatric Blood and Marrow Transplant Consortium (PBMTC) Educational Program, 2013.
Cooper, "Engineering good T cells for bad B cells", presentation delivered at Moores Cancer Center, 2013.
Cooper, "Engineering lymphocytes to improve immunotherapies", presentation delivered at Feigin Center, 2012.
Cooper, "Engineering T cells for human application using a new approach to gene therapy", presentation delivered at UAB Cell Therapy Symposium, 2013.
Cooper, "Engineering T cells for human application using a new approach to gene therapy", presentation delivered at St. Jude Auditorium, 2014.
Cooper, "Engineering T cells to treat pediatric malignancies", presentation delivered in Cincinnati, OH, 2013.
Cooper, "Genetically engineered receptors in adoptive cell therapies", presentation delivered at International Society for Biological Therapy of Cancer (iSBTc), 2011.
Cooper, "Good T cells for bad B cells—engineering an immune response", presentation delivered at Case Western Reserve University, 2013.
Cooper, "Good T Cells for Bad B Cells: To explore the role of genetic engineering to render T cells specific for malignant B cells", presentation delivered at Columbia University, 2007.
Cooper, "Good T cells for Bad B cells", presentation delivered at Chaim Sheba Medical Center, 2011.
Cooper, "Good T cells for Bad B cells", presentation delivered at Stanford University, 2010.
Cooper, "Good T cells for bad B cells", presentation delivered at UNC Lineberger Cancer Center, 2013.
Cooper, "Good T Cells vs. Bad B Cells", presentation delivered at The Methodist Hospital, 2009.
Cooper, "Human translation of Sleeping Beauty system and next-generation clinical trials", presentation, 2014.
Cooper, "Innovative T Cell-Targeted Therapy for Ovarian Cancer", Annual Grant Report prepared for U.S. Army Medical Research and Materiel Command Fort Detrick, Maryland, dated Oct. 2012.
Cooper, "Nonviral gene transfer to genetically modify and genetically edit clinical-grade T cells", presentation delivered at The Genome Engineering Conference: Cutting-edge Research and Applications, 2014.
Cooper, "Redirecting T-cell specificity for human applications", presentation delivered at New York University, 2014.
Cooper, "Redirecting T-cell specify using chimeric antigen receptors", presentation delivered at University of Nebraska, 2013.
Cooper, "Targeting Cancer by Cell and Gene Therapy", presentation delivered at American Society of Gene & Cell Therapy, 2014.
Cooper, "T-cell therapy for diffuse pontine glioma", *The Dana Foundation Grant Summary*, 2015.
Cooper, "The first-in-human application of Sleeping Beauty to engineer tumorspecific T cells", presentation, 2013.
Cooper, "Use of genetically modified T cells to target malignancies", presentation delivered at Center for RNA Interference and Non-coding RNAs, 2011.
Dadi, Saïda, et al. "Cancer immunosurveillance by tissue-resident innate lymphoid cells and innate-like T cells." *Cell* 164.3 (2016): 365-377.
Davies et al., "Combining CD19 redirection and alloanergization to generate tumor-specific human T cells for allogeneic cell therapy of B-cell malignancies", *Cancer Res.*, 70: 3915-3924, 2010.
Davies et al., "Flexible targeting of ErbB dimers that drive tumorigenesis by using genetically engineered T cells", *Molecular Medicine*, 18(1); 565-576, 2012.
Davila et al., "Efficacy and Toxicity Management of 19-28z CAR T Cell Therapy in B Cell Acute Lymphoblastic Leukemia", *Sci. Transl. Med.*, 6(224):224ra25, 2014.
De Oliveira et al., "A CD19/Fc fusion protein for detection of anti-CD19 chimeric antigen receptors", *Journal of Translational Medicine*, 11:23, 2013.
De Oliveira et al., "Modification of hematopoietic stem-progenitor cells with CD19-specific chimeric antigen receptors as a novel approach for cancer immunotherapy", *Hum Gene Ther.*, 24(10): 824-39, 2013.
Deniger et al. "Bispecific T-cells expressing polyclonal repertoire of endogenous gammadelta T-cell receptors and introduced CD 19-specific chimeric antigen receptor", *Mol Ther*. Mar. 2013;21(3):638-647.
Deniger et al., "Gamma Delta T Cells: Natural Tumor Killers Amplified By Chimeric Antigen Receptors", poster abstract, Society for Immunotherapy of Cancer, 27$^{th}$ Annual Meeting, 2012.
Deniger et al., "Gamma Delta T Cells: Natural Tumor Killers Amplified By Chimeric Antigen Receptors", poster, Society for Immunotherapy of Cancer, 27$^{th}$ Annual Meeting, 2012.
Deniger et al., "Specificity Of Human Gamma Delta T Cells Can Be Re-Directed To Cd19 While Avoiding Unwanted Allogeneic Responses", poster abstract, Society for Immunotherapy of Cancer, 26$^{th}$ Annual Meeting, 2011.
Deniger et al., "Specificity Of Human Gamma Delta T Cells Can Be Re-Directed To Cd19 While Avoiding Unwanted Allogeneic Responses", poster, Society for Immunotherapy of Cancer, 26$^{th}$ Annual Meeting, 2011.
Deniger, "T-Cell treatments for solid and hematological tumors", *UT GBS Dissertations and Theses*, dated Aug. 2013, retrieved from digitalcommons.library.tmc.edu/cgi/viewcontent.cgi?article=1421&context=utgsbs_dissertations on Dec. 14, 2014.
Denman, C. J., V. V. Senyukov, S. S. Somanchi, P. V. Phatarpekar, L. M. Kopp, J. L. Johnson, H. Singh, L. Hurton, S. N. Maiti, M. H. Huls, R. E. Champlin, L. J. Cooper, and D. A. Lee. 2012. Membrane-bound IL-21 promotes sustained ex vivo proliferation of human natural killer cells. PLoS One 7:e30264.
Digiusto and Cooper, "Preparing clinical grade Ag-specific T cells for adoptive immunotherapy trials", *Cytotherapy*, 9(7):613-629, 2007.
Dubois, S., J. Mariner, T. A. Waldmann, and Y. Tagaya. 2002. IL-15Ralpha recycles and presents IL-15 In trans to neighboring cells. Immunity 17:537-547.
Duong et al., "Engineering T cell function using chimeric antigen receptors identified using a DNA library approach", *PLOS One.*, 8(5): e63037, 2013.
Ehlers et al., "Alphabeta T cell receptor-positive cells and interferon-gamma, but not inducible nitric oxide synthase, are critical for granuloma necrosis in a mouse model of mycobacteria-induced pulmonary immunopathy", *The Journal of Experimental Medicine*, 194(12):1847-1859, 2001.
Epardaud, M., K. G. Elpek, M. P. Rubinstein, A. R. Yonekura, A. Bellemare-Pelletier, R. Bronson, J. A. Hamerman, A. W. Goldrath, and S. J. Turley. 2008. Interleukin-15/interleukin-15R alpha complexes promote destruction of established tumors by reviving tumor-resident CD8+ T cells. Cancer Res 68:2972-2983.

(56) References Cited

OTHER PUBLICATIONS

Ertl et al., "Considerations for the clinical application of chimeric antigen receptor T cells: observations from a recombinant DNA Advisory Committee Symposium held Jun. 15, 2010", *Cancer Res.*, 71:3175-3181, 2011.
Extended European Search Report issued in EP Application No. 14798046, dated Oct. 10, 2016.
Extended European Search Report issued in European Application No. 19200716.9, dated Apr. 29, 2020.
Fehling et al., "MHC class I expression in mice lacking the proteasome subunit LMP-7", *Science*, 265(5176): 1234-7, 1994.
Feng et al., "Scalable generation of universal platelets from human induced pluripotent stem cells", *Stem Cell Reports*, 3(5): 817-831, 2014.
Frankel et al., "Characterization of diphtheria fusion proteins targeted to the human interleukin-3 receptor", *Protein Eng.*, 13(8):575-581, 2000.
Garbi et al., "Impaired immune responses and altered peptide repertoire in tapasin-deficient mice", *Nature Immunology*, 1(3): 234-8, 2000.
Gascoignet, "Transport and secretion of truncated T cell receptor and chamin occurs in the absence of association with CD3", *The Journal of Biological Chemistry*, 265(16):9296-9301, 1990.
Geurts et al., "Structure-based prediction of insertion-site preferences of transposons into chromosomes", *Nucleic Acids Res.*, 34:2803-2811, 2006.
Gilham et al., "CAR-T cells and solid tumors: tuning T cells to challenge an inveterate foe", *Trends Mol. Med.*, 18(7):377-384, 2012.
Giron-Michel et al. "Membrane-bound and soluble IL-15/IL-15Rα complexes display differential signaling and functions on human hematopoietic progenitors." *Blood* 106.7 (2005): 2302-2310.
Grandea et al., "Impaired assembly yet normal trafficking of MHC class I molecules in Tapasin mutant mice", *Immunity*, 13: 231-222, 2000.
Grupp et al., "Chimeric antigen receptor-modified T cells for acute lymphoid leukemia", *The New England Journal of Medicine*, 368(16): 1509-18, 2013.
Guerrero et al., "Th human application of gene therapy to re-program T-cell specificity using chimeric antigen receptors", *Chin J Cancer*, 33(9): 421-433, 2014.
Guo, Y., Luan, L., Rabacal, W., Bohannon, J.K., Fensterheim, B.A., Hernandez, A. and Sherwood, E.R., 2015. IL-15 superagonist-mediated immunotoxicity: role of NK cells and IFN-γ. *The Journal of Immunology*, 195(5), pp. 2353-2364.
Gupta et al., "Development of an EGFRvIII specific recombinant antibody", *BMC Biotechnology*, 10(1): 72, 2010.
Guschin et al., "A rapid and general assay for monitoring endogenous gene modification", in *Engineered Zinc Finger Proteins*, eds. Mackay and Segal, Ch. 15, pp. 247-256, 2010.
Hackett et al. "A transposon and transposase system for human application." *Molecular therapy* 18.4 (2010): 674-683.
Hackett et al., "Efficacy and safety of Sleeping Beauty transposon-mediated gene transfer in preclinical animal studies", *Curr. Gene Ther.*, 11:341-349, 2011.
Hackett et al., "Evaluating risks of insertional mutagenesis by DNA transposons in gene therapy", *Transl. Res.*, 161(4):265-283, 2013.
Haft et al., "A guild of 45 CRISPR-Associated (Cas) protein families and multiple CRISPR/Cas subtypes exist in prokaryotic genomes", *PLoS Comput Biol.*, 1(6): e60, 2005.
Han et al., "IL-15: IL-15 receptor alpha superagonist complex: high-level co-expression in recombinant mammalian cells, purification and characterization." Cytokine 56.3 (2011): 804-810.
Heuer et al., "Repeat domain diversity of avrBs3-like genes in *Ralstonia solanacearum* strains and association with host preferences in the field", *Appl. Environ. Microbiol.*, 73(13): 4379-4384, 2007.
Hockemeyer et al., "A drug-inducible system for direct reprogramming of human somatic cells to pluripotency", *Cell Stem Cell*, 3: 346-353, 2008.
Holmes et al., "Disruption of HLA expression to enable allogeneic cells to escape immune recognition", *Human Gene Therapy*, 22(10): Or 15, 2011.
Hoyos V, et al. (2010) Engineering CD19-specific T lymphocytes with interleukin-15 and a suicide gene to enhance their anti-lymphoma/leukemia effects and safety. Leukemia 24(6):1160-1170.
Hsu C, Hughes MS, Zheng Z, Bray RB, Rosenberg SA, and Morgan RA. 2005. Primary human T lymphocytes engineered with a codon-optimized IL-15 gene resist cytokine withdrawal-induced apoptosis and persist long-term in the absence of exogenous cytokine. J Immunol 175(11):7226-34.
Huang et al., "Genetically modified T cells targeting interleukin-11 receptor alpha-chain kill human osteosarcoma cells and induce the regression of established osteosarcoma lung metastases", *Cancer Res.*, 72:271-281, 2012.
Huang, Xin, et al. "Sleeping Beauty Transposon-mediated Engineering of Human Primary T Cells for Therapy of CD19+ Lymphoid Malignancies." *Molecular Therapy* 16.3 (2008): 580-589.
Huls et al., "Clinical application of sleeping beauty and artificial antigen presenting cells to genetically modify T cells from peripheral and umbilical cord blood", *Journal of Visualized Experiments*, 72: e50070, 2013.
Hunter MR, et al. (2013) Chimeric gammac cytokine receptors confer cytokine independent engraftment of human T lymphocytes. Mol Immunol 56(1-2):1-11.
Huntington, N. D., N. Legrand, N. L. Alves, B. Jaron, K. Weijer, A. Plet, E. Corcuff, E. Mortier, Y. Jacques, H. Spits, and J. P. Di Santo. 2009. IL-15 trans-presentation promotes human NK cell development and differentiation in vivo. J Exp Med 206:25-34.
Hurton et al., "Expression of IL-7 and IL-15 as membrane-bound molecules on tumor-specific T cells for enhanced costimulation", poster, International Pediatric Oncology, 2010.
Hurton et al., "Expression of IL-7 and IL-15 as Membrane-bound Molecules on Tumor-specific T Cells for Enhanced Costimulation", abstract, CPRIT, 2010.
Hurton et al., "Expression of IL-7 and IL-15 as Membrane-bound Molecules on Tumor-specific T Cells for Enhanced Costimulation", poster, CPRIT, 2010.
Hurton et al., "Improved costimulation of CD19-specific T cells transpresenting a membrane-bound IL-15", presentation delivered at American Society of Gene & Cell Therapy, 2011.
Hurton et al., "Improved in vivo persistence of CD19-specific T cells expressing a membrane-bound form of IL-15", poster, Children's Cancer Hospital, The University of Texas M.D. Anderson Cancer Center, Houston, TX, 2012.
Hurton et al., "Improved in vivo persistence of CD19-specific T cells expressing a membrane-bound form of IL-15", presentation delivered at Children's Cancer Hospital, The University of Texas M.D. Anderson Cancer Center, Houston, TX, 2012.
Hurton et al., "Improved in vivo persistence of CD19-specific T cells expressing a membrane-bound form of IL-15", poster, Society for Immunotherapy of Cancer, 26th Annual Meeting, 2011.
Hurton et al., "Improved in vivo persistence of CD19-specific T cells expressing a membrane-bound form of IL-15", slides, Society for Immunotherapy of Cancer, 26th Annual Meeting, 2011.
Hurton et al., "Tethered IL-15 mutein on CD19-specific T cells sustains persistence when tumor antigen is low and can treat minimal residual disease", poster, American Society of Gene & Cell Therapy, 2013.
Hurton et al., "Tethered IL-15: Persistence, Memory, & Efficacy in Adoptive Cell Therapy", presentation delivered at Baylor, 2013.
Hurton, "Tethered IL-15 to augment the therapeutic potential of T cells expressing chimeric antigen receptor: Maintaining memory potential, persistence, and antitumor activity", dissertation defense flyer, 2013.
Hurton, "Tethered IL-15 to augment the therapeutic potential of T cells expressing chimeric antigen receptor: Maintaining memory potential, persistence, and antitumor activity", dissertation defense slides, 2013.
Hurton, "Tethered il-15 to augment the therapeutic potential of t cells expressing chimeric antigen receptor: maintaining memory potential, persistence, and antitumor activity," Thesis, Mar. 2014.

(56) References Cited

OTHER PUBLICATIONS

Hurton, Lenka V., et al. "Improved costimulation of CD19-specific T cells transpresenting a membrane-bound IL-15." *Molecular Therapy*. vol. 19., S138, 2011.
Hurton, Lenka V., et al. "Tethered IL-15 mutein on CD19-specific T cells sustains persistence when tumor antigen is low and can treat minimal residual disease." *Molecular Therapy*. vol. 21., S237, 2013.
Imamura M, et al. (2014) Autonomous growth and increased cytotoxicity of natural killer cells expressing membrane-bound interleukin-15. Blood 124(7):1081-1088.
Isalan et al., "A rapid, generally applicable method to engineer zinc fingers illustrated by targeting the HIV-1 promoter", *Nat Biotechnol.*, 19(7): 656-660, 2001.
Ivics et al., "Molecular reconstruction of Sleeping Beauty, a Tc1-like transposon from fish, and its transposition in human cells", *Cell*, 91:501-510, 1997.
Izsvak and Ivics, "Sleeping beauty transposition: biology and applications for molecular therapy", *Mol. Ther.*, 9:147-156, 2004.
Izsvak et al., "Translating Sleeping Beauty transposition into cellular therapies: victories and challenges", *Bioessays*, 32:756-767, 2010.
Jamieson et al., "Drug discovery with engineered zinc-finger proteins", *Nature Reviews Drug Discovery*, 2(5): 361-368, 2003.
Jansen et al., "Identification of genes that are associated with DNA repeats in prokaryotes", *Molecular Microbiology*, 43(6): 1565-1575, 2002.
Jaramillo et al., "Abstract 1778: nimotuzumab, ahumanized antiepidermal growth factor receptor antibody, interacts with EGFRvIII", *Cancer Res.*, dated Apr. 15, 2010.
Jena et al., "Chimeric antigen receptor (CAR)-specific monoclonal antibody to detect CD19-specific T cells in clinical trials", PLoS One, 8(3): e57838, 2013.
Jena et al., "Redirecting T-cell specificity by introducing a tumor-specific chimeric antigen receptor", *Blood*, 116:1035-1044, 2010.
Jena et al., "Specifically targeting the interface between HER1-HER3 heterodimer on breast cancer to limit off-target effects using chimeric antigen receptor designs with improved T-cell energy balance", *Blood*, 124(21): 2151, 2014.
Jensen and Riddell, "Design and implementation of adoptive therapy with chimeric antigen receptor-modified T cells." *Immunological reviews* 257.1 (2014): 127-144.
Jin et al., "The hyperactive Sleeping Beauty transposase SB100X improves the genetic modification of T cells to express a chimeric antigen receptor", *Gene Ther.*, 18:849-856, 2011.
Jones et al., "Lentiviral vector design for optimal T cell receptor gene expression in the transduction of peripheral blood lymphocytes and tumor-infiltrating lymphocytes", *Human Gene Ther.*, 20(6):630-640, 2009.
Jutten et al., "Binding of cetuximab to the EGFRvIII deletion mutant and its biological consequences in malignant glioma cells", *Radiotherapy and Oncology*, 92(3): 393-398, 2009 . . . .
Kageshita et al., "Down-regulation of HLA class I antigen-processing molecules in malignant melanoma", *American Journal of Pathology*, 154(3): 745-754, 1999.
Kalos et al., "T cells with chimeric antigen receptors have potent antitumor effects and can establish memory in patients with advanced leukemia", *Sci Transl Med.*, 3: 95ra73, 2011.
Kay et al., "A bacterial effector acts as a plant transcription factor and induces a cell size regulator", *Science*, 318(5850): 648-51, 2007. Supporting Material.
Kebriaei et al., "Chimeric antibody receptors (CARs): driving T-cell specificity to enhance anti-tumor immunity", *Frontiers in Bioscience*, 4: 520-531, 2014.
Kebriaei et al., "First clinical trials employing Sleeping Beauty gene transfer system and artificial antigen presenting cells to generate and infuse T cells expressing CD19-specific chimeric antigen receptor", presentation delivered at American Society of Hematology, 2013.
Kebriaei et al., "Infusing CD19-directed T cells to augment disease control in patients undergoing autologous hematopoietic stem-cell transplantation for advanced B-lymphoid malignancies", *Hum. Gene Ther.*, 23:444-450, 2012.
Kermer V, Baum V, Hornig N, Kontermann RE, & Muller D (2012) An antibody fusion protein for cancer immunotherapy mimicking IL-15 trans-presentation at the tumor site. Mol Cancer Ther 11(6):1279-1288.
Klebanoff CA, et al. (2004) IL-15 enhances the in vivo antitumor activity of tumor-reactive CD8+ T cells. Proc Natl Acad Sci U S A 101(7): 1969-1974.
Kobayashi, H., S. Dubois, N. Sato, H. Sabzevari, Y. Sakai, T. A. Waldmann, and Y. Tagaya 2005. Role of trans-cellular IL-15 presentation in the activation of NK cellmediated killing, which leads to enhanced tumor immunosurveillance. Blood 105:721-727.
Kochenderfer and Rosenberg, "Treating 8-cell cancer with T cells expressing anti-CD19 chimeric antigen receptors", *Nat. Rev.*, 10:267-276, 2013.
Kochenderfer et al., "B-cell depletion and remissions of malignancy along with cytokine-associated toxicity in a clinical trial of anti-CD19 chimeric-antigen-receptor-transduced T cells", *Blood*, 119:2709-2720, 2012.
Kochenderfer et al., "Eradication of B-lineage cells and regression of lymphoma in a patient treated with autologous T cells genetically engineered to recognize CD19", *Blood*, 116:4099-4102, 2010.
Kohn et al., "CARs on track in the clinic", *Mol. Ther.*, 19:432-438, 2011.
Korngold, Ana Beatriz, et al. "Designing chimeric antigen receptors for personalized immunotherapy: Rapid assembly of CARs from principal components using "EZ-CAR" platform." *Cancer Immunology Research*. vol. 4. No. 1., 2016.
Korzh, "Searching for tissue-specific regulatory elements by Tol2 transposon as an example of evolutionary genomics and development biology", *Ontogenesis*, 39(2):94-99, 2008.
Kowolik, Claudia M., et al. "CD28 costimulation provided through a CD 19-specific chimeric antigen receptor enhances in vivo persistence and antitumor efficacy of adoptively transferred T cells." *Cancer research* 66.22 (2006): 10995-11004.
Krishnamurthy et al., "Targeting an ancient retrovirus express in melanoma using adoptive T-cell therapy", *Oral presentation of Immunology Graduate Program, The University of Texas Graduate School of Biomedical Sciences*, dated Feb. 24, 2012.
Krishnamurthy, J. et al., "84. T-cell targeting an ancient retrovirus expressed in melanoma cells", *Molecular Therapy*, 20, Supplement 1, pp. Abstract 84, May 2012.
L'Haridon et al., "Transcriptional regulation of the MHC class I HLA-AII promoter by the zinc finger protein ZFX", *Nucleic Acids Research*, 24(10): 1928-1935, 1996.
Leibundgut-Landmann et al., "Specificity and expression of CIITA, the master regulator of MHC class II genes", *Eur. J. Immunol.*, 34: 1513-1525, 2004.
Likar et al., "Using mutated variant of human deoxycytidine kinase as a reporter gene for assessing adoptive T-cell therapy", *Voprosy gematologii, onkologii I immunopatologii v pediatrii*, (Questions of hematology, oncology and immunopathology in pediatrics), 11(2):23-31, 2012.
Lipowska-Bhalla, Grazyna, et al. "Targeted immunotherapy of cancer with CAR T cells: achievements and challenges." *Cancer Immunology, Immunotherapy* 61.7 (2012): 953-962.
Lorimer et al., "Recombinant immunotoxins specific for a mutant epidermal growth factor receptor: targeting with a single chain antibody variable domain isolated by phage display", *Proceeding of the National Academy of Sciences U.S.A.*, 93: 14815-14820, 1996.
Maier et al., "High-resulution HLA alleles and haplotypes in the United States population", *Human Immunology*, 68: 779-788, 2007.
Maiti et al., "Sleeping beauty system to redirect T cell specific for human applications", *J Immunother.*, 36(2): 112-23, 2013.
Makarova et al., "A Dna repair system specific for thermophilic archaea and bacteria predicted by genomic context analysis", *Nucleic Acids Research*, 30(2): 482-496, 2002.
Makarova et al., "A putative RNA-interference-based immune system in prokaryotes: computational analysis of the predicted

(56) References Cited

OTHER PUBLICATIONS enzymatic machinery, functional analogies with eukaryotic RNAi, and hypothetical mechanisms of action", *Biology Direct*, 1:7, 2006.
Manuri et al., "piggyback transposon/transposase system to generate CD19-specific T cells for the treatment of B-lineage malignancies", *Human Gene Therapy*, 21: 427-437, 2010.
Markley JC and Sadelain M. 2010.IL-7 and IL-21 are superior to IL-2 and IL-15 in promoting human T cell-mediated rejection of systemic lymphoma in immunodeficient mice. Blood. 115(17):3508-19.
Marks-Konczalik J, et al. (2000) IL-2-induced activation-induced cell death is inhibited in IL-15 transgenic mice. Proc Natl Acad Sci U S A 97(21):11445-11450.
Mateo et al., "Humanization of a mouse monoclonal antibody that blocks the epidermal growth factor receptor: recovery of antagonistic activity", *Immunotechnology*, 3(1): 71-81, 1997.
Mates et al., "Molecular evolution of a novel hyperactive Sleeping Beauty transposase enables robust stable gene transfer in vertebrates", *Nat. Genetics*. 41(6):753-61, 2009.
Milone, Michael C., et al. "Chimeric receptors containing CD137 signal transduction domains mediate enhanced survival of T cells and increased antileukemic efficacy in vivo." *Molecular Therapy* 17.8 (2009): 1453-1464.
Mlecnik B, et al. (2014) Functional network pipeline reveals genetic determinants associated with in situ lymphocyte proliferation and survival of cancer patients. Sci Transl Med 6(228):228ra237.
Mortier E, et al. (2006) Soluble interleukin-15 receptor alpha (IL-15R alpha)-sushi as a selective and potent agonist of IL-15 action through IL-15R beta/gamma. Hyperagonist IL-15 x IL-15R alpha fusion proteins. J Biol Chem 281(3):1612-1619.
Moscou and Bogdanove, "A simple cipher governs DNA recognition by TAL effectors", *Science*, 326: 1501, 2009.
Motmans et al., "Enhancing the tumor-specificity of human T cells by the expression of chimeric immunoglobulin/T cell receptor genes", *Immunotechnology* 2(4): 303-304, 1995.
Nakagawa et al., "Development of next-generation adoptive immunotherapy using cytoxic T-lymphocyte (CTL) expressing chimeric antigen receptor (CAR)", *Drug Delivery System*, 2013, vol. 28, No. 1, p. 35-44. English Abstract.
Nakazawa et al., "Optimization of the piggyback transposon system for the sustained genetic modification of human T lymphocytes", *Journal of Immunotherapy*, 32(8): 826-836, 2009.
NCBI, Genbank accession No. AAT73716.1, dated Oct. 20, 2004.
NCBI, Genbank accession No. AAU14166.1, dated Mar. 16, 2005.
NCBI, Genbank accession No. ACC78293.1, dated Apr. 29, 2008.
NCBI, Genbank accession No. CAD61786.1, dated Jan. 24, 2003.
NCBI, Genbank accession No. CBK46760.1, dated May 13, 2010.
NCBI, NCBI reference sequence No. NP_002180.1, dated Apr. 21, 2013.
NCBI, PDB accession No. 1UZ6_F, dated Oct. 18, 2012.
O'Conner et al., "Adoptive T-cell therapy improves treatment of canine non-Hodgkin lymphoma post chemotherapy", *Sci Rep.*, 2: 249, 2012.
Office Communication issued in Australian Application No. 2014265487, dated Oct. 16, 2019.
Office Communication issued in Canadian Application No. 2,911,961, dated Mar. 17, 2020.
Office Communication issued in Chinese Application No. 201480039592.6, dated Dec. 9, 2019.
Office Communication issued in Indian Application No. 10638/DELNP/2015, dated Mar. 18, 2020.
Office Communication issued in U.S. Appl. No. 14/890,977, dated Jul. 5, 2016.
Office Communication issued in U.S. Appl. No. 15/434,595, dated Jan. 11, 2018.
Office Communication issued in U.S. Appl. No. 15/434,595, dated Mar. 7, 2019.
Official Communication issued in corresponding Russian Application No. 2016136370, mailed on Oct. 9, 2020.
Olsen, S. K., N. Ota, S. Kishishita, M. Kukimoto-Niino, K. Murayama, H. Uchiyama, M. Toyama, T. Terada, M. Shirouzu, O. Kanagawa, and S. Yokoyama. 2007. Crystal Structure of the interleukin-15. interleukin-15 receptor alpha complex: insights into trans and cis presentation. J Biol Chem 282:37191-37204.
Osman et al., "Homologous Recombination", Ch. 26 in *Aspergillus: 50 years on*. Ed. Martinelli and Kinghorn, Elsevier, Amsterdam, Jan. 1994, pp. 687-732.
Pabo et al., "Design and selection of novel $Cys_2His_2$ zinc finger proteins", *Annu. Rev. Biochem.*, 70: 313-40, 2001.
Parham, "MHC class I molecules and KIRS in human history, health and survival", Nature Reviews Immunology, 5: 201-214, 2005.
PCT International Preliminary Report on Patentability issued in International Application No. PCT/US2015/016057, mailed Aug. 25, 2016.
PCT International Preliminary Report on Patentability issued in International Application No. PCT/US2012/065506, mailed May 30, 2014.
PCT International Preliminary Report on Patentability issued in International Application No. PCT/US2014/039365, mailed Nov. 24, 2015.
PCT International Preliminary Report on Patentability issued in International Application No. PCT/US2014/038005, mailed Nov. 26, 2015.
PCT International Preliminary Report on Patentability issued in International Application No. PCT/US2014/062191, mailed Apr. 26, 2016.
PCT International Search Report and Written Opinion issued in International Application No. PCT/US2015/016057, mailed Jul. 28, 2015.
PCT International Search Report and Written Opinion issued in International Application No. PCT/US2012/065506, mailed Mar. 4, 2013.
PCT International Search Report and Written Opinion issued in International Application No. PCT/US2014/039365, mailed Oct. 1, 2014.
PCT International Search Report and Written Opinion issued in International Application No. PCT/US2014/038005, mailed Feb. 13, 2015.
PCT International Search Report and Written Opinion issued in International Application No. PCT/US2014/062191, mailed Apr. 22, 2015.
PCT International Search Report and Written Opinion issued in International Application No. PCT/US2015/027511, mailed Jul. 29, 2015.
PCT International Search Report and Written Opinion issued in International Application No. PCT/US2015/027277, mailed Aug. 4, 2015.
PCT International Search Report and Written Opinion issued in International Application No. PCT/US2015/059072, mailed Jan. 25, 2016.
PCT International Search Report and Written Opinion issued in International Application No. PCT/US2015/059293, mailed May 3, 2016.
PCT Invitation to Pay Additional Fees issued in International Application No. PCT/US2016/021693, mailed May 19, 2016.
Perdreau, H., E. Mortier, G. Bouchaud, V. Sole, Y. Boublik, A. Plet, and Y. Jacques. 2010 Different dynamics of IL-15R activation following IL-15 cis- or transpresentation. Eur Cytokine Netw 21:297-307.
Porter et al., "Chimeric antigen receptor-modified T cells in chronic lymphoid leukemia", *The New England Journal of Medicine*, 365(8): 725-733, 2011.
Provasi et al., "Editing T cell specificity towards leukemia by zinc finger nucleases and lentiviral gene transfer", *Nature Medicine*, 18(5): 807-815, 2012.
Pule et al., "Virus-specific T cells engineered to coexpress tumor-specific receptors: persistence and antitumor activity in individuals with neuroblastoma", *Nat. Med.*, 14:1264-1270, 2008.
Ramos et al., "Chimeric antigen receptor (CAR)-engineered lymphocytes for cancer therapy", *Expert Opinion on Biological Therapy*,11(7): 855-873, 2011.

(56) References Cited

OTHER PUBLICATIONS

Rhode PR, et al. (2015) Comparison of the Superagonist Complex, ALT-803, to IL15 as Cancer Immunotherapeutics in Animal Models. Cancer Immunol Res.
Riolobos et al., "HLA engineering of human pluripotent stem cells", *Molecular Therapy*, 21(6): 1232-1241, 2013.
Riteau et al., "HLA-G1 co-expression boosts the HLA class I-mediated NK lysis inhibition", *International Immunology*, 13(2): 193-201, 2001.
Rouas-Freiss et al., "The $\alpha_1$ domain of HLA-G1 and HLA-G2 inhibits cytotoxicity induced by natural killer cells: is HLA-G the public ligand for natural killer cell inhibitory receptors?", *Proc. Natl. Acad. Sci. USA*, 94: 5249-5254, 1997.
Rowley et al., "Expression of IL-15RA or an IL-15/IL-15RA fusion on CD8+ T cells modifies adoptively transferred T-cell function in cis", *European Journal of Immunology*, 39(2): 491-506, 2009.
Rushworth et al., "Universal artificial antigen presenting cells to selectively propagate T cells expressing chimeric antigen receptor independently of specifity", *J Immunother*., 37(4): 204-13, 2014.
Sadelain, Michel, Renier Brentjens, and Isabelle Rivière. "The basic principles of chimeric antigen receptor design." *Cancer discovery* 3.4 (2013): 388-398.
Sandau, M. M., K. S. Schluns, L. Lefrancois, and S. C. Jameson. 2004. Cutting edge: transpresentation of IL-15 by bone marrow-derived cells necessitates expression of IL-15 and IL-15R alpha by the same cells. J Immunol 173:6537-6541.
Sato N, Patel HJ, Waldmann TA, & Tagaya Y (2007) The IL-15/IL-15Ralpha on cell surfaces enables sustained IL-15 activity and contributes to the long survival of CD8 memory T cells. Proc Natl Acad Sci U S A 104(2):588-593.
Schornack et al., "Gene-for-gene-mediated recognition of nuclear-targeted AvrBs3-like bacterial effector proteins", *Journal of Plant Physiology*, 163: 256-272, 2006.
Segal and Barbas, "Customs DNA-binding proteins come of age: polydactyl zinc-finger proteins", *Current Opinion in Biotechnology*, 12: 632-637, 2001.
Shen et al., "Chimeric antigen receptor containing ICOS signaling domain mediates specific and efficient antitumor effect of T cells against EGFRvIII expressing glioma", *Journal of Hematology and Oncology*, 6(1): 33, 2013.
Singh et al., "Combining Adoptive Cellular and Immunocytokine Therapies to Improve Treatment of B-Lineage Malignancy", *Cancer Res.*, 67(6):2872-2880, 2007.
Singh et al., "Reprogramming CD19-specific T cells with IL-21 signaling can improve adoptive immunotherapy of B-lineage malignancies", *Cancer Res.*, 71(10): 3516-3527, 2011.
C229. Singh, Harjeet, et al. "Manufacture of clinical-grade CD19-specific T cells stably expressing chimeric antigen receptor using Sleeping Beauty system and artificial antigen presenting cells." *PloS One* 8.5 (2013): e64138.
Singh, Harjeet, et al. "Redirecting specificity of T-cell populations for CD 19 using the Sleeping Beauty system." *Cancer research* 68.8 (2008): 2961-2971.
Somanchi et al., "Engineering lymph node homing of ex vivo-expanded human natural killer cells via trogocytosis of the chemokine receptor CCR7", *Blood*, 119(22): 5164-5172, 2012.
Steel, J. C., T. A. Waldmann, and J. C. Morris. 2012. Interleukin-15 biology and its therapeutic implications in cancer. Trends Pharmacol Sci 33:35-41.
Stoklasek TA, Schluns KS, & Lefrancois L (2006) Combined IL-15/IL-15Ralpha immunotherapy maximizes IL-15 activity in vivo. J Immunol 177(9):6072-6080.
Stone JD, Chervin AS, Schreiber H, and Kranz DM. 2012. Design and characterization of a protein superagonist of IL-15 fused with IL-15Ra and a high-affinity T cell receptor. Biotechnol. Prog. 28(6):1588-97.
Stonier SW, Ma LJ, Castillo EF, & Schluns KS (2008) Dendritic cells drive memory CD8 T-cell homeostasis via IL-15 transpresentation. Blood 112(12):4546-4554.
Supplemental Partial Search Report and Invitation to Pay Additional Fees issued in European Application No. 14749056.6, mailed Aug. 23, 2017.
Szattowski et al, "Lineage specific treatment of adult patients with acute lymphoblastic leukemia in first remission with anti-B4-blocked ricin or high-dose cytarabine: Cancer and Leukemia Group B Study 9311", *Cancer*, 97(6):1471-1480, 2003.
Tamada et al., "Redirecting gene-modified T cells toward various cancer types using tagged antibodies", *Clinical Cancer Research*, 12(23): 6436-6445, 2012.
Teague RM, et al. (2006) Interleukin-15 rescues tolerant CD8+ T cells for use in adoptive immunotherapy of established tumors. Nat Med 12(3):335-341.
Till et al., "Adoptive immunotherapy for indolent non-Hodgkin lymphoma and mantle cell lymphoma using genetically modified autologous CD20-specific T cells", *Blood*, 112:2261-2271, 2008.
Torikai et al., "A foundation for universal T-cell based immunotherapy: T cells engineered to express a CD19-specific chimeric-antigen-receptor and eliminate expression of endogenous TCR", *Blood*, 119(24):5697-5705, 2012.
Torikai et al., "HLA and TCR knockout by zinc finger nucleases: toward "off-the-shelf" allogeneic t-cell therapy for CD19$^+$ malignancies", *Blood* (*ASH Annual Meeting Abstracts*), 116: Abstract 3766, 2010.
Torikai et al., "Toward eliminating HLA class I expression to generate universal cells from allogeneic donors", *Blood*, 122(8): 1341-1349, 2013.
Trudeau, Devin L., Matthew A. Smith, and Frances H. Arnold. "Innovation by homologous recombination." *Current opinion in chemical biology* 17.6 (2013): 902-909.
Tumaini et al., "Simplified process for the production of anti-CD19-CAR-engineered T cells", *Cytotherapy*, 15(11):1406-1415, 2013.
Villard et al., "A functionally essential domain of RFX5 mediates activation of major histocompatibility complex class II promoters by promoting cooperative binding between RFX and NF-Y", *Molecular and Cellular Biology*, 20(10): 3364-3376, 2000.
Vincent, M., A. Bessard, D. Cochonneau, G. Teppaz, V. Sole, M. Maillasson, S. Birkle, L. Garrigue-Antar, A. Quemener, and Y. Jacques. 2013. Tumor targeting of the IL-15 superagonist RLI by an anti-GD2 antibody strongly enhances its antitumor potency. Int J Cancer 133:757-765.
Waldmann, T. A. 2006. The biology of interleukin-2 and interleukin-15: implications for cancer therapy and vaccine design. Nat Rev Immunol 6:595-601.
Wei et al., "The Sushi domain of soluble IL-15 receptor a is essential for binding IL-15 and inhibiting inflammatory and allogenic responses in vitro and in vivo", *J. Immunol*., 167:277-282, 2001.
Williams, David A. "Sleeping beauty vector system moves toward human trials in the United States." *Molecular therapy*16.9 (2008): 1515-1516.
Zakrzewski, J. L., D. Suh, J. C. Markley, O. M. Smith, C. King, G. L. Goldberg, R. Je nq, A. M. Holland, J. Grubin, J. Cabrera-Perez, R. J. Brentjens, S. X. Lu, G. Rizzuto, D. B. Sant'Angelo, I. Riviere, M. Sadelain, G. Heller, J. C. Zuniga-Pflucker, C. Lu, and M. R. van den Brink. 2008. Tumor immunotherapy across MHC barriers using allogeneic T-cell precursors. Nat Biotechnol 26:453-461.
Zhang X, Sun S, Hwang I, Tough DF, & Sprent J (1998) Potent and selective stimulation of memory-phenotype CD8+ T cells in vivo by IL-15. Immunity 8(5):591-599.
Zhao et al., "Multiple Injections of Electroporated Autologous T Cells Expressing a Chimeric Antigen Receptor Mediate Regression of Human Disseminated Tumor", *Cancer Res.*, 70:9053-9061, 2010.
Zheng et al., "Protein L: a novel reagent for the detection of chimeric antigen receptor (CAR) expression by flow cytometry", *Journal of Translational Medicine*, 10:29, 2012.
Zhu et al., "Overexpression of miR-152 leads to reduced expression of human leukocyte antigen-G and increased natural killer cell mediated cytolysis in JEG-3 cells", *Am J Obstet Gynecol*., 202(6): 592. e1-7, 2010.
Zhu, W.D. Marcus, W. Xu, H .- I. Lee, K. Han, J.O. Egan, et al., Novel human interleukin-15 agonists, J. Immunol. 183 (2009) 3598.

* cited by examiner

| CONSTRUCT | MOLECULAR WT (kDS) | |
|---|---|---|
| | EXPTD | OBSD |
| 19R-28Tm-28-z | | 71.4 |
| 19R-28Tm-28-z/FRA | 73.1 | 70.1 |
| 19r-CD8hTm-BB-z | 52.2 | 51.4 |
| 19r-CD8hTm-28-z | 52.1 | 51.9 |
| 19R-CD8Tm-BB-z | 73.3 | 73.5 |
| 19R-CD8Tm-28-z | 73.2 | 70.7 |
| 19R-BBTm-BB-z | 73.3 | 72.8 |
| 19R-28Tm-BB-z | 73.2 | 72.8 |
| 19R-28Tm-28-BB-z | 78.0 | 77.9 |

CYTOTOXICITY
19r-CD8hTm-BB-z
19r-CD8hTm-28-z
19R-CD8Tm-BB-z
19R-CD8Tm-28-z
19R-BBTm-BB-z
19R-28Tm-BB-z
19R-28Tm-28-BB-z
19R-28Tm-28-z
PERCENT-SPECIFIC LYSIS
70
60
50
40
30
20
10
0
CD19posDaudiB2m
CD19posNALM6
CD19posEL-4
CD19negEL-4
TARGETS (20:1)

CD3ζ

HOMO SAPIENS CD247 MOLECULE (CD247), TRANSCRIPT VARIANT 1, mRNA
NCBI REFERENCE SEQUENCE: NM_198053.2

```
Query   1  RVKFSRSADAPAYQQGQNQLYNELNLGRREEYDVLDKRRGRDPEMGGKP-RRKNPQEGLY  59
Sbjct      RVKFSRSADAPAYQQGQNQLYNELNLGRREEYDVLDKRRGRDPEMGGKPQRRKNPQEGLY

Query  60  NELQKDKMAEAYSEIGMKGERRRGKGHDGLYQGLSTATKDTYDALHMQALPPR  112
Sbjct      NELQKDKMAEAYSEIGMKGERRRGKGHDGLYQGLSTATKDTYDALHMQA
```

T-CELL SURFACE GLYCOPROTEIN CD3 ZETA CHAIN ISOFORM 1 PRECURSOR [HOMO SAPIENS]
NCBI REFERENCE SEQUENCE: NP_932170.1

```
Query   1  RVKFSRSADAPAYQQGQNQLYNELNLGRREEYDVLDKRRGRDPEMGGKP-RRKNPQEGLY  59
Sbjct  52  RVKFSRSADAPAYQQGQNQLYNELNLGRREEYDVLDKRRGRDPEMGGKPQRRKNPQEGLY  111

Query  60  NELQKDKMAEAYSEIGMKGERRRGKGHDGLYQGLSTATKDTYDALHMQALPPR  112
Sbjct 112  NELQKDKMAEAYSEIGMKGERRRGKGHDGLYQGLSTATKDTYDALHMQALPPR  164
```

T-CELL SURFACE GLYCOPROTEIN CD3 ZETA CHAIN ISOFORM 2 PRECURSOR [HOMO SAPIENS]
NCBI REFERENCE SEQUENCE: NP_000725.1

```
                          ITAM1                                       ITAM2
Query   1  RVKFSRSAD|APAYQQGQNQLYNELNLGRREEYDVLDKR|RGRDPEMGGK|PRRKNPQEGLYN|  60
Sbjct  52  RVKFSRSAD|APAYQQGQNQLYNELNLGRREEYDVLDKR|RGRDPEMGGK|PRRKNPQEGLYN|  111

                                       ITAM3
Query  61  |ELQKDKMAEAYSEIGM|KG|ERRRGKGHDGLYQGLSTATKDTYDALHMQ|ALPPR  112
Sbjct 112  |ELQKDKMAEAYSEIGM|KG|ERRRGKGHDGLYQGLSTATKDTYDALHMQ|ALPPR  163
```

FIG. 25

CARs

| CAR → | COOPER | |
|---|---|---|
| SPACER | CD28 | CD137 |
| Fc (230aa) | 194 | 217 |
| CD8 (47aa) | 213 | 212 |
| SHORT (12aa) | 265 | 268 |
| CD3ζ | WT | WT |

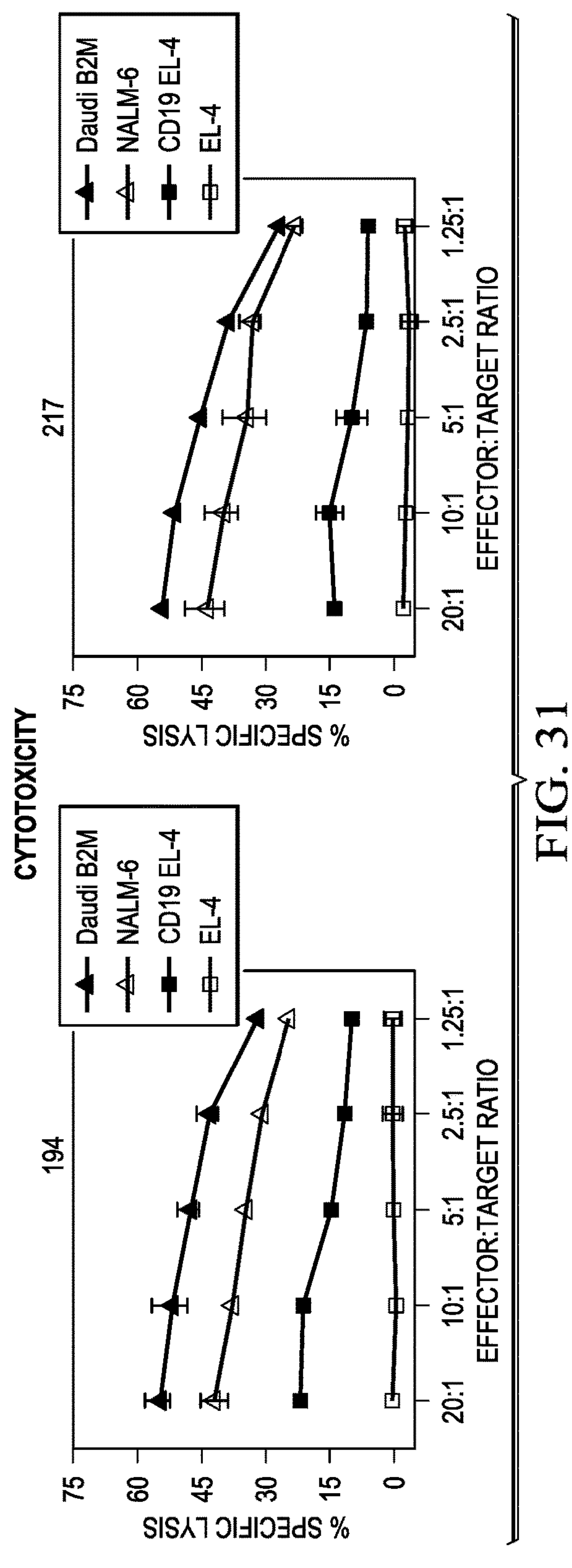
FIG. 31
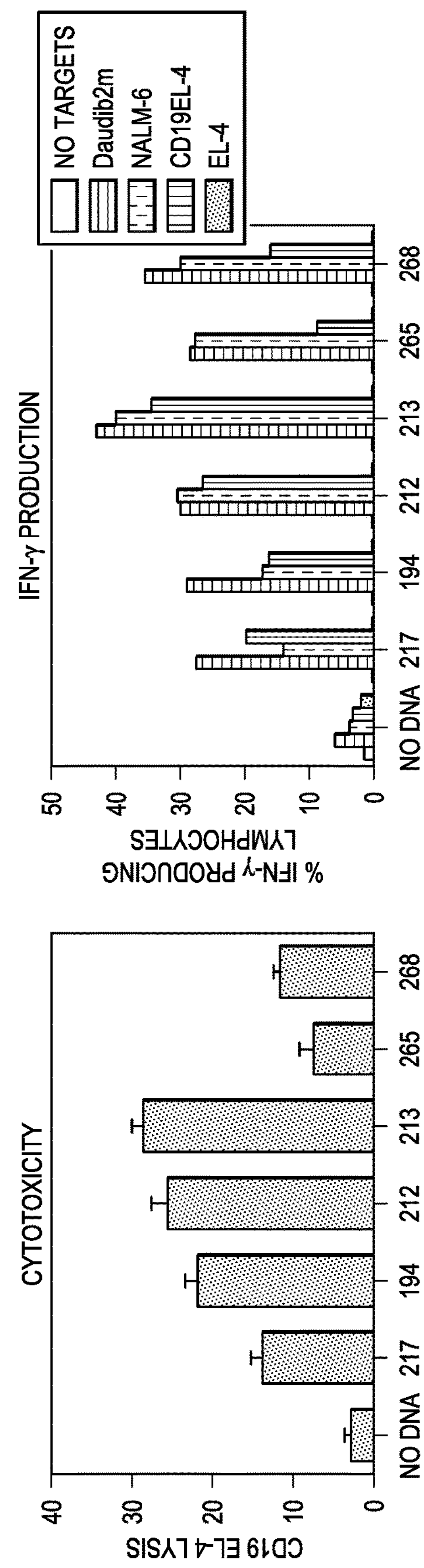
FIG. 32
FIG. 34

DONOR P491C714
DONOR GCR357861

CAR COPY NUMBER

| DOMAINS | COOPER | | | | | | |
|---|---|---|---|---|---|---|---|
| INTRACELLULAR SIGNALING | CD28 | | | CD137 | | | CD28+ CD137 |
| TM/SPACER | CD8 | CD28 | CD137 | CD8 | CD28 | CD137 | CD28 |
| Fc (230aa) | 215 (1.48) | 194 (1.12)<br>193 (1.01)<br>118 (0.98) | | 214 (1.67) | 217 (1.01, 1.14) | 216 (1.87) | 218 (0.90) |
| CD8 (47aa) | 213 (2.13, 2.6) | | | 212 (1.06, 1.7) | | | |
| SHORT (12aa) | | 265 (2.18) | | | 268 (2.53) | | |
| CD3ζ | WT | WT | WT | WT | WT | WT | WT |

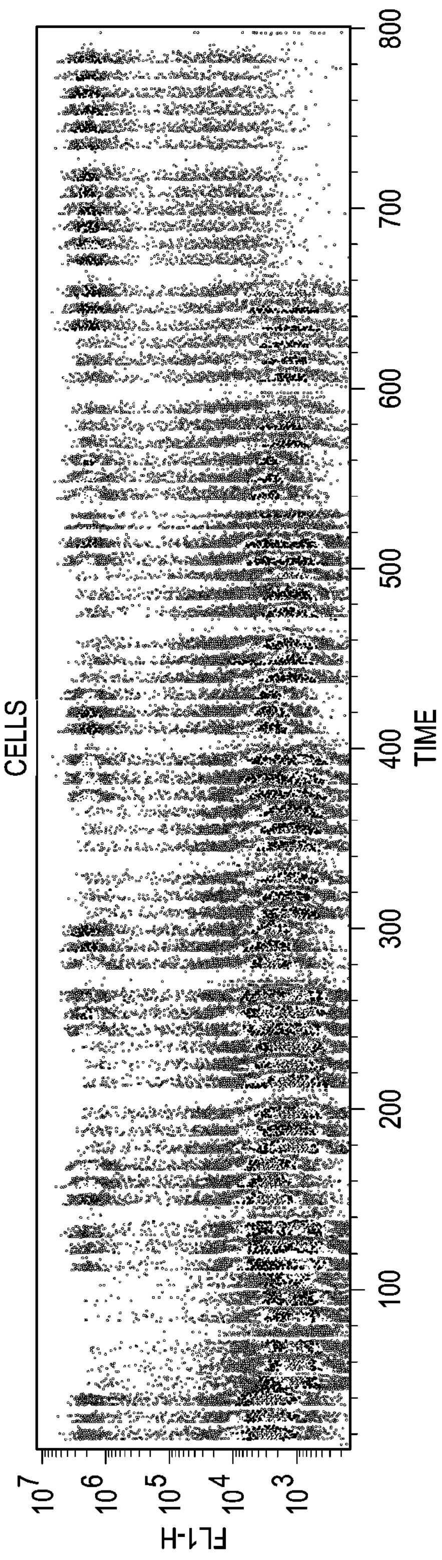
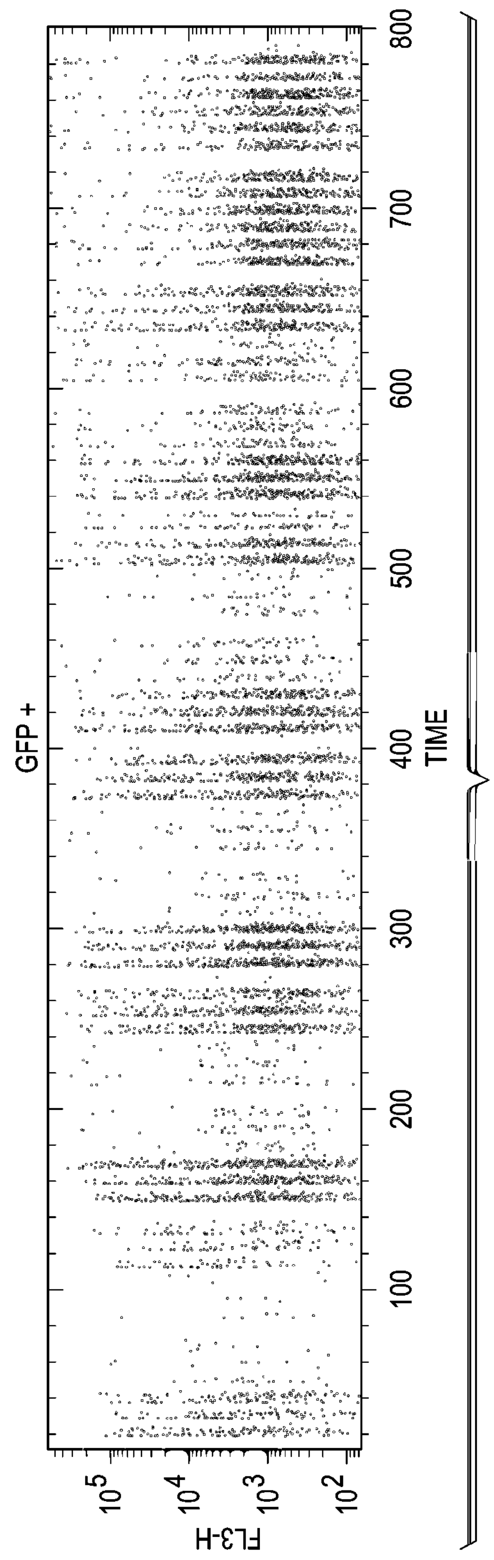
FIG. 41B

CHIMERIC ANTIGEN RECEPTORS AND METHODS OF MAKING

This application is a continuation of U.S. patent application Ser. No. 16/145,790, filed Sep. 28, 2018, which is a continuation of U.S. patent application Ser. No. 15/118,245, filed Aug. 11, 2016, as a national phase application under 35 U.S.C. § 371 of International Application No. PCT/US2015/016057, filed Feb. 16, 2015, which claims the priority benefit of U.S. Provisional Patent Application No. 61/940,339, filed Feb. 14, 2014, the entirety of each of which are incorporated herein by reference.

This invention was made with government support under grant number W81XWH-11-1-0002 awarded by the U.S. Department of the Army. The government has certain rights in the invention.

BACKGROUND OF THE INVENTION

Field of the Invention

The present invention relates generally to the field of molecular biology and medicine. More particularly, it concerns methods of generating chimeric antigen receptors (CAR).

Description of Related Art

Adoptive T cell transfer is a promising therapeutic approach that may be used for the treatment of cancer. Adoptive T cell transfer involves isolating and expanding antigen-specific T cells that can selectively kill tumor cells. Generally, T cells are removed from a subject and cultured in vitro. A Chimeric Antigen Receptor (CARs) may be introduced into a T cell in vitro to direct the T cell, once re-introduced into the subject, to selectively kill tumor cells based on expression of an antigen (e.g., Wieczorek et al. 2013; Berry et al., 2013).

One problem associated with adoptive T cell transfer is that significant variability exists between which CAR may work more effectively in certain populations of patients, e.g., for treating a specific cancer. Due to the very large number of potential different CAR that could potentially be generated that might exhibit therapeutic activity against a cancer, it is presently very difficult for clinicians anticipate which CAR may display therapeutic activity against a given cancer or subtype of cancer. Due to the significant therapeutic potential of adoptive T cell transfer, there is a clear need for improved methods for identifying and generating new CARs.

SUMMARY OF THE INVENTION

The present invention provides, in some aspects, methods for the generation of CAR, and specific CAR are provided. In some aspects, methods are provided for the generation of large number of CAR that may be screened for activity against a particular cancer or sub-type of cancer; in this way, CAR may be generated and identified that can exhibit improved therapeutic potential against a particular cancer or sub-type of cancer. CAR provided herein may be therapeutically administered to a subject or human patient, e.g., to treat a cancer.

Clinical data demonstrates that a particular chimeric antigen receptor (CAR) design targeting T cells to a given tumor-associated antigen (TAA) may have varying therapeutic potential in different patients. For example, second generation CD19-specific CARs activated via chimeric CD28/CD3zeta or CD137/CD3-zeta can exhibit superior clinical responses when autologous genetically modified T cells are administered to patients with acute, rather than chronic, B-lineage leukemia. To address this problem, provided herein are methods for generating CAR species that may exhibit an improved anti-tumor effect for a given tumor.

For example, methods are provided herein that may be used to generate and screen a large number of CAR for their ability to treat a cancer from a given patient; in this way, the methods may be used to personalize a therapy for a patient and select a particular CAR that displays an improved therapeutic potential for a particular patient or subset of patients with a particular cancer. A clinical approach to gene therapy may utilize the electro-transfer of DNA plasmids from the Sleeping Beauty (SB) transposon system, e.g., to reduce the cost and complexity to manufacture individual CAR designs for small subsets of patients. These methods for personalizing CAR+ T cells may utilize the generation a large number of CAR molecules that can be screened and assessed for their ability to benefit a given patient.

In some aspects, provided are methods for the high throughput assembly of CAR molecules using a triple site-specific recombination system (also referred to as the "EZ-CAR" Platform). In some embodiments, these methods can allow for the rapid combination of 3 components of a prototypical CAR from (i) the single chain variable fragment (scFv) that defines specificity, (ii) the scaffold/hinge that appends the scFv from the cell surface, and (iii) one or more intracellular signaling domains. For example, as shown in the below examples, a CD19-specific CAR that is activated through chimeric CD28/CD3-zeta was generated using the EZ CAR platform in parallel with clinical-grade CD19RCD28mζ CAR+ T cells (CG CAR).

In some embodiments, a CAR provided herein or generated by methods according to the present invention may be co-expressed in a T cell with a membrane bound IL-15. In this way, the T cell may survive or exist in a quiescent state without significant proliferation in vitro or in vivo. In contrast, as described previously T-cells expressing CAR will typically die when cytokines are withdrawn in vitro, and this cell death may serve as a safety feature in certain instances when the T cells are administered clinically. T cell proliferation is typically measured using a autonomous cell assay. Thus, in contrast to certain previously identified CAR, where T cells cannot persist in vitro without antigenic stimulation, CAR are provided herein which may induce cytotoxicity without autonomous growth in vitro. Depending on the particular embodiment desired, a CAR produced by methods of the present invention or provided herein may be expressed in a T cell either with or without co-expression in the T cell of a membrane bound IL-15.

An aspect of the present invention relates to a composition comprising: (a) a plurality of first vectors encoding one or more distinct antigen binding domains; (b) a plurality of second vectors encoding one or more distinct hinge domains; and (c) a plurality of third vectors encoding one or more distinct endodomains; wherein at least two of the first, second and third vectors comprise a plurality of two or more vectors encoding distinct antigen binding domains, hinge domains and/or endodomains, respectively, and further wherein the vectors comprise sites for homologous recombination to permit the generation of a fourth vector encoding a chimeric antigen receptor (CAR).

In the present invention, as used in reference to protein domains and polypeptides such as antigen binding domains, hinge domains, transmembrane domains, and endodomains, the term "distinct" means domains having, comprising, or consisting of different polypeptide (amino acid) sequences. For example, two "distinct" antigen binding domains may bind the same antigen (indeed, even the same epitope on that antigen); however, the antigen binding domains are "distinct" if their sequential amino acid compositions differ from each other. Likewise, two "distinct" antigen binding domains, differing in sequential amino acid composition, may also specifically bind different antigens and epitopes. Conversely, as used herein, two molecules (polypeptides) of identical amino acid sequence are not "distinct" polypeptides.

In some embodiments, the plurality of first vectors encodes a plurality of distinct antigen binding domains, the plurality of second vectors encodes one hinge domain, and the plurality of third vectors encodes a plurality of distinct endodomains. In some embodiments, the plurality of first vectors encodes a plurality of distinct antigen binding domains, the plurality of second vectors encodes a plurality of distinct hinge domains, and the plurality of third vectors encodes a plurality of distinct endodomains. In some embodiments, the plurality of first vectors encodes a plurality of distinct antigen binding domains, the plurality of second vectors encodes a plurality of distinct hinge domains, and the plurality of third vectors encodes a one endodomain. In some embodiments, the plurality of first vectors encodes one antigen binding domain, the plurality of second vectors encodes a plurality of distinct hinge domains, and the plurality of third vectors encodes a plurality of distinct endodomains. In some embodiments, the antigen binding domains comprise or consist of scFv. The third vectors may encode a transmembrane domain. The second vectors may encode a transmembrane domain. In some embodiments, the composition further comprises a plurality of fifth vectors encoding one or more transmembrane domain; wherein the first vectors, the second vectors, the third vectors, and the fifth vectors comprise sites for homologous recombination to generate a fourth vector encoding a chimeric antigen receptor (CAR). The first vector may comprise a first sequence and a second site of homologous recombination. The second vector may comprise the second sequence of homologous recombination and a third sequence of homologous recombination. The third vector may comprise the third sequence of homologous recombination and a fourth sequence of homologous recombination. The third vector may comprise the third sequence of homologous recombination and a fourth sequence of homologous recombination. The fourth vector comprises the first sequence of homologous recombination and the fourth sequence of homologous recombination. The first vector, the second vector, and/or the third vector may encode a transposase. The transposase may be a salmonid-type Tc1-like transposase (SB). In some embodiments, 1, 2, 3, 4, or all of the first vector, the second vector, the third vector, the fourth vector, and/or the fifth vector is a Sleeping Beauty (SB) or piggyBac transposon vector. Alternately, in some embodiments, the first vector, the second vector, the third vector, the fourth vector, and/or the fifth vector is not a Sleeping Beauty (SB) or piggyBac transposon vector; for example, in some embodiments, a CAR may be generated without using a Sleeping Beauty (SB) or piggyBac vector, and then the CAR may subsequently be inserted in a vector suitable for transfecting T cells (e.g., inserted into a Sleeping Beauty (SB) vector as described, e.g., in Singh et al., 2015). Nonetheless, in some embodiments, generating a CAR already present in a vector that is suitable for transfecting T cells may simply the process or reduce the number of steps required to both generate a CAR and transfect a T cell. The distinct antigen binding domains may selectively bind different antigens. In some embodiments, the distinct antigen binding domains selectively bind the same antigen. The antigen binding domain may selectively bind CD19, Universal Antigen (mouse), HER-3, GD2, Gp75, CS1 protein, mesothelin, phosphatidylserine, cMyc, CD22, CD4, CD44v6, CD45, CD28, CD3, CD3e, CD123, CD138, CD52, CD56, CD74, CD30, Gp75, CD38, CD33, CD20, Her1/HER3 fusion, GD2, a carbohydrate, *Aspergillus*, ROR1, c-MET, EGFR, Dectin, Ebola, a fungus, GP, HERV-K (HERVK), NY-ESO-1, VEGF-R2, TGF-b2R, IgG4, Biotin, or O-AcGD2. The distinct antigen binding domains may consist of or comprise scFv. The hinge region may consist of or comprise the 12 AA peptide (GAGAGCAAGTACGGCCCTCCCTGCCCCCCTTGCCCT; SEQ ID NO:1), t-20 AA peptide, IgG4 Fc Δ EQ, IgG4 Fc Δ Q, (t-12AA+t-20AA), mKate, phiLov, dsRed, Venus, eGFP, CH3 HA, (CD8 α+t-20AA), Double t-20 AA, (t-20AA+CD8α), (CD8α+Leucine Zipper Basep1), (CD8α+Leucine Zipper Acid1), 2D3, CD8 α, or IgG4 Fc. At least one of the endodomains may comprise CD3ζ. At least one of the endodomains may comprise one or more ITAM domains. In some embodiments, at least one of the endodomains comprise (CD28+CD3ζ), (CD28+CD27+CD3ζ), (CD28+OX40+CD3ζ), (CD28+4-1BB+CD3ζ), (CD28+CD27+OX40+CD3ζ), (CD28+4-1BB+CD27+CD3ζ), (CD28+4-1BB+OX40+CD3ζ), (4-1BB+CD3ζ), (4-1BB+OX40+CD3ζ), (4-1BB+CD27+CD3ζ), (CD27+CD3ζ), (CD27+OX 40+CD3ζ), (CD28A+CD3ζ), (CD28A+CD27+CD3ζ), (CD28A+OX40+CD3ζ), (CD28A+4-1BB+CD3ζ), (CD28A+4-1BB+OX40+CD3ζ), (CD28A+CD27+OX40+CD3ζ), (CD28A+4-1BB+CD27+CD3ζ), (4-1BB+ICOS+CD3ζ), (CD28+ICOS+CD3ζ), (ICOS+CD3ζ), CD3ζ, or CD28 only. In some embodiments, the CARs may be tested for activity, e.g., using the iQue™ Screener (IntelliCyt, Albuquerque, NM). In some embodiments CARs may evaluated for one or more characteristics (e.g., viability, upregulation of activation signals, upregulation of CD25, cytokine release, and/or cell killing) when expressed in cells such as T cells using a technique such as, e.g., flow cytometry.

Another aspect of the present invention relates to a composition comprising a collection of vectors encoding chimeric antigen receptors encoding a plurality of distinct antigen binding domains, hinge domains and endodomains, the vectors of said collection being randomized with respect to said domains.

Yet another aspect of the present invention relates to a method of producing a plurality of vectors each encoding a chimeric antigen receptor (CAR) comprising: (i) obtaining the composition comprising a plurality of vectors of the present invention (e.g., as described above); and (ii) subjecting the composition to conditions sufficient to allow for the distinct antigen binding domains, hinge domains and/or endodomains comprised in or encoded by said vectors to recombine via homologous recombination to produce a plurality of fourth vectors, wherein each of said fourth vectors encodes a CAR. The method may further comprise expressing the CAR in a cell. The method may further comprise testing the CAR for activity. In some embodiments, one or more of the first vectors encodes a scFv region. In some embodiments, one or more of the third vectors encodes a transmembrane domain. In some embodiments, one or more of the second vectors encodes a transmembrane domain. The method may further comprise randomly incorporating by recombination a fifth vector encoding a transmembrane domain with said first vectors, second vectors, and third vectors to form said fourth vector. In some embodiments, said first vectors and said seconds vector are randomly attached from a plurality of vectors encoding a plurality of distinct scFv regions and a plurality of distinct hinge regions. In some embodiments, said first vectors and said third vectors are randomly attached from a plurality of vectors encoding a plurality of distinct scFv regions and a plurality of distinct endodomains. In some embodiments, said second vectors and said third vectors are randomly attached from a plurality of vectors encoding a plurality of distinct hinge regions and a plurality of distinct endodomains. In some embodiments, said first vectors, said second vectors, and said third vectors are randomly attached from a plurality of vectors encoding a plurality of distinct scFv regions, a plurality of distinct hinge regions, and a plurality of distinct endodomains. The method may further comprise generating said fourth vectors by random attachment of said first vectors from a first library of vectors encoding a plurality of scFv regions, random attachment of said second vectors from a second library of vectors encoding a plurality of scFv regions, and random attachment of said third vectors from a third library of vectors encoding a plurality of endodomains, to form said fourth vector encoding the CAR. The first vectors may comprise a first sequence and a second site of homologous recombination. The second vectors may comprise the second sequence of homologous recombination and a third sequence of homologous recombination. The third vectors may comprise the third sequence of homologous recombination and a fourth sequence of homologous recombination. The third vectors may comprise the third sequence of homologous recombination and a fourth sequence of homologous recombination. The fourth vectors may comprise the first sequence of homologous recombination and the fourth sequence of homologous recombination. The first vectors, the second vectors, and/or the third vectors may encode a transposase. In some embodiments, a sixth vector encodes a transposase, and wherein the method comprises introducing, electroporating, or transfecting one or more of said fourth vectors and said sixth vector into a cell. The transposase may be a salmonid-type Tc1-like transposase (SB). The method may further comprise culturing or providing cells transfected with the CAR in the presence of artificial antigen presenting cells (aAPCs) that can stimulate expansion of the CAR-expressing T-cells. In some embodiments, each of the scFv region, the hinge region, and the endodomain are each encoded in a Sleeping Beauty (SB) or piggyBac transposon vector. In some embodiments, each of the first vector, the second vector, and/or the third vector are randomly attached by said recombination from a plurality of vectors encoding multiple distinct scFv regions, the hinge regions, and endodomains. In some embodiments, said first vectors, the second vectors, and the third vectors each contain a transposon; and wherein said attaching via homologous recombination comprises site specific recombination. In some embodiments, the first vectors and the second vectors each have a first homologous recombination site; and wherein the second vectors and the third vectors each have a second homologous recombination site. In some embodiments, the first vectors have a third recombination site, and wherein the fourth vectors have a fourth recombination site, wherein the third recombination site and fourth recombination site can allow for homologous recombination into a cell. The cell may be a T cell such as, e.g., an alpha beta T cell, a gamma delta T cell, or NK cell, or NKT cell. In some embodiments, the cell is a pluripotent cell such as, e.g., a stem cell or an induced pluripotent stem cell. In some embodiments, the cell is derived from a stem cell, an induced pluripotent stem cell, or a stem cell. The cell may be a T cell or NK cell derived from an induced pluripotent stem cell. In some embodiments, said distinct antigen binding domains include at least 2, 3, 4, 5, 6, 7, 8, 9, or more scFv that selectively recognize different antigens. In some embodiments, said distinct antigen binding domains include at least 2, 3, 4, 5, 6, 7, 8, 9, or more scFv that selectively recognize (i.e., specifically bind) the same antigen. In some embodiments, the antigen binding domains selectively (specifically) bind CD19, Universal Antigen (mouse), HER-3, GD2, Gp75, CS1 protein, mesothelin, phosphatidylserine, cMyc, CD22, CD4, CD44v6, CD45, CD28, CD3, CD3e, CD123, CD138, CD52, CD56, CD74, CD30, Gp75, CD38, CD33, CD20, Her1/HER3 fusion, GD2, a carbohydrate, *Aspergillus*, ROR1, c-MET, EGFR, Dectin, Ebola, a fungus, GP, HERV-K, NY-ESO-1, VEGF-R2, TGF-b2R, IgG4, Biotin, or O-AcGD2. In some embodiments, said antigen binding domains comprise or consist of scFv. The hinge region may encode the 12 AA peptide (GAGAGCAAGTACGGCCCTCCCTGCCCCCCTTG-CCCT, SEQ ID NO:1), t-20 AA peptide, IgG4 Fc Δ EQ, IgG4 Fc Δ Q, (t-12AA+t-20AA), mKate, phiLov, dsRed, Venus, eGFP, CH3 HA, (CD8 α+t-20AA), Double t-20 AA, (t-20AA+CD8α), (CD8α+Leucine Zipper Basep1), (CD8α+Leucine Zipper Acid1), 2D3, CD8 α, or IgG4 Fc. The endodomain may encode CD3ζ. The endodomain may encode one or more ITAM domains. In some embodiments, the endodomain encodes (CD28+CD3ζ), (CD28+CD27+CD3ζ), (CD28+OX40+CD3ζ), (CD28+4-1BB+CD3ζ), (CD28+CD27+OX40+CD3ζ), (CD28+4-1BB+CD27+CD3ζ), (CD28+4-1BB+OX40+CD3ζ), (4-1BB+CD3ζ), (4-1BB+OX40+CD3ζ), (4-1BB+CD27+CD3ζ), (CD27+CD3ζ), (CD27+OX 40+CD3ζ), (CD28A+CD3ζ), (CD28A+CD27+CD3ζ), (CD28A+OX40+CD3ζ), (CD28A+4-1BB+CD3ζ), (CD28A+4-1BB+OX40+CD3ζ), (CD28A+CD27+OX40+CD3ζ), (CD28A+4-1BB+CD27+CD3ζ), (4-1BB+ICOS+CD3ζ), (CD28+ICOS+CD3ζ), (ICOS+CD3ζ), CD3ζ, or CD28 only. In some embodiments, the CARs may be tested for activity, e.g., using the iQue™ Screener (IntelliCyt, Albuquerque, NM). In some embodiments CARs may evaluated for one or more characteristics (e.g., viability, upregulation of activation signals, upregulation of CD25, cytokine release, and/or cell killing) when expressed in cells such as T cells using a technique such as, e.g., flow cytometry. In some embodiments, said activity comprises ability of the CAR to selectively bind a cancer cell, selectively bind a pathogen, selectively bind a cell involved in an autoimmune disease, or promote activation of a T-cell, destruction of a T cell, differentiation of a T cell, proliferation of a T cell, de-differentation of a T cell, movement of a T cell, cytokine production by a T cell, or killing by a T cell.

In some embodiments, the cancer cell is an ovarian cancer, a lymphoma, a renal cell carcinoma, a B-cell malignancy, CLL, B-ALL, ALL, a leukemia, a B-cell malignancy or lymphoma, mantle cell lymphoma, an indolent B-cell lymphoma, Hodgkin lymphoma, AML, cervical cancer, breast cancer, colorectal cancer, ovarian cancer, neuroblastoma, skin cancer, melanoma, a lung cancer, osteosarcoma, glioma, an epithelial derived tumor, prostate cancer, or a pediatric cancer. The pathogen may be a virus, a fungi, or a bacteria. In some embodiments, said testing comprises single cell imaging, single cell genetics, assessment of single T cells or populations of T cells; measuring specific killing or serial killing, gene expression, protein expression, movement towards or away from a target, proliferation, activation-induced cell death, secretion of cytokines, or secretion of chemokines. The method may further comprise selecting a single CAR from said plurality of vectors based on a property of the single CAR. The method may further comprise therapeutically administering the single CAR to a subject. The subject may be a mammal such as, e.g., a human.

Another aspect of the present invention relates to a polypeptide comprising or consisting of CAR 217 (SEQ ID NO: 2), CAR 194 (SEQ ID NO: 3), CAR 212 (SEQ ID NO: 4), CAR 213 (SEQ ID NO: 5), CAR 265 (SEQ ID NO: 6), CAR 214 (SEQ ID NO:56), CAR 215 (SEQ ID NO:57), CAR 216 (SEQ ID NO:58), CAR 218 (SEQ ID NO:59), CAR 193 (SEQ ID NO:55), or CAR 268 (SEQ ID NO: 7).

Yet another aspect of the present invention relates to a transformed T cell expressing the polypeptide comprising or consisting of CAR 217 (SEQ ID NO:2), CAR 194 (SEQ ID NO:3), CAR 212 (SEQ ID NO:4), CAR 213 (SEQ ID NO:5), CAR 265 (SEQ ID NO:6), CAR 214 (SEQ ID NO:56), CAR 215 (SEQ ID NO:57), CAR 216 (SEQ ID NO:58), CAR 218 (SEQ ID NO:59), CAR 193 (SEQ ID NO:55), or CAR 268 (SEQ ID NO:7). The cell may be an immortalized cell. The T cell may be an alpha beta T cell, a gamma delta T cell, NK cell, NKT cell, stem cell, cells derived from stem cells, including cells of the immune system.

Another aspect of the present invention relates to a pharmaceutical preparation comprising the transformed T cell of the present invention.

Yet another aspect of the present invention relates to a nucleic acid encoding a chimeric antigen receptor comprising or consisting of CAR 217 (SEQ ID NO:2), CAR 194 (SEQ ID NO:3), CAR 212 (SEQ ID NO:4), CAR 213 (SEQ ID NO:5), CAR 265 (SEQ ID NO:6), CAR 214 (SEQ ID NO:56), CAR 215 (SEQ ID NO:57), CAR 216 (SEQ ID NO:58), CAR 218 (SEQ ID NO:59), CAR 193 (SEQ ID NO:55), or CAR 268 (SEQ ID NO:7). The nucleic acid may be comprised in a T cell such as, e.g., an alpha beta T cell, a gamma delta T cell, NK cell, NKT cell, stem cell, or a T cell derived from a pluripotent cell. The T cell may be comprised in a pharmaceutically acceptable carrier or excipient.

Another aspect of the present invention relates to a composition comprising a library of different CAR encoding vectors, the vectors of said library being randomized in terms of distinct antigen binding domains, hinge domains and/or endodomains. In some embodiments, the library randomized in terms of distinct antigen binding domains, hinge domains, and endodomains. In some embodiments, the library randomized in terms of distinct antigen binding domains and endodomains. In some embodiments, the library randomized in terms of distinct antigen binding domains and hinge domains. In some embodiments, the library randomized in terms of distinct antigen hinge domains and endodomains.

Examples of antigen binding domains, hinge regions, transmembrane domains, and endodomains that be used in methods of the present invention to generate a CAR are shown below in Table 1. The antigen binding domains, hinge regions, transmembrane domains, and endodomains are merely provided in Table 1 as non-limiting examples, and it is anticipated that one may select virtually any antigen binding domain (e.g., targeting a cancerous cell, bacteria, fungi, virus, or virus-infected cell) as desired for the particular clinical application. In Table 1, the target of the antigen binding domain is provided (e.g., "CD19" may refer to a scFv region that selectively binds CD19). In some embodiments, the antigen binding domain comprises or consists of a scFv that selectively binds the antigen. If desired, a portion of the scFv (e.g., part of the variable region of the scFv) may be randomized if desired. In some embodiments, the antigen binding domain selectively binds a protein. Alternately, the antigen binding domain may selectively bind a carbohydrate expressed on a target such as, e.g., a fungi, virus, bacteria, or cancerous cell. For example, in some embodiments, the antigen binding domain comprises or consists of Dectin-1, which can selectively bind β-glucans and carbohydrate found in fungal cell walls. In some embodiments, the CAR may selectively bind a virus, e.g., the CAR may bind a viral protein such as a hepatitis envelope protein (e.g., Krebs et al., 2013). In some embodiments, the antigen binding domain is a cytokine. The antigen binding domain may selectively bind a protein, carbohydrate, or sugar. In some embodiments, a CAR is generated from a plurality of antigen binding domains that selectively bind a single target, antigen, or the antigen binding domains may have overlapping antigens. In some embodiments, a CAR is generated from a plurality of antigen binding domains that selectively bind different targets or antigens. The endodomain in a CAR may result in an inhibitory signal (e.g., PD-1, CTLA-4, TIM-3, LAG-3, BTLA, ITIM, SHP-1, LAIR-1, TIGIT, Siglecs) or a stimulatory signal (e.g., CD27, CD28, ICOS, CD134, CD137, LCK, DAP10, ITAM, ZAP-70, LAT, SLP-76, cytokines as well as cytokine receptors; as well as combinations and mutations) in a cell expressing the CAR such as, e.g., a T cell or a natural killer (NK) cell. When the antigen binding region selectively recognizes an antigen, the endodomain may cause or promote the cell (e.g., T cell or NK cell) comprising the CAR to activate cell killing, migrate, differentiate, de-differentiate, or result in inducing an apoptotic signal in the cell. The apoptotic signal may comprise or consist of a CTLA4 apoptotic signal and/or a PD1 (protein death 1) apoptotic signal. In some embodiments, more than one distinct CAR may be expressed in a cell such as, e.g., a T cell or a NK cell. For example, a first CAR and a second CAR may be expressed in a cell, wherein the first CAR selectively binds an antigen on a healthy cell and induces an inhibitory signal via a first endodomain (e.g., reducing the probability that the T cell or NK cell will damage the healthy cell) and the second CAR selectively binds an antigen on a target cell (e.g., cancerous cell, fungi, virus-infected cell, bacteria) and induces a stimulatory signal via a second endodomain (e.g., promoting or causing cell killing of the target cell by the T cell or NK cell). A CAR generated via the methods of the present invention may be inserted in a target cell such as, e.g., a T cell or a NK cell, as integrating DNA (e.g., using electroporation and homologous recombination via a transposase/transposon vector or system) or as non-integrating DNA or RNA (e.g., viral delivery of a mRNA using a viral vector such as, e.g., a lentivirus or retrovirus). In some embodiments, the T cell encoding a CAR according to the present invention is an immortalized cell; such immortalized cells may function may be used to evaluate or measure the therapeutic potential or toxicity of the CAR. In this way, many CARs may be screened for a desired pharmacological profile, toxicity towards diseased cells or pathogens, lack of toxicity in healthy cells, and/or therapeutic efficacy.

TABLE 1

| DNA molecules that can be combined as Antigen binding domain-hinge-signaling domains to generate CARs. |
|---|
| **Antigen-binding Domain (e.g., an ScFv that selectively bind a target listed below)** |
| CD19 (mouse) (e.g., SEQ ID NO: 8) |
| CD19 (human) (e.g., SEQ. ID NO: 9) |
| CD19 (humanized) |
| Universal Antigen (mouse) (Rushworth et al., 2014) |
| CD22 (e.g., scFv from Jabbour et al., 2014 or Kong et al., 2014) |
| CD4 (e.g., scFv from Humblet-Baron et al., 2015) |
| CD44v6 (e.g., scFv from Leung 2010 or Verel 2002) |
| CD45 (e.g., scFv from Shin et al., 2011) |
| CD28 (e.g., scFv from Czerwiński et al, 2015) |
| CD3 (e.g., SEQ ID NO: 10) |
| CD3e (e.g., scFv from monoclonal antibody SPV-T3b, Life Technologies, Carlsbad, CA), |
| CD123 (e.g., SEQ ID NO: 11) |
| CD138 (e.g., scFv from Sun et al., 2007) |
| CD52 (e.g., scFv from Wang et al., 2015) |
| CD56 (e.g., scFv from Kaufmann et al., 1997) |
| CD74 (e.g., scFv from Kaufman et al., 2013) |
| CD30 (e.g., SEQ ID NO: 12) |
| Gp75 (e.g., scFv from Patel et al., 2008) |
| CD38 (e.g., scFv from de Weers et al., 2011) |
| CD33 (e.g., scFv from Manero et al., 2013) |
| CD20 (e.g., scFv from Le Garff-Tavernier et al., 2014 or Winiarska et al, 2014) |
| Her1/HER3 fusion (e.g., scFv from Sarup et al., 2008) |
| HER-3 (e.g., SEQ ID NO: 13) |
| GD2 (e.g., SEQ ID NO: 14) |
| Carbohydrates (such as an Aspergillus carbohydrate), e.g., scfv from Stynen et al., 1991) |
| ROR1 (e.g., SEQ ID NO: 15) |
| c-MET (e.g., scFv from Zhuang et al., 2014) |
| cMyc (e.g., SEQ ID NO: 16) |
| EGFR (e.g., scFv from Funakoshi et al., 2014) |
| Dectin (e.g., Dectin 1 ectodomain, SEQ ID NO: 17) |
| Dectin-1 binding site |
| Ebola virus (e.g., scFv from Audet et al., 2014 or Qiu et al., 2012) |
| Fungal antigens (e.g., scFv from Guimarães et al., 2011) |
| GP (Qiu et al., 2012) |
| Gp75 (e.g., TA99, SEQ ID NO: 18) |
| HERV-K (HERVK) (e.g., SEQ ID NO: 19) |
| NY-ESO-1 (e.g., scFv from Schultz-Thater et al., 2000) |
| VEGF-R2 (e.g., scFv from Zhang et al., 2002) |
| TGF-b2R (e.g., scFv from Leung, 2011) |
| IgG4 (e.g., scFv from Curtin et al., 2015) |
| Biotin (e.g., scFv from Vincent et al., 1993) |
| O-AcGD2 (e.g., scFv from Goldberg et al., 2014 or Ahmed et al., 2014) |
| CS1 protein (e.g., Elotuzumab or huLuc63, SEQ ID NO: 20) |
| Mesothelin (e.g., using the SS-1 scFv, SEQ ID NO: 21) |
| Phosphatidylserine (e.g., scFv from Gerber et al., 2011) |
| **Hinge/Scaffold** |
| 12 AA (peptide) (e.g., SEQ ID NO: 1) |
| t-20 AA (peptide) (e.g., SEQ ID NO: 22) |
| CD8 α (e.g., SEQ ID NO: 23) |
| IgG4 Fc (e.g., SEQ ID NO: 24) |
| 2D3 (e.g., SEQ ID NO: 25) |
| IgG4 Fc Δ EQ (IgG4Fc N40Q) (e.g., SEQ ID NO: 26) |
| IgG4 Fc Δ Q (IgG4Fc L18E N40Q) (e.g. SEQ ID NO: 27) |
| t-12AA + t-20AA |
| mKate (e.g., SEQ ID NO: 28) |
| phiLov (e.g., SEQ ID NO: 29) |
| dsRed (e.g., SEQ ID NO: 30) |
| Venus (e.g., SEQ ID NO: 31) |
| eGFP (e.g., SEQ ID NO: 32) |
| CH3 HA (e.g., SEQ ID NO: 33) |
| mTFP-1 (e.g., SEQ ID NO: 34) |
| CD8 α + t-20AA |
| Double t-20 AA |
| t-20AA + CD8α |
| CD8α + Leucine Zipper Basep1 (e.g., SEQ ID NO: 35) |
| CD8α + Leucine Zipper Acid1 (e.g., SEQ ID NO: 36) |

TABLE 1-continued

| DNA molecules that can be combined as Antigen binding domain-hinge-signaling domains to generate CARs. |
|---|
| **Transmembrane domain** |
| CD28 (e.g., SEQ ID NO: 37) |
| CD137 (4-1BB) (e.g., SEQ ID NO: 38) |
| CD8α (e.g., SEQ ID NO: 39) |
| CD3ζ (e.g., SEQ ID NO: 40) |
| **Endo-domain (signaling domain)** |
| CD28 + CD3ζ |
| CD28 + CD27 + CD3ζ |
| CD28 + OX40 + CD3ζ |
| CD28 + 4-1BB + CD3ζ |
| CD28 + CD27 + OX40 + CD3ζ |
| CD28 + 4-1BB + CD27 + CD3ζ |
| CD28 + 4-1BB + OX40 + CD3ζ |
| 4-1BB + CD3ζ |
| 4-1BB + OX40 + CD3ζ |
| 4-1BB + CD27 + CD3ζ |
| CD27 + CD3ζ |
| CD27 + OX 40 + CD3ζ |
| CD28Δ + CD3ζ |
| CD28Δ + CD27 + CD3ζ |
| CD28Δ + OX40 + CD3ζ |
| CD28Δ + 4-1BB + CD3ζ |
| CD28Δ + 4-1BB + OX40 + CD3ζ |
| CD28Δ + CD27 + OX40 + CD3ζ |
| CD28Δ + 4-1BB + CD27 + CD3ζ |
| 4-1BB + ICOS + CD3ζ |
| CD28 + ICOS + CD3ζ |
| ICOS + CD3ζ |
| CD3ζ |
| CD28 only |

ζ—zeta; Δ—mutant;
Note =
4-1BB is also referred to as CD137; "+" refers to the fusion of the different regions.

For example, in some embodiments, the following antigen-binding domains, hinge/scaffolds, transmembrane domains, and endodomains may be used, as shown in Table 2. Examples of sequences included in signaling domains, e.g., in Table 1 or Table 2, include CD27 (SEQ ID NO:41), CD28 (SEQ ID NO:42), CD28Δ (SEQ ID NO:43), CD134 (OX40) (SEQ ID NO:44), CD137 (41BB) (SEQ ID NO:45), ICOS (SEQ ID NO:46) and CD3 zeta (SEQ ID NO:47). Examples of scFv Anti-EGFR domains as listed in Table 2 include Nimotuximab (SEQ ID NO:48) and Cetuximab (SEQ ID NO:49). An example of a scFv Anti-Phosphatidylserine as listed in Table 2 is Bavituximab (SEQ ID NO:50).

TABLE 2

| Example of libraries used to generate CAR |
|---|
| **ScFv** |
| Anti-CS1 protein |
| Anti-mesothelin (SS-1) |
| Anti-CD123 |
| Anti-CD19 human |
| Anti-CD19 mouse |
| Anti-CD3 |
| Anti-CD30 |
| Anti-Dectin |
| Anti-G2D |
| Anti-Gp75 |
| Anti-HERVK |
| Anti-CD22 |
| Anti-ROR-1 |

TABLE 2-continued

| Example of libraries used to generate CAR |
|---|
| Anti-EGFR |
| Anti-HER-3 |
| Anti-Phosphatidylserine |
| Hinge/Scaffold |
| t-12 AA (peptide) |
| t-20 AA (peptide) |
| CD8 α |
| IgG4 Fc |
| IgGdFc Δ EQ |
| IgG4Fc Δ Q |
| t-12AA + t-20AA |
| mKate |
| phiLov |
| dsRed |
| Venus |
| eGFP |
| CH3 HA |
| CD8 α + t-20AA |
| Double t-20 AA |
| 1-20AA + CD8α |
| CD8α + Leucine Zipper Basep1 |
| CD8α + Leucine Zipper Acid1 |
| Transmembrane domain |
| CD28 |
| 4-1BB |
| CD3ζ |
| Signaling Domain |
| CD28 + CD3ζ |
| CD28 + CD27 + CD3ζ |
| CD28 + OX40 + CD3ζ |
| CD28 + 4-1BB + CD3ζ |
| CD28 + CD27 + OX40 + CD3ζ |
| CD28 + 4-1BB + CD27 + CD3ζ |
| CD28 + 4-1BB + OX40 + CD3ζ |
| 4-1BB + CD3ζ |
| 4-1BB + OX40 + CD3ζ |
| 4-1BB + CD27 + CD3ζ |
| CD28Δ + CD3ζ |
| CD28Δ + CD27 + CD3ζ |
| CD28Δ + OX40 + CD3ζ |
| CD28Δ + 4-1BB + CD3ζ |
| CD28Δ + 4-1BB + OX40 + CD3ζ |
| CD28Δ + CD27 + OX40 + CD3ζ |
| CD28Δ + 4-1BB + CD27 + CD3ζ |
| 4-1BB + ICOS + CD3ζ |
| CD28 + ICOS + CD3ζ |
| ICOS + CD3ζ |
| CD3ζ |
| CD28 only |

The term "chimeric antigen receptors (CARs)" or "CAR" as used herein, includes artificial T-cell receptors, chimeric T-cell receptors, or chimeric immunoreceptors. CARs are generally engineered receptors that may graft an artificial specificity onto a particular immune effector cell. CARs may be employed to impart the specificity of a monoclonal antibody onto a T cell, thereby allowing a large number of specific T cells to be generated, for example, for use in an adoptive cell therapy. In some embodiments, CARs direct specificity of the cell to a tumor associated antigen. In preferred embodiments, CARs comprise an endodomain (comprising an intracellular activation domain), a transmembrane domain, a hinge or scaffold region, and an extracellular domain comprising a targeting domain (e.g., a scFv derived from a monoclonal antibody). In some embodiments, the extracellular targeting domain may be a ligand of a receptor (e.g., a peptide that selectively binds a protein receptor). In some embodiments, one can target malignant cells by redirecting the specificity of T cells by using a CAR specific for the malignant cells (e.g., by using an anti-CD19 scFv to target a cancerous B-lineage cell).

Examples of scFv regions, hinge/scaffold regions, transmembrane domains, and endodomains are shown in Table 1 and examples of related sequences are also provided herein. Note in Table 1 that the scFv regions may refer to a plurality of scFv regions for a particular target (e.g., "CD19" in Table 1 may refer to a single monoclonal antibody sequence, or in some preferred embodiments, it may refer to a plurality of scFv regions derived from monoclonal antibodies that selectively target CD19). It is anticipated that methods of the present invention may be used to generate a CAR that comprises, e.g., a fusion of any combination of a scFv region, hinge/scaffold, transmembrane domain, and endodomain of Table 1. For example, in some embodiments, the CAR may comprise a scFv region that selectively targets CD19 (e.g., derived from a mouse, human, or humanized monoclonal antibody) fused to an IgG4 Fc hinge/scaffold region, a CD28 transmembrane domain, and an endodomain comprising CD28 and CD3ζ. In some embodiments, the CAR may comprise a scFv region that selectively targets ROR1 fused to IgG4 Fc hinge/scaffold region, a CD28 transmembrane domain, and an endodomain comprising CD28 and CD3ζ. In some embodiments, the CAR may comprise a scFv region that selectively targets ROR1 fused to IgG4 Fc hinge/scaffold region, a CD28 transmembrane domain, and an endodomain comprising 4-1BB and CD3. In some embodiments, the CAR may comprise a scFv region that selectively targets CD19 (e.g., derived from a mouse, human, or humanized monoclonal antibody) fused to IgG4 Fc hinge/scaffold region, a CD28 transmembrane domain, and an endodomain comprising CD28 and CD3ζ.

As used herein, the term "antigen" is a molecule capable of being bound by an antibody or T-cell receptor. An antigen may generally be used to induce a humoral immune response and/or a cellular immune response leading to the production of B and/or T lymphocytes.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Expression of CAR (Fc) and $CD8^+$ in T cells after 66 days post electroporation by flow cytometry. The cells were expanded in aAPC loaded with CD19 antigen (clone 4) (FIG. 2B) Lysis of CD19+ EL-4 was compared to background lysis of $CD19^{neg}$ EL-4 using 4-h chromium release assay by CD19CAR+ T cells Clinical Grade (CG) CD19CAR+ T cells by triple recombination sites (EZ CAR) and $CAR^{neg}$ T cells. The $CAR^{neg}$ T were expanded in with irradiated and anti-CD3 (OKT3) loaded K562-derived aAPC clone #4.

FIG. 25: CD3-zeta. Query=SEQ ID NO:51; Subject—top=SEQ ID NO:52; Subject—middle=SEQ ID NO:53; Subject—bottom=SEQ ID NO:54.

FIG. 31: Cytotoxicity.

FIG. 32: Cytotoxicity.

FIG. 34: IFN-γ production.

FIGS. 41A-C: FIGS. 41A-B, Nalm-6; EL-4 CD19+ cells; patient tumor cells with MCL and CLL (targets) and were previously modified to express GFP. $5\times10^3$ target cells were incubated with increasing concentration of CD19RIgG4CD28CAR T cells, CD19RCD8αCD28 CAR T cells and $CAR^{neg}$ T cells (used as the control) for 4 hours. After 4 hours the cells were acquired by IntelliCyt's iQue and the data analyses were made in their proprietary software. FIG. 41C, The graphs are representing the killing percentage of CAR T cells against tumor cells. The ratio between effector and target cells ranged from 0 to 40 cells.

DESCRIPTION OF ILLUSTRATIVE EMBODIMENTS

Figure 1:
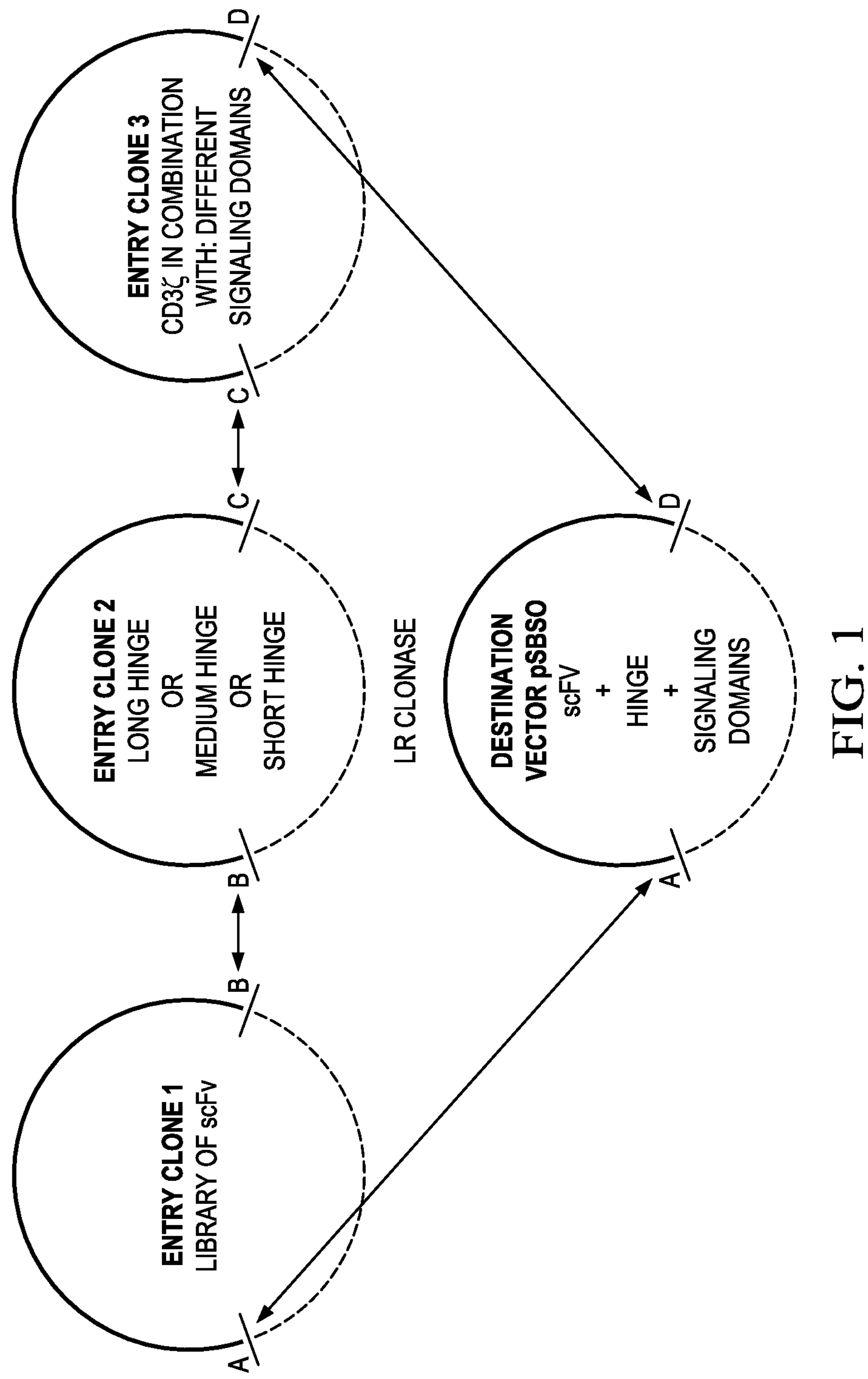
FIG. 1. Cloning vectors used to re-assemble CARs using three donor plasmids expressing (i) specific scFv, (ii) extracellular hinge and (iii) endodomains. This approach will be adapted to generate panels of CARs that differ in hinge, transmembrane, and intracellular regions. Engineering CAR molecules from components scFv, IgG4 Fc (Long hinge); or CD8a (Medium hinge) or peptide only (Small hinge) and CD3ζιν combinations with different signaling domains using triple recombination site system. A library of scFv and distinct scaffolds and signaling domains encoded in three donor plasmids (entry clones), are recombined in to the expression DNA vector. This approach generated multiple CAR species in the format scFv-B-scaffold-C-signaling domain(s).

Provided herein are methods for generating chimeric antigen receptors (CARs). The method utilizes a plurality of vectors each encoding an antigen binding domain (e.g., a scFv region), a hinge region, a transmembrane region, and/or an endodomain. For example in some embodiments a first vector encodes the antigen binding domain, a second vector encodes the hinge region, and a third region encodes an endodomain. In some embodiments, the transmembrane region is encodes either in the second vector, in the third vector, or in a fourth vector. In some preferred embodiments, the vectors can homologously recombine to form a nucleic acid encoding a CAR comprising the antigen binding domain, the hinge region, the transmembrane region, and the endodomain. In this way, many CAR may be generated and screened for a desired activity such as, e.g., selective recognition and killing of a cancerous cell expressing an antigen that is selectively bound by the CAR. The CAR may then be expressed in a cell such as a T cell or a natural killer (NK) cell as an integrating nucleic acid (e.g., a DNA integrated into the host genome using a transposase/transposon) or as a non-integrating nucleic acid (e.g., a mRNA delivered via a viral vector such as a lentivirus or retrovirus). The T cell or NK cell expressing the CAR may then be administered in a pharmaceutical preparation or excipient to a subject such as a human patient to treat or prevent a disease (e.g., a cancer, a fungal infection, a bacterial infection, or a viral infection).

I. Library Generation

Libraries encoding a plurality of scFv regions, hinge/scaffold regions, transmembrane domains, and endodomains (signaling domains) may be generated by methods known to one of skill in the art. In some embodiments, multiple possibilities are available for two or three of the scFv regions, hinge/scaffold regions, and endodomains (signaling domains). In some embodiments, multiple possibilities are available for two, three, or all of the scFv regions, hinge/scaffold regions, transmembrane domains, and endodomains (signaling domains). Examples of scFv regions, hinge/scaffold regions, transmembrane domains, and endodomains (signaling domains) are provided, e.g., in Table 1. In some embodiments, the library may encode a plurality of scFv that target different antigens, such as such as multiple anti-cancer or tumor-targeting antigens; in other embodiments, the library may encode a plurality of different scFv that selectively bind a single target (e.g., a single anticancer antigen such as CD19, etc.). In this way, the methods may be used to either identify which tumor-targeting construct may work more effectively for a given cell sample (e.g., to be used in a personalized medicine) or the methods may be used to identify new CAR that function more effectively in targeting a given antigen. The scFv region generally comprises a variable light (VL) and a variable heavy (VH) chain derived from an antibody. In some embodiments, portions of the VL and VH regions may be randomized if desired. General methods for generating libraries include, e.g., the generation of yeast libraries, bacterial, phage libraries, infiltrating B cells, hybridomas (including from human and rodents), or libraries from llamas, camels, equine libraries, and in silico methods (See, e.g., Lennard, 2002).

In some embodiments, the different vectors encoding the scFv, hinge/scaffold region, transmembrane domain, and endodomain are fused to form a single vector encoding a CAR. The fusion may occur via transposon-mediated homologous recombination.

For example, in some embodiments, the vectors encoding the scFv, hinge/scaffold region, transmembrane domain, and/or endodomain may be Sleeping Beauty (SB) or piggyBac DNA plasmids. Sleeping Beauty (SB) and piggyBac DNA plasmids are described, e.g., in Maiti et al. (2013), Singh et al. (2008), and Huls et al. (2013). In some embodiments, the transposon is mediated by a salmonid-type Tc1-like transposase (SB). In some preferred embodiments, the vector encoding the CAR is transfected or incorporated into T cells from a subject, such as a human patient with cancer, via the methods as described in Singh et al., 2014 or Huls et al. For example, DNA vectors derived from the Sleeping Beauty (SB) system can be used to avoid expense and manufacturing difficulties associated with transducing T cells with recombinant viral vectors. After electroporation, the transposon/transposase can improve the efficiency of integration of plasmids used to express CAR and other transgenes in T cells. The SB system combined with artificial antigen-presenting cells (aAPC) can selectively propagate and produce CAR(+) T cells suitable for human application. In some embodiments, synchronous electro-transfer of two DNA plasmids, a SB transposon (encoding a CAR of interest) and a SB transposase (e.g., SB11) may be followed by retrieval of stable integrants by the every-7-day additions (stimulation cycle) of γ-irradiated aAPC in the presence of soluble recombinant human IL-2 and IL-21. For example, 4 cycles (28 days of continuous culture) may be undertaken to generate clinically-appealing numbers of T cells that stably express a CAR of interest. Use of a transposon/transposase system may be utilized for delivery of T cells expressing a CAR as described, e.g., in Hackett et al.

II. Chimeric Antigen Receptors

Embodiments of the present invention involve generation and identification of nucleic acids encoding an antigen-specific chimeric antigen receptor (CAR) polypeptide. In some embodiments, the CAR is humanized to reduce immunogenicity (hCAR).

In some embodiments, the CAR may recognize an epitope comprised of the shared space between one or more antigens. Pattern recognition receptors, such as Dectin-1, may be used to derive specificity to a carbohydrate antigen. In certain embodiments, the binding region may comprise complementary determining regions of a monoclonal antibody, variable regions of a monoclonal antibody, and/or antigen binding fragments thereof. In some embodiments the binding region is an scFv. In another embodiment, a peptide (e.g., a cytokine) that binds to a receptor or cellular target may be included as a possibility or substituted for a scFv region in the binding region of a CAR. Thus, in some embodiments, a CAR may be generated from a plurality of vectors encoding multiple scFv regions and/or other targeting proteins. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptor selectivity are generally found in the CDRs, these regions are sometimes referred to as hypervariable domains. Among these, CDR3 shows the greatest variability as it is encoded by a recombination of the VJ (VDJ in the case of heavy chain and TCR αβ chain) regions.

A CAR-encoding nucleic acid generated via the present invention may comprise one or more human genes or gene fragments to enhance cellular immunotherapy for human patients. In some embodiments, a full length CAR cDNA or coding region may be generated via the methods described herein. The antigen binding regions or domain may comprise a fragment of the $V_H$ and $V_L$ chains of a single-chain variable fragment (scFv) derived from a particular human monoclonal antibody, such as those described in U.S. Pat. No. 7,109,304, incorporated herein by reference. In some embodiments, the scFv comprises an antigen binding domains of a human antigen-specific antibody. In some embodiments, the scFv region is an antigen-specific scFv encoded by a sequence that is optimized for human codon usage for expression in human cells.

The arrangement of the antigen-binding domain of a CAR may be multimeric, such as a diabody or multimers. The multimers can be formed by cross pairing of the variable portions of the light and heavy chains into what may be referred to as a diabody. The hinge portion of the CAR may in some embodiments be shortened or excluded (i.e., generating a CAR that only includes an antigen binding domain, a transmembrane region and an intracellular signaling domain). A multiplicity of hinges may be used with the present invention, e.g., as shown in Table 1. In some embodiments, the hinge region may have the first cysteine maintained, or mutated by a proline or a serine substitution, or be truncated up to the first cysteine. The Fc portion may be deleted from scFv used to as an antigen-binding region to generate CARs according to the present invention. In some embodiments, an antigen-binding region may encode just one of the Fc domains, e.g., either the CH2 or CH3 domain from human immunoglobulin. One may also include the hinge, CH2, and CH3 region of a human immunoglobulin that has been modified to improve dimerization and oligermerization. In some embodiments, the hinge portion of may comprise or consist of a 8-14 amino acid peptide (e.g., a 12 AA peptide), a portion of CD8α, or the IgG4 Fc. In some embodiments, the antigen binding domain may be suspended from cell surface using a domain that promotes oligomerization, such as CD8 alpha. In some embodiments, the antigen binding domain may be suspended from cell surface using a domain that is recognized by monoclonal antibody (mAb) clone 2D3 (mAb clone 2D3 described, e.g., in Singh et al., 2008).

The endodomain or intracellular signaling domain of a CAR can generally cause or promote the activation of at least one of the normal effector functions of an immune cell comprising the CAR. For example, the endodomain may promote an effector function of a T cell such as, e.g., cytolytic activity or helper activity including the secretion of cytokines. The effector function in a naive, memory, or memory-type T cell may include antigen-dependent proliferation. The terms "intracellular signaling domain" or "endodomain" refers to the portion of a CAR that can transduce the effector function signal and/or direct the cell to perform a specialized function. While usually the entire intracellular signaling domain may be included in a CAR, in some cases a truncated portion of an endodomain may be included. Generally, endodomains include truncated endodomains, wherein the truncated endodomain retains the ability to transduce an effector function signal in a cell.

In some embodiments, an endodomain comprises the zeta chain of the T-cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. Examples of these alternative transmembrane and intracellular domains can be found, e.g., Gross et al. (1992), Stancovski et al. (1993), Moritz et al. (1994), Hwu et al. (1995), Weijtens et al. (1996), and Hekele et al. (1996), which are incorporated herein be reference in their entirety. In some embodiments, an endodomain may comprise the human CD3ζ intracellular domain.

The antigen-specific extracellular domain and the intracellular signaling-domain are preferably linked by a transmembrane domain. Transmembrane domains that may be included in a CAR include, e.g., the human IgG4 Fc hinge and Fc regions, the human CD4 transmembrane domain, the human CD28 transmembrane domain, the transmembrane human CD3ζ domain, or a cysteine mutated human CD3ζ domain, or a transmembrane domains from a human transmembrane signaling protein such as, e.g., the CD16 and CD8 and erythropoietin receptor. Examples of transmembrane domains are provided, e.g., in Table 1.

In some embodiments, the endodomain comprises a sequence encoding a costimulatory receptors such as, e.g., a modified CD28 intracellular signaling domain, or a CD28, CD27, OX-40 (CD134), DAP10, or 4-1BB (CD137) costimulatory receptor. In some embodiments, both a primary signal initiated by CD3ζ, an additional signal provided by a human costimulatory receptor may be included in a CAR to more effectively activate a transformed T cells, which may help improve in vivo persistence and the therapeutic success of the adoptive immunotherapy. As noted in Table 1, the endodomain or intracellular receptor signaling domain may comprise the zeta chain of CD3 alone or in combination with an Fcγ RIII costimulatory signaling domains such as, e.g., CD28, CD27, DAP10, CD137, OX40, CD2, 4-1BB. In some embodiments, the endodomain comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, 1, 2, 3, 4 or more cytoplasmic domains may be included in an endodomain. For example, in some CARs it has been observed that at least two or three signaling domains fused together can result in an additive or synergistic effect.

In some aspects, an isolated nucleic acid segment and expression cassette including DNA sequences that encode a CAR may be generated. A variety of vectors may be used. In some preferred embodiments, the vector may allow for delivery of the DNA encoding a CAR to immune such as T cells. CAR expression may be under the control of regulated eukaryotic promoter such as, e.g., the MNDU3 promoter, CMV promoter, EF1alpha promoter, or Ubiquitin promoter. Also, the vector may contain a selectable marker, if for no other reason, to facilitate their manipulation in vitro. In some embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they can bind native antigen on the target cell surface in an HLA-independent fashion. For example, a scFv constructs may be fused to sequences coding for the intracellular portion of the CD3 complex's zeta chain (ζ), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: ζ systems (Eshhar et al., 1997; Altenschmidt et al., 1997; Brocker et al., 1998).

The antigen binding region may, e.g., be from a human or non-human scFv. One possible problem with using non-human antigen binding regions, such as murine monoclonal antibodies, is reduced human effector functionality and a reduced ability to penetrate into tumor masses. Furthermore, non-human monoclonal antibodies can be recognized by the human host as a foreign protein, and therefore, repeated injections of such foreign antibodies might lead to the induction of immune responses leading to harmful hypersensitivity reactions. For murine-based monoclonal antibodies, this effect has been referred to as a Human Anti-Mouse Antibody (HAMA) response. In some embodiments, inclusion of human antibody or scFv sequences in a CAR may result in little or no HAMA response as compared to some murine antibodies. Similarly, the inclusion of human sequences in a CAR may be used to reduce or avoid the risk of immune-mediated recognition or elimination by endogenous T cells that reside in the recipient and might recognize processed antigen based on HLA.

In some embodiments, the CAR comprises: a) an intracellular signaling domain, b) a transmembrane domain, c) a hinge region, and d) an extracellular domain comprising an antigen binding region. In some embodiments, the intracellular signaling domain and the transmembrane domain are encoded with the endodomain by a single vector that can be fused (e.g., via transposon-directed homologous recombination) with a vector encoding a hinge region and a vector encoding an antigen binding region. In other embodiments, the intracellular signaling region and the transmembrane region may be encoded by two separate vectors that are fused (e.g., via transposon-directed homologous recombination).

In some embodiments, the antigen-specific portion of a CAR, also referred to as an extracellular domain comprising an antigen binding region, selectively targets a tumor associated antigen. A tumor associated antigen may be of any kind so long as it is expressed on the cell surface of tumor cells. Examples of tumor associated antigens that may be targeted with CARs generated via the present invention include, e.g., CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, Dectin-1, and so forth. In some embodiments that antigen specific portion of the CAR is a scFv. Examples of tumor-targeting scFv are provided in Table 1. In some embodiments, a CAR may be co-expressed with a membrane-bound cytokine, e.g., to improve persistence when there is a low amount of tumor-associated antigen. For example, a CAR can be co-expressed with membrane-bound IL-15.

In some embodiments, an intracellular tumor associated antigen such as, e.g., HA-1, survivin, WT1, and p53 may be targeted with a CAR. This may be achieved by a CAR expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA.

The pathogen recognized by a CAR may be essentially any kind of pathogen, but in some embodiments the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*. In some embodiments the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, naked DNA or a suitable vector encoding a CAR can be introduced into a subject's T cells (e.g., T cells obtained from a human patient with cancer or other disease). Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. In some embodiments, the use of naked DNA may reduce the time required to produce T cells expressing a CAR generated via methods of the present invention.

Alternatively, a viral vector (e.g., a retroviral vector, adenoviral vector, adeno-associated viral vector, or lentiviral vector) can be used to introduce the chimeric construct into T cells. Generally, a vector encoding a CAR that is used for transfecting a T cell from a subject should generally be non-replicating in the subject's T cells. A large number of vectors are known that are based on viruses, where the copy number of the virus maintained in the cell is low enough to maintain viability of the cell. Illustrative vectors include the pFB-neo vectors (STRATAGENE®) as well as vectors based on HIV, SV40, EBV, HSV, or BPV.

Once it is established that the transfected or transduced T cell is capable of expressing a CAR as a surface membrane protein with the desired regulation and at a desired level, it can be determined whether the chimeric receptor is functional in the host cell to provide for the desired signal induction. Subsequently, the transduced T cells may be reintroduced or administered to the subject to activate anti-tumor responses in the subject. To facilitate administration, the transduced T cells may be made into a pharmaceutical composition or made into an implant appropriate for administration in vivo, with appropriate carriers or diluents, which are preferably pharmaceutically acceptable. The means of making such a composition or an implant have been described in the art (see, for instance, Remington's Pharmaceutical Sciences, 16th Ed., Mack, ed. (1980)). Where appropriate, transduced T cells expressing a CAR can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Generally, a pharmaceutically acceptable form is preferably employed that does not ineffectuate the cells expressing the chimeric receptor. Thus, desirably the transduced T cells can be made into a pharmaceutical composition containing a balanced salt solution such as Hanks' balanced salt solution, or normal saline.

IV. Artificial Antigen Presenting Cells

In some cases, aAPCs are useful in preparing CAR-based therapeutic compositions and cell therapy products. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009).

aAPCs may be used to expand T Cells expressing a CAR. During encounter with tumor antigen, the signals delivered to T cells by antigen-presenting cells can affect T-cell programming and their subsequent therapeutic efficacy. This has stimulated efforts to develop artificial antigen-presenting cells that allow optimal control over the signals provided to T cells (Turtle et al., 2010). In addition to antibody or antigen of interest, the aAPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (also called B7 or CD80), which can bind to CD28 and/or CTLA-4 molecules on the surface of T cells, thereby affecting, e.g., T-cell expansion, Th1 differentiation, short-term T-cell survival, and cytokine secretion such as interleukin (IL)-2 (see Kim et al., 2004). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

Cells selected to become aAPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become aAPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, aAPCs preferably retain the deficiencies and poikilothermic properties that were possessed by the cells prior to their modification to generate the aAPCs. Exemplary aAPCs either constitute or are derived from a transporter associated with antigen processing (TAP)-deficient cell line, such as an insect cell line. An exemplary poikilothermic insect cells line is a *Drosophila* cell line, such as a Schneider 2 cell line (e.g., Schneider, J. m 1972). Illustrative methods for the preparation, growth, and culture of Schneider 2 cells, are provided in U.S. Pat. Nos. 6,225,042, 6,355,479, and 6,362,001.

aAPCs may be subjected to a freeze-thaw cycle. For example, aAPCs may be frozen by contacting a suitable receptacle containing the aAPCs with an appropriate amount of liquid nitrogen, solid carbon dioxide (dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preservatives that might detrimentally impact the freeze-thaw procedures, such as dimethyl sulfoxide (DMSO), polyethylene glycols (PEGs), and other preservatives, may be advantageously absent from media containing aAPCs that undergo the freeze-thaw cycle, or are essentially removed, such as by transfer of aAPCs to media that is essentially devoid of such preservatives.

In other preferred embodiments, xenogenic nucleic acid and nucleic acid endogenous to the aAPCs may be inactivated by crosslinking, so that essentially no cell growth, replication or expression of nucleic acid occurs after the inactivation. For example, aAPCs may be inactivated at a point subsequent to the expression of exogenous MHC and assisting molecules, presentation of such molecules on the surface of the aAPCs, and loading of presented MHC molecules with selected peptide or peptides. Accordingly, such inactivated and selected peptide loaded aAPCs, while rendered essentially incapable of proliferating or replicating, may retain selected peptide presentation function. The crosslinking can also result in aAPCS that are essentially free of contaminating microorganisms, such as bacteria and viruses, without substantially decreasing the antigen-presenting cell function of the aAPCs. Thus crosslinking can be used to maintain the important APC functions of aAPCs while helping to alleviate concerns about safety of a cell therapy product developed using the aAPCs. For methods related to crosslinking and aAPCs, see for example, U.S. Patent Application Publication No. 20090017000, which is incorporated herein by reference.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Generation of Clinical-Grade DNA Plasmids

The SB transposon, CoOpCD19RCD28ζ/pSBSO, expresses the human codon optimized (CoOp) 2nd generation CoOpCD19RCD28ζ CAR under EF-1/HTLV hybrid composite promoter (InvivoGen) comprised of Elongation Factor-1a (EF-1a [Kim et al., 1990] and 59 untranslated region of the Human T-Cell Leukemia Virus (HTLV) [Singh et al., 2011; Davies et al., 2010]. The derivation of this DNA plasmid is described in FIG. S1. The SB transposase, SB11, under the cytomegalovirus (CMV) promoter is expressed in cis from the DNA plasmid pCMV-SB11 (Singh et al., 2011; Singh et al., 2008). Both plasmids were sequenced in their entirety and manufactured by Waisman Clinical Biomanufacturing Facility (Madison, WI) using kanamycin for selection of the bacterial strain *E. Coli* DH5a.

Generation of Triple Site-Specific Recombination DNA Plasmids—EZ-Build-CARs

Using the DNA sequence from the CAR described above (CoOpCD19RCD28z/pSBSO), the parts CD19 ScFv, the hinge IgG4 Fc and the domain CD28 transmembrane and cytosolic portion conjugated with CD3ζ signaling domain were flanked by lambda recombination sites, synthetized by Geneart (Life Technologies) as PCR products. These three parts were individually inserted into pDonors221 plasmids (by the enzyme BP clonase (both from Invitrogen). The three plasmids were recombined with the triple site specific recombination Sleeping Beauty plasmid by the enzyme LR PLUS clonase (Invitrogen) generating the EZ-Build CD19CD28ζ CAR in the format scFv-B-scaffold-C-signaling domain(s) (FIG. 1).

Cell Counting

Trypan-blue exclusion was used to distinguish live from dead cells and counted using Cellometer (Nexecelom Bioscience) (Singh et al., 2011).

Isolation of PBMC

Leukapheresis products from two male volunteer healthy donors were purchased from Key Biologics LLC (Memphis, Tenn.). The peripheral blood mononuclear cells (PBMC) were isolated by our adapting the Biosafe Sepax system (Eysins, Switzerland) for work in compliance with cGMP. Briefly, after closing all the clamps on the CS-900 kit, 100 mL Ficoll (GE Healthcare) was aseptically transferred via 60 mL syringes to a density gradient media bag ("ficoll bag") via Luer-lock connector and the tubing was heat sealed using a hand held sealer (Sebra, Model #2380). The kit was spike-connected to a 1,000 mL bag containing CliniMACS buffer (PBS/EDTA, Miltenyi, Cat #70026) with 20 mL 25% Human Serum Albumin (HSA) (Baxter) (2% v/v, wash buffer) for washes, a final product bag [300 mL Transfer Pack with Coupler (Baxter/Fenwal 4R2014)] and a reagent/blood bag. Using the density gradient-based separation protocol (v126), the syringe piston was loaded into the centrifuge chamber and the cover of the Sepax aAPC (clone #4) to selectively propagate CAR+ T cells The c-irradiated aAPC were used to numerically expand the genetically modified T cells. Thawed aAPC from WCB were propagated in CM for up to 60 days in VueLife cell culture bags and harvested using Biosafe Sepax II harvest procedure. Briefly, CS-490.1 kit was connected to a 300 mL output bag (transfer pack) via Luer lock connection. The separation chamber was installed in the pit and the tubing was inserted into the optical sensor and stopcocks aligned in T-position. After connecting the pressure sensor line, the product bag and supernatant/plasma bags were hung on the holder. The modified protocol PBSCv302 was selected from the Sepax menu and the volume of input product to be processed (initial volume) was set to #840 mL. After validation and kit test, the procedure was started. Following completion, the bags were removed, clamps closed and the kit was removed. The cells from the final product bag were aseptically removed, washed twice with wash media (10% HSA in Plasmalyte) and counted. aAPC were irradiated (100 Gy) using a CIS BIO International radiator (IBL-437 C #09433) and cryopreserved for later use in cryopreservation media using controlled-rate freezer (Planer Kryo 750). The anti-CD3 (OKT3) loaded K562-derived aAPC clone #4 was used to propagate control (CARneg) autologous control T cells that had not undergone genetic modification. The aAPC, obtained from culture, were incubated overnight in serum-free X-Vivo 15 (cat #04-744Q, Lonza) containing 0.2% acetyl cysteine (Acetadote, Cumberland Pharmaceuticals) termed Loading Medium (LM). The next day cells were washed, irradiated (100 Gy) using a Gamma Cell 1000 Elite Cs-137 radiator (MDS Nordion), resuspended in LM at a concentration of 106 cells/mL along with 1 mg/$10^6$ cells of functional grade purified anti-human CD3 (clone-OKT3, 16-0037-85, eBioscience) and incubated with gentle agitation on a 3-D rotator (Lab-Line) at 4° C. for 30 minutes. Following three washes with LM the cells were used in experiments or frozen in aliquots in liquid nitrogen in vapor layer for later use.

Manufacture of CAR+ T Cells

Thawed PBMC were resuspended in (i) Human T-cell kit (cat #VPA-1002, Lonza; 100 μL for $2\times10^7$ cells in one cuvette), with (ii) the DNA plasmid (CoOpCD19RCD28/pSBSO) coding for CD19RCD28 CAR transposon (15 μg supercoiled DNA per $2\times10^7$ PBMC per cuvette), and (iii) the DNA plasmid (pCMVSB11) coding for SB11 transposase (5 μg supercoiled DNA per $2\times10^7$ PBMC per cuvette). This mixture was immediately transferred to a cuvette (Lonza), electroporated (defining culture day 0) using Nucleofector II (Program U-14, Amaxa/Lonza), rested in 10% RPMI complete media for 2 to 3 hours, and after a half-media change, incubated overnight at 37° C., 5% $CO_2$. The following day, cells were harvested, counted, phenotyped by flow cytometry, and co-cultured with c-irradiated aAPC at a ratio of 1:2 (CAR+ T cell:aAPC), which marked culture day 1 and the beginning of a 7-day stimulation cycle. IL-21 (cat #AF-200-21, PeproTech) and IL-2 (cat #NDC 65483-116-07, Novartis) were added on a Monday-Wednesday-Friday schedule onwards of day 1 and day 7 respectively. NK cells can prevent the numeric expansion of CAR+ T cells, especially if their overgrowth occurs early in the tissue culturing process. Therefore, a CD56-depletion was performed if CD3negCD56+ cells $10% using CD56 beads (cat #70206, Miltenyi Biotech, 20 mL beads/107 cells) on LS columns (cat #130-042-401, Miltenyi Biotech) in CliniMACS buffer containing 25% HSA (80 mL/107 cells).

Generation of $CAR^{neg}$ Control T Cells

As a control, $5\times10^6$ mock transfected PBMC were co-cultured with irradiated and anti-CD3 (OKT3) loaded K562-derived aAPC clone #4 at a ratio of 1:1 in a 7-day stimulation cycle. All the cultures were supplemented with IL-21 (30 ng/mL) from culture day 1 onwards, and IL-2 (50 U/mL) starting 7 days after the start of the culture. All cytokines were subsequently added every other day Immunophenotype of Cells Cells were stained using antibodies in 100 mL FACS Buffer (2% FBS, 0.1% Sodium Azide) for 30 minutes at 4° C. Acquisition was performed using FACSCalibur (BD Bioscience) and analyzed using FCS Express 3.00.0612

Chromium Release Assay

T cells were evaluated for their cytotoxicity in a standard 4-hour chromium release assay using $^{51}$Cr-labeled target cells. T cells were plated in triplicate at $1\times10^5$, $0.5\times10^5$, $0.25\times10^5$, $0.125\times10^5$ bottom plate (Costar). After incubation, 50 μL of supernatant was harvested onto LumaPlate (Perkin Elmer), read in TopCount NXT (Perkin Elmer) and percent specific lysis was calculated per:

$$\frac{\text{Experimental } ^{51}Cr \text{ released} - \text{Spontaneous } ^{51}Cr \text{ released}}{\text{Maximum } ^{51}Cr \text{ released} - \text{Spontaneous } ^{51}Cr \text{ released}} \times 100$$

Spontaneous and maximum release was determined by measuring chromium in the conditioned supernatant from target cells incubated with CM or 0.1% Triton X-100 (Sigma), respectively and $0.0625\times10^5$ cells/well with $5\times10^3$ target cells in a 96-well V (Manufacturee Novo Software, Thornhill, Ontario, Canada).

Example 2

Generation of $CD19^+$ CAR

A CD19+ CAR was generated using the methods described above in Example 1 (referred to as the "EZ" method). These $CD19^+$ CAR (CD19CAR) were compared to a clinical grade ("CG") CD19CAR generated via a previous method.

Figure 2B:
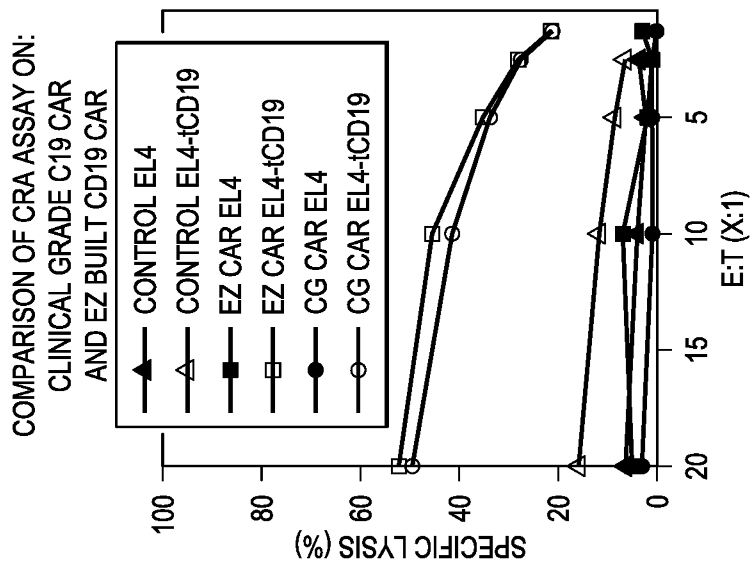
FIGS. 2A-B.
Figure 2A:
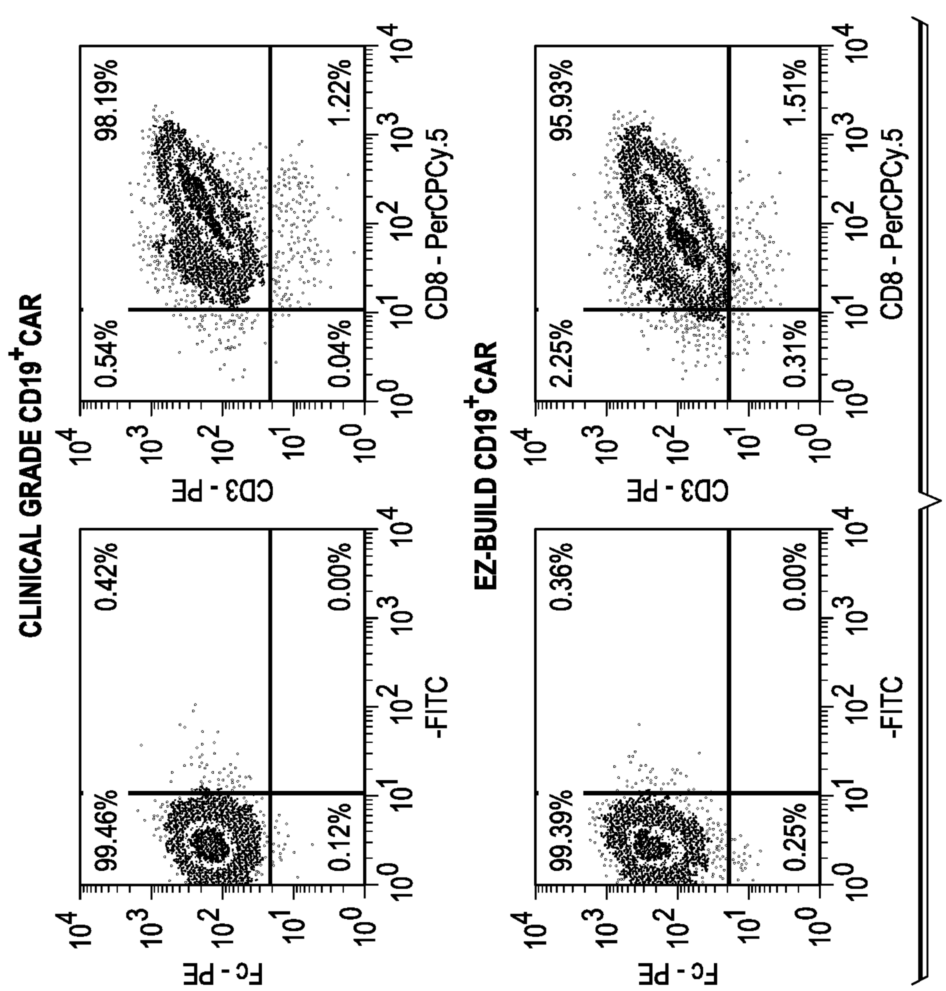

The data showed that the triple site-recombination system generated a CD19CAR (EZ) similar to the clinical grade CD19CAR (CG). The footprints left by recombination-sites in the plasmids did not interfere in the expression and function of the CAR (FIGS. 2A-B).

Example 3

Generation of CAR Containing (CD8, CD28) Transmembrane Domains and (CD28, 4-1BB) Signaling Domains Various CARs tested have shown similar expansion, cytotoxicity, and Th1 cytotoxicity. CD19-BB-z has shown lower production of Th2 cytokines; in vivo, it was efficient in controlling disease in mice (Molecular Therapy 17 (8): 1453-1464, 2009). Nonetheless, a concern exists due to the fact that cells persisted in vitro without antigenic stimulation.

CARs in the clinic are shown below in Table 2. In some embodiments, a CAR of the present invention does not have the specific construct as shown in the below Table 2. Alternately, in some embodiments, methods of the present invention may be used to generate another variation of a CAR having the characteristics of the CAR mentioned below in Table 2 that is nonetheless distinct from the CAR currently being used in the clinic.

TABLE 2

CARs in the Clinic

| Clinical Trial | UPenn | Cooper (MDACC) |
|---|---|---|
| Gene Transfer Method | Lentivirus | Electroporation/ Sleeping Beauty |
| scfv derived from | FMC63 | FMC63 |
| Scaffold | CD8alpha | IgG4 |
| Space region | 69 aa | 230 aa |
| Transmembrane | CD8alpha | CD28 |
| CAR signaling endomain(s) | CD137 and CD3-zeta | CD28 and CD3-zeta |
| Culture Method | CD3/CD28 beads | K562 aAPC |
| Cytokine | IL-2 | IL-2 and IL-21 |
| Culture Time | 14 days | 28 days |
| Transgene Expression in product infused | 4-23% | >80% |

Figure 3:
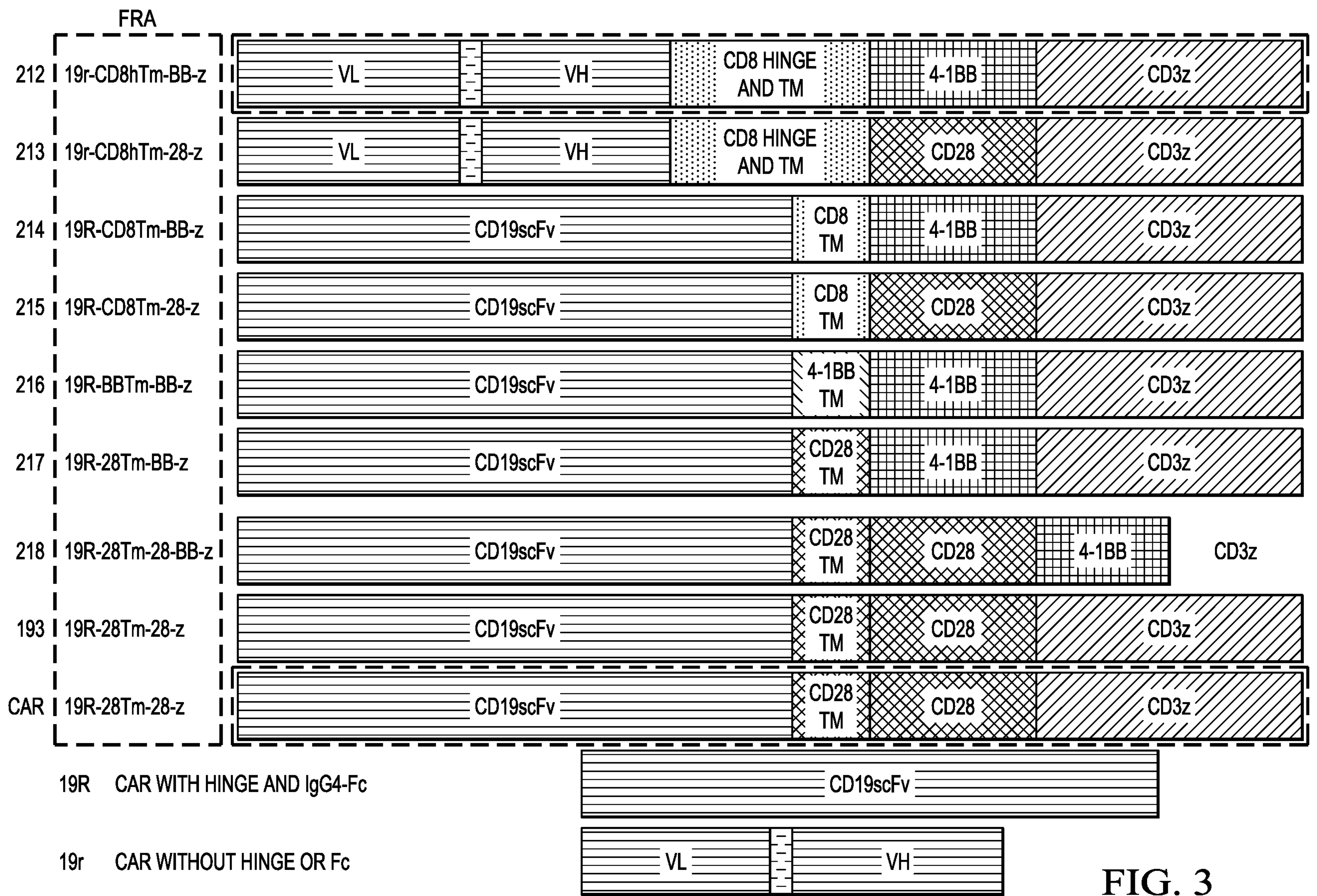
FIG. 3: CAR Designs. CAR 212=SEQ ID NO:4; CAR 213=SEQ ID NO:5; CAR 214=SEQ ID NO:56; CAR 215=SEQ ID NO:57; CAR 216=SEQ ID NO:58; CAR 217=SEQ ID NO:2; CAR 218=SEQ ID NO:59; CAR 193=SEQ ID NO:55.

Specific CAR construct designs are illustrated in FIG. 3. As shown in FIG. 3, a schematic of various CARs using a combination of CD19scfv, CD8a hinge or IgG4 Fc stalk, CD8 transmembrane (TM) or CD28 TM or CD137 TM and signaling through CD28 or CD137 endodomain along with CD3zeta endodomain were generated.

Figure 4:
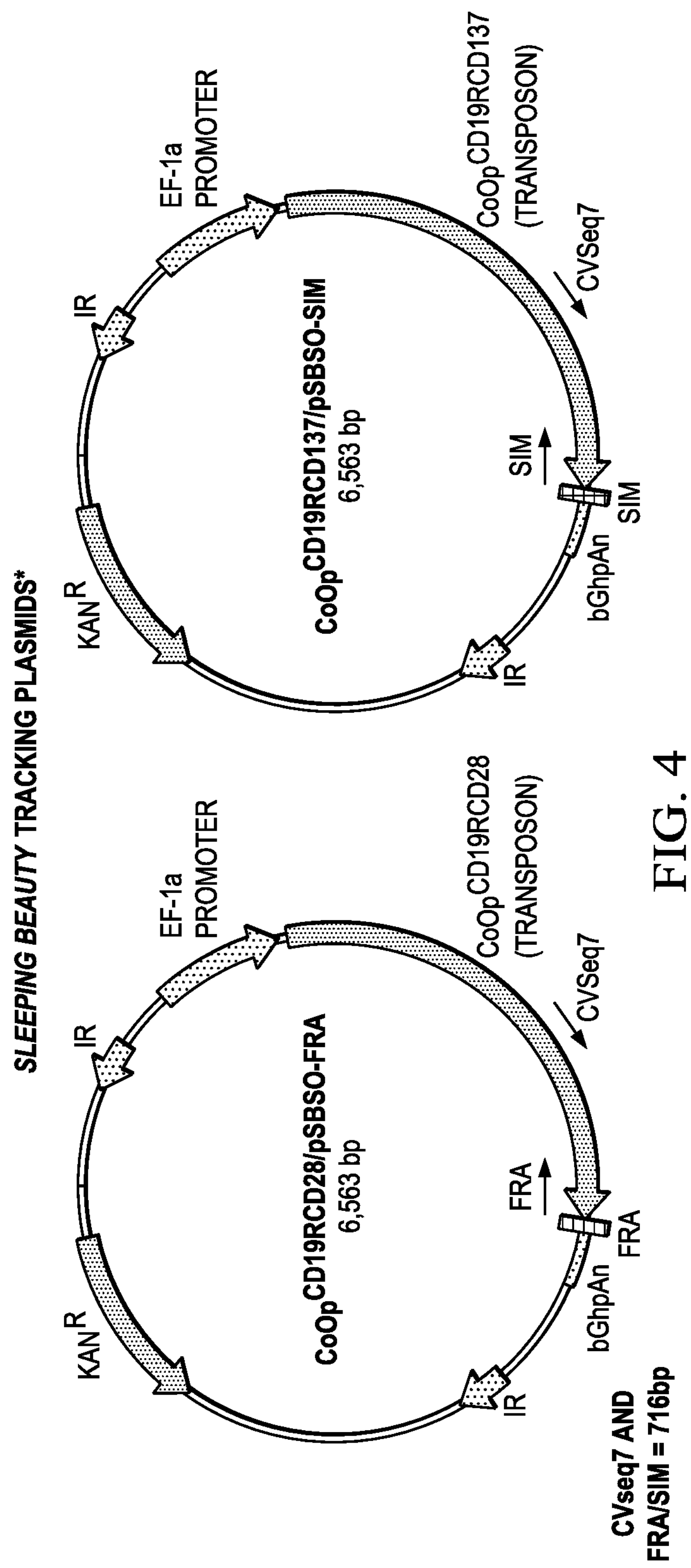
FIG. 4: Sleeping Beauty tracking plasmids

The CAR constructs shown in FIG. 3 were then cloned into Sleeping Beauty plasmids containing SIM and FRA tags to allow tracking in competitive repopulation studies, when amplified using a common CVseq7 primer. The Sleeping Beauty tracking plasmids are shown in FIG. 4.

Figure 5A:
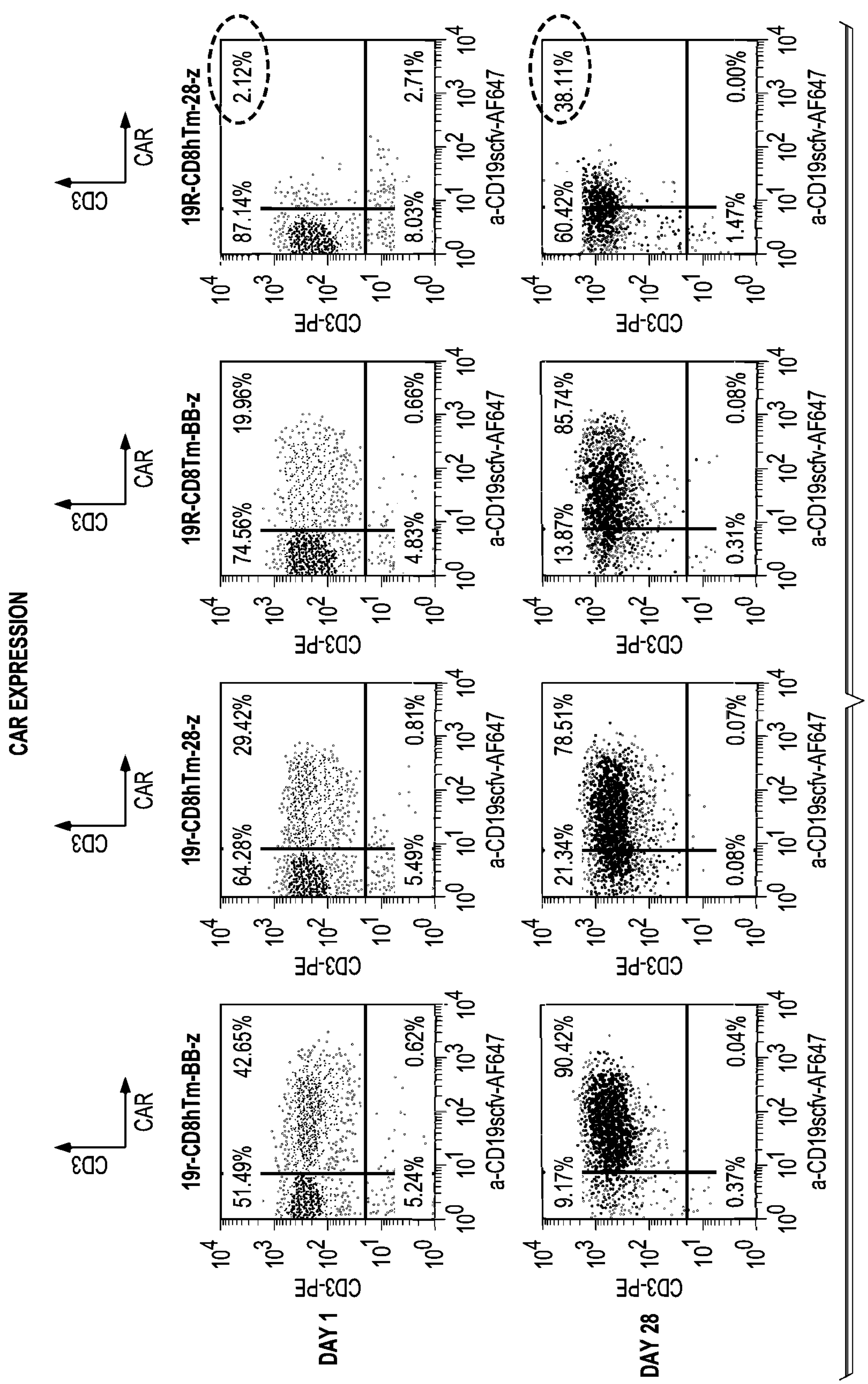
FIGS. 5A-B: CAR Expression.
Figure 5B:
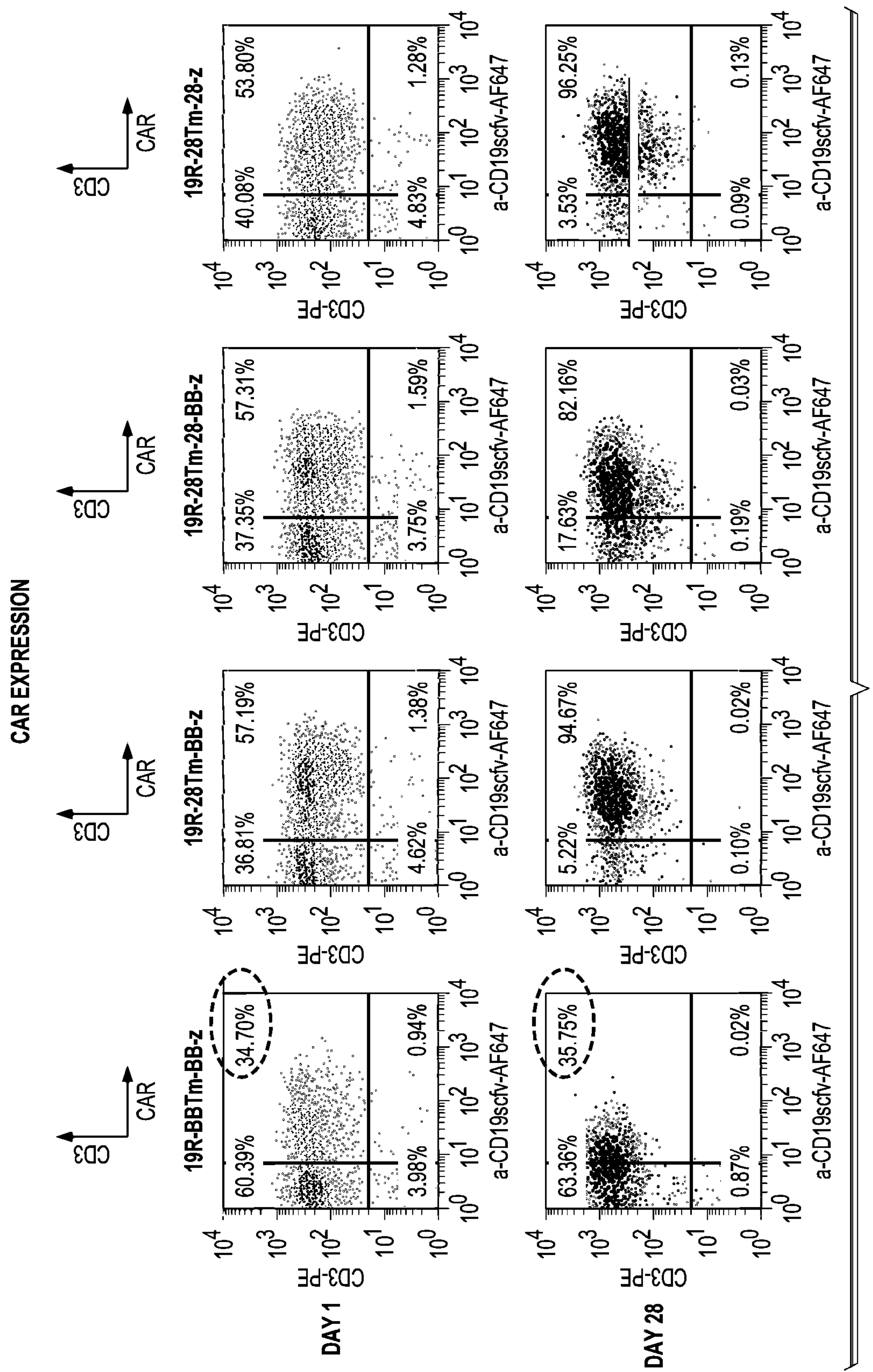

The CAR constructs shown in FIG. 3 were electroporated into T cells using Amaxa Nucleofector II and co-cultured with aAPC for 28 days in the presence of cytokines (IL2, IL-21). CAR expression the day after electroporation (day 1) and after 28 days of co-culture with aAPC (day 28) is shown. Dot-plots for CD3 and CAR are shown, where CD3 and anti-CD19scfv specific Ab was used to distinguish T cells and CAR. CAR expression results are shown in FIG. 5.

Figure 6:
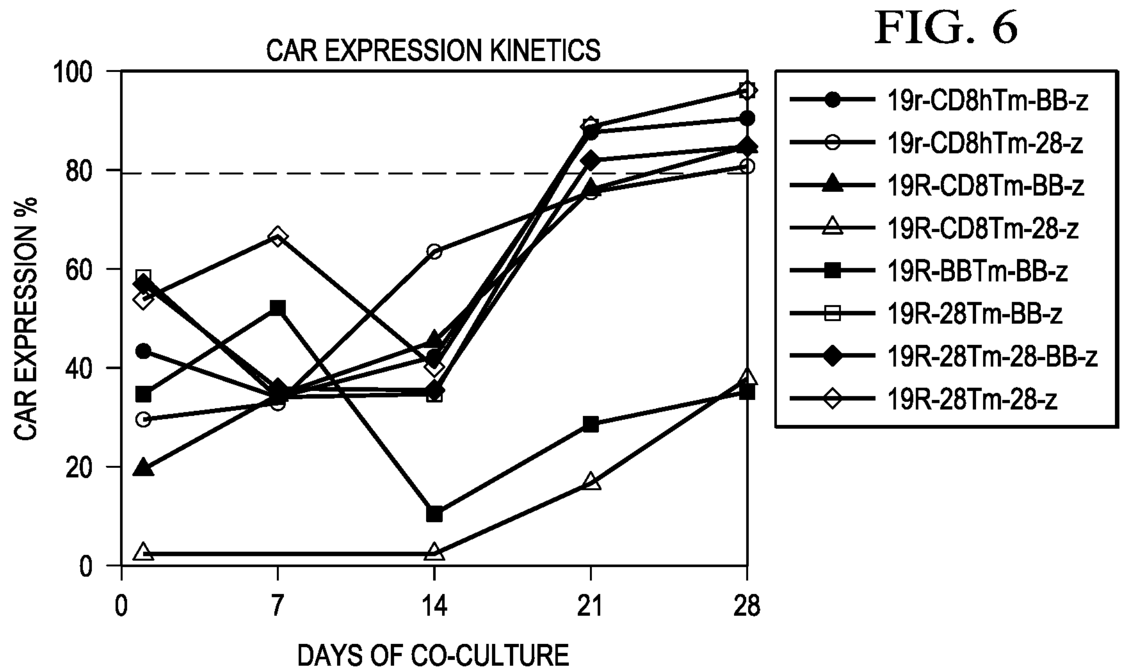
FIG. 6: CAR Expression Kinetics

The CAR constructs shown in FIG. 3 were evaluated for CAR expression over time for 28 days and is shown. After 21 days most of the cultures had >80% CAR expression. CAR expression kinetics are shown in FIG. 6.

Figure 7:
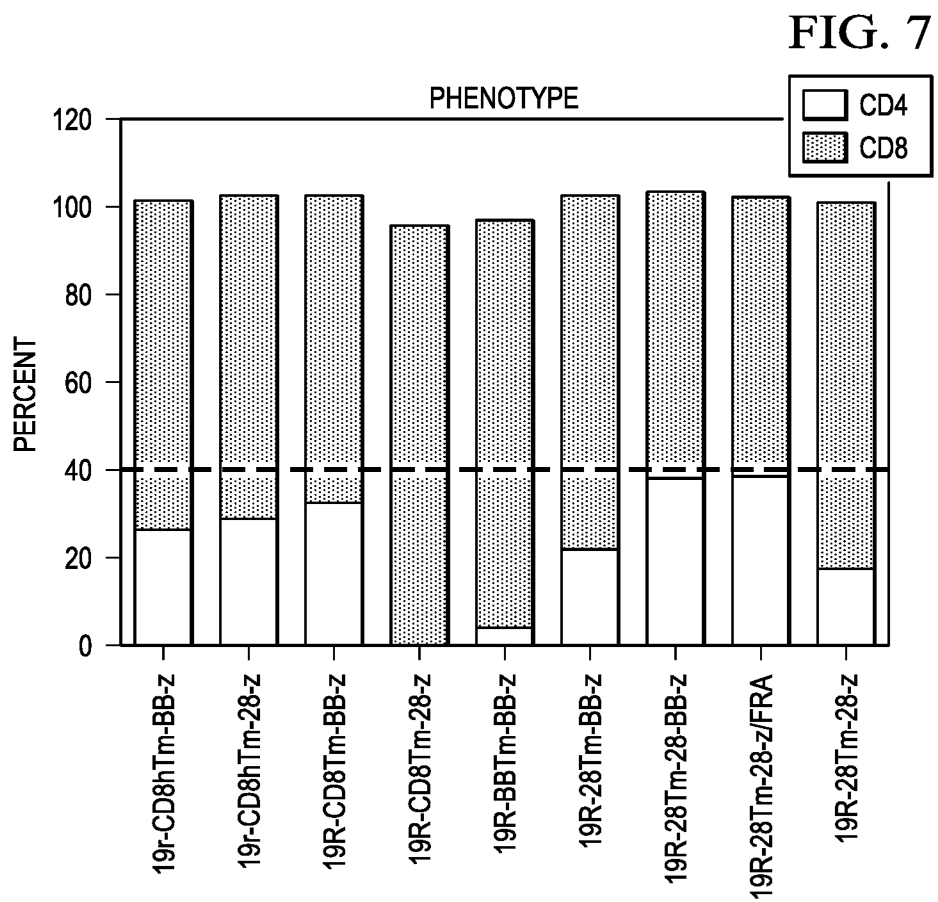
FIG. 7: Phenotype.

Percent expression of CD4 and $CD^+$ T cells in cultures nucleofected with CARs from FIG. 3 is shown after 28 days of co-culture with aAPC. These phenotype results are shown in FIG. 7.

Figure 8A:
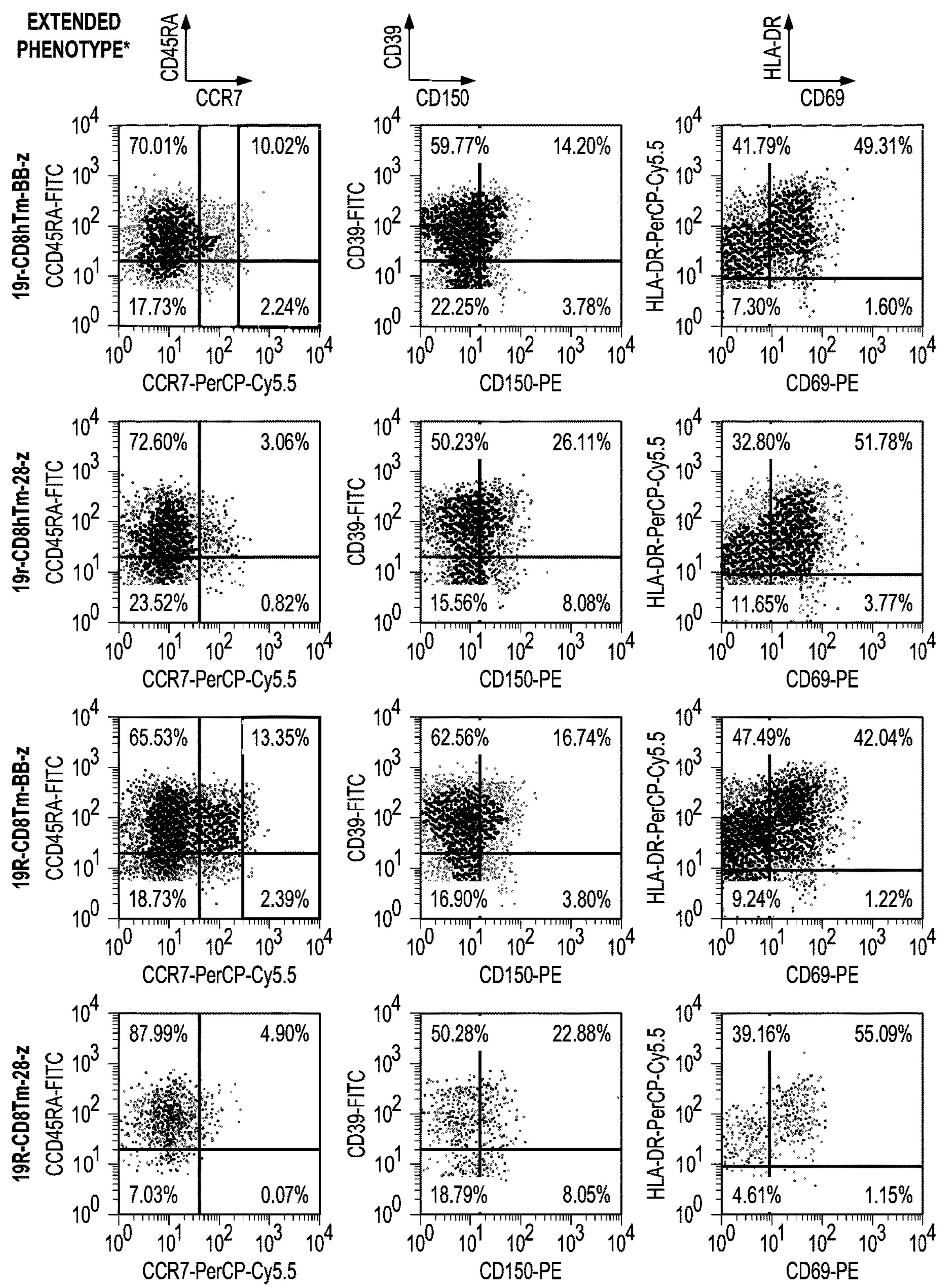
FIGS. 8A-D: Extended Phenotype is shown in FIG. 8A and FIG. 8B.
Figure 8B:
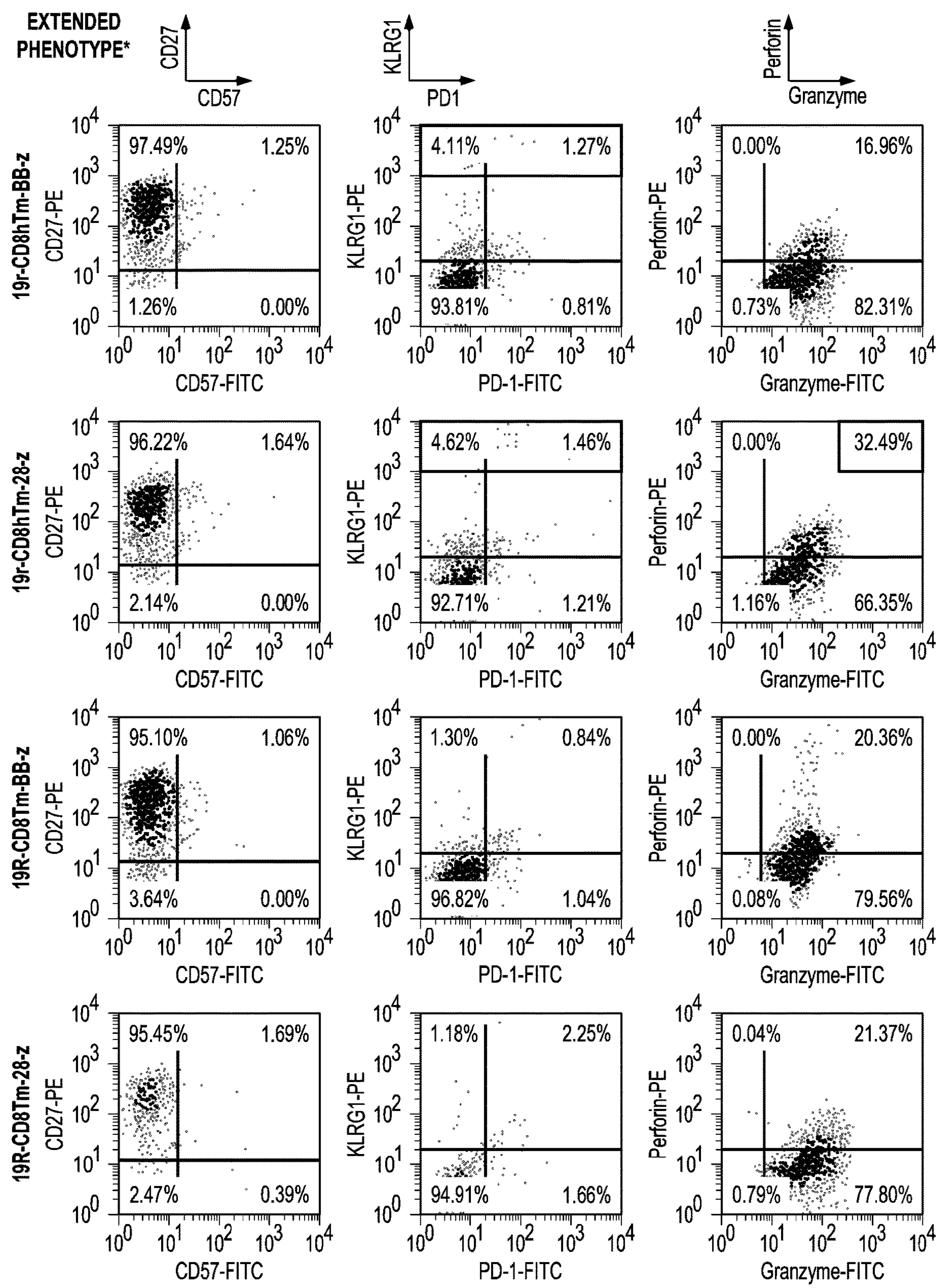
Figure 8C:
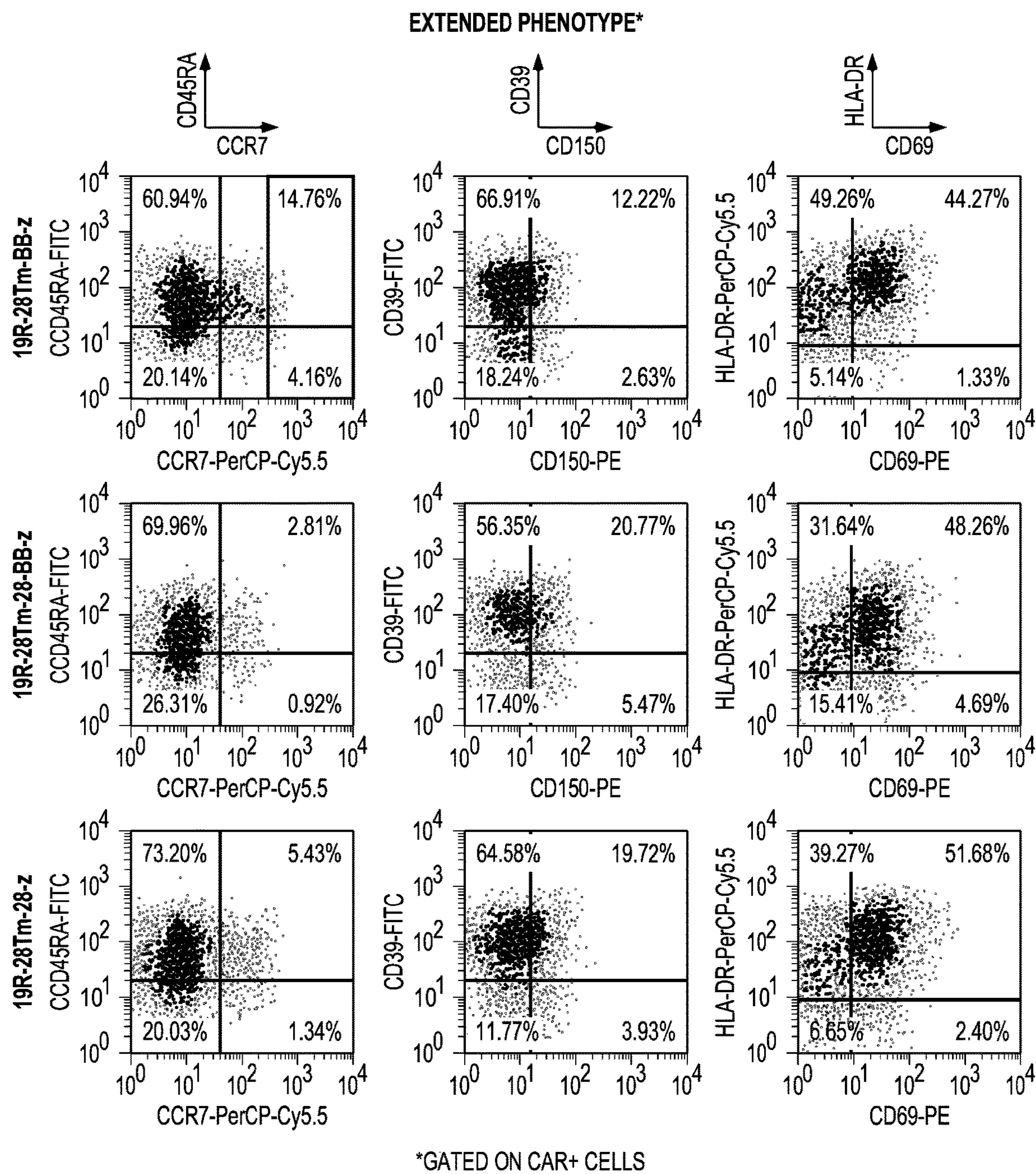
Figure 8D:
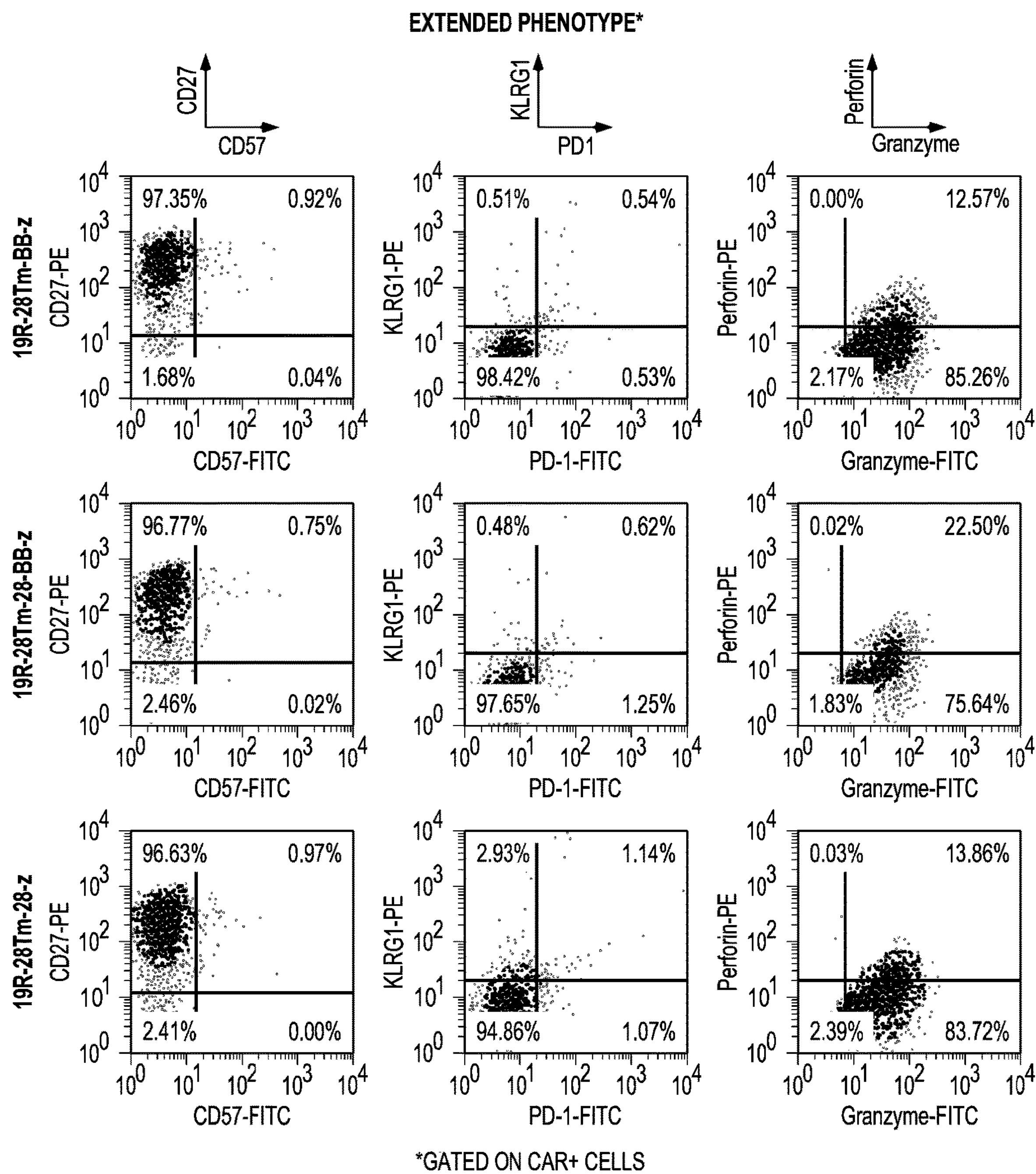

After 28 days of co-culture $CAR^+$ T cells (expressing the CAR described in FIG. 3) were evaluated for expression of markers pertaining to memory (CD45RA, CCR7, CD27), activation (CD69, HLA-DR), cytotoxic (Perforin, Granzyme B), exhaustion/senescence (CD57, KLRG1, PD1), and adhesion (CD39, CD150). Results for this extended phenotype are shoen in FIGS. 8A-B.

Figure 9:
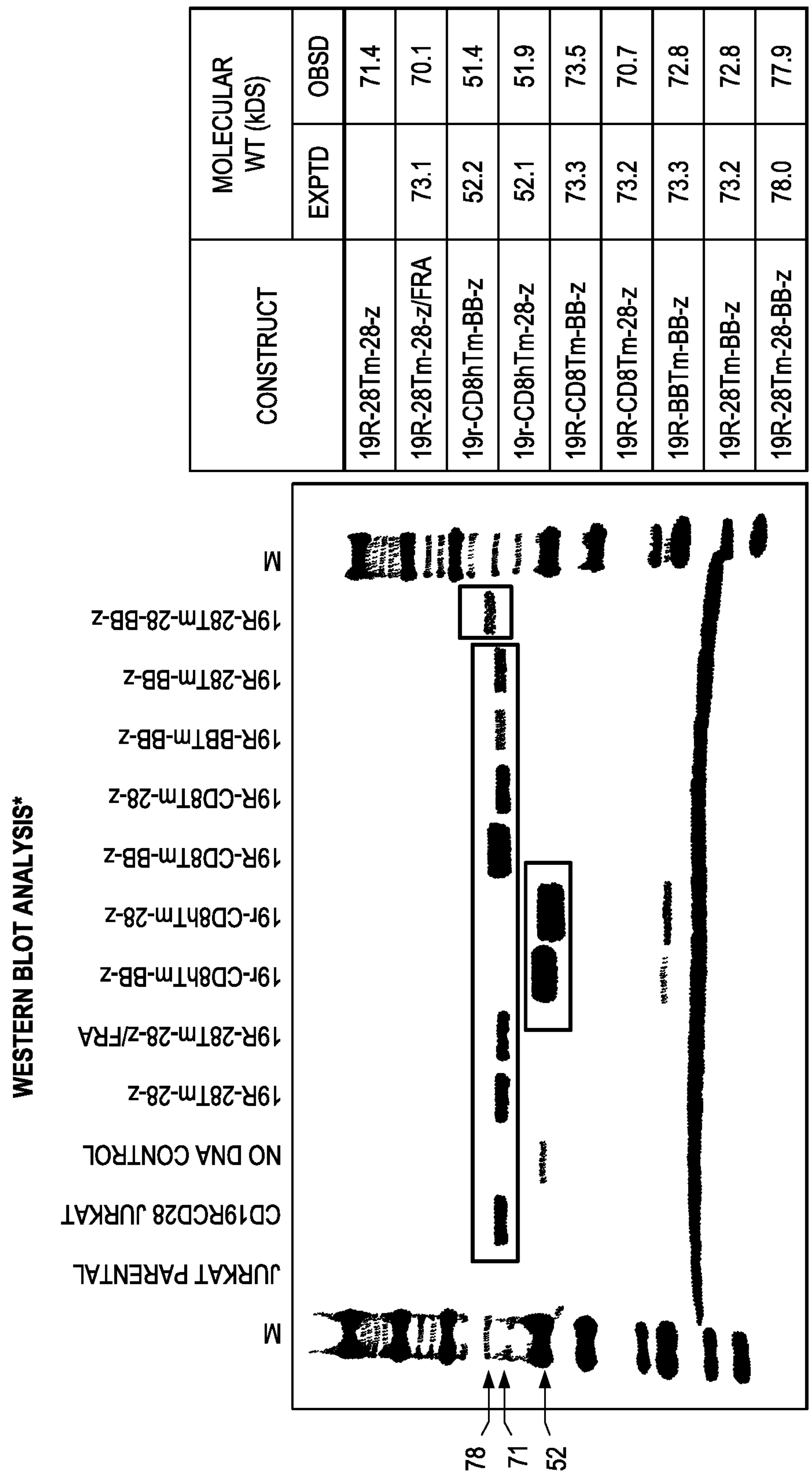
FIG. 9: Western Blot Analysis.

$CAR^+$ T cells (expressing the CAR described in FIG. 3) were evaluated for expression of CD3 ζ using western blot. Cell lysates were run under denaturing conditions, transferred and the expression of chimeric CD3 ζ was measured using a primary mouse anti-human CD3ζ mAb and HRP-conjugated goat anti-mouse IgG using SuperSignal West Femto Maximum Sensitivity substrate. Chimeric CD3ζ bands at 52, 71 and 78 kD are observed relative to size of CAR constructs. These western blot results are shown in FIG. 9.

Figure 10:
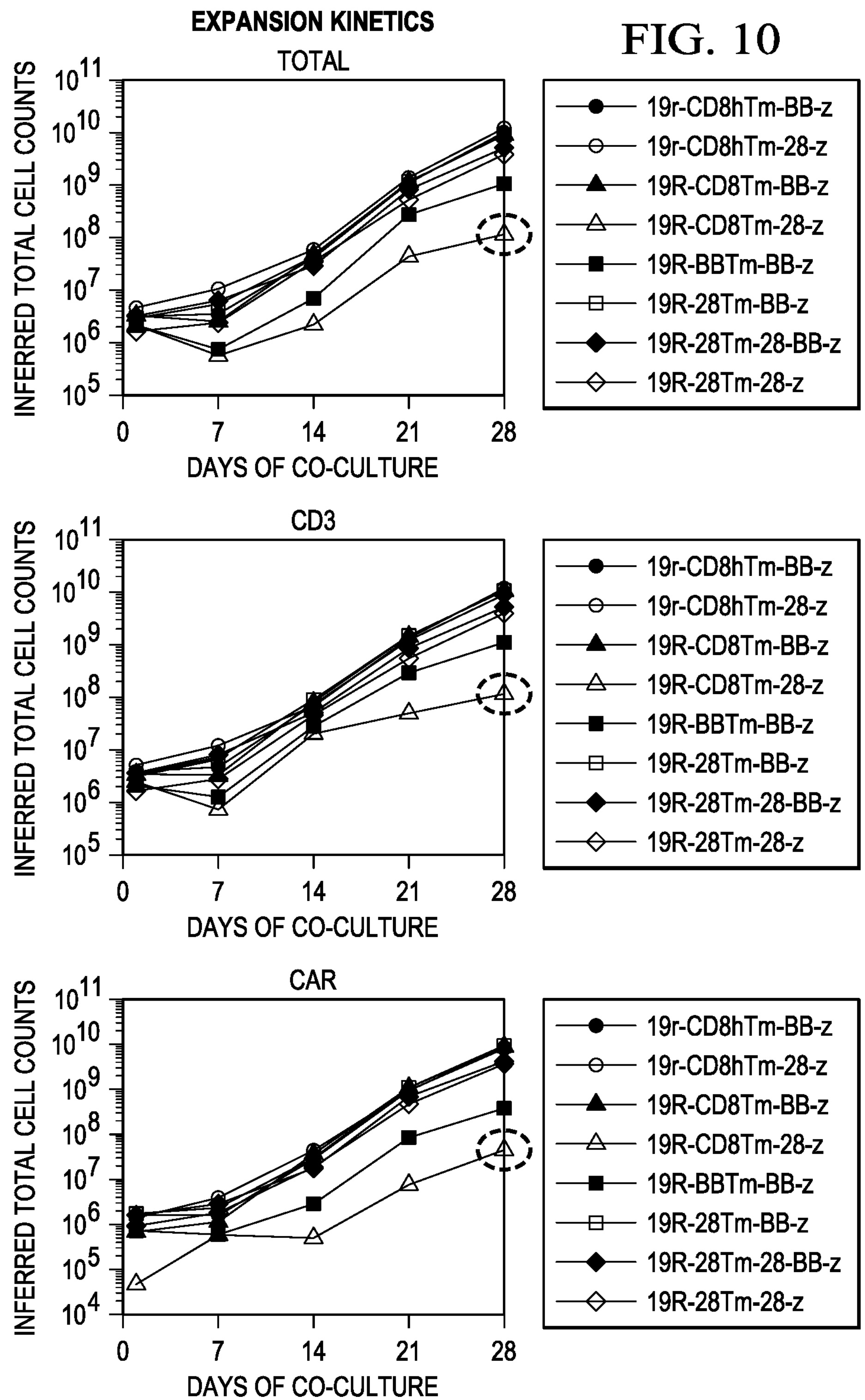
FIG. 10: Expansion Kinetics.

T cells electroporated with the CAR constructs (described in FIG. 3) were stimulated with K562 aAPC at day 1 and every 7 days thereafter for 28 days. At the end of each stimulation cycle, cells were counted using trypan blue exclusion method and phenotyped for CD3 and CAR expression. The graphs shown in FIG. 10 depict inferred cell counts for total, CD3ζ, and $CAR^+$ T cells over time.

Figure 11:
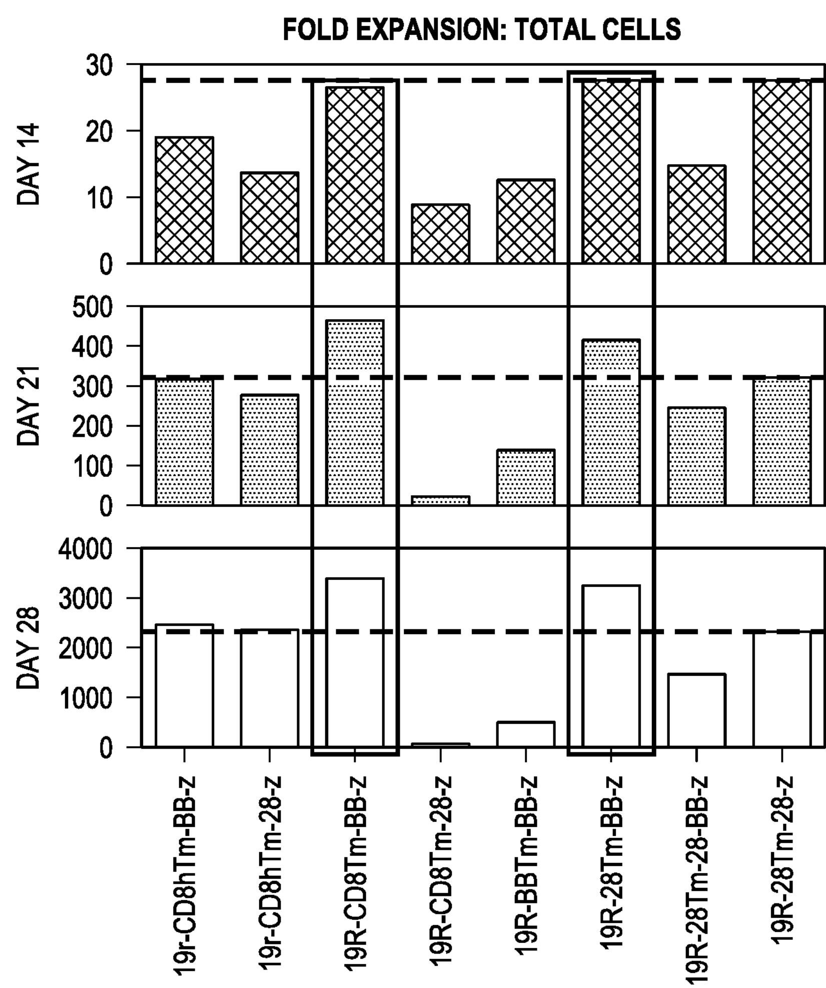
FIG. 11: Fold Expansion: Total Cells
Figure 12:
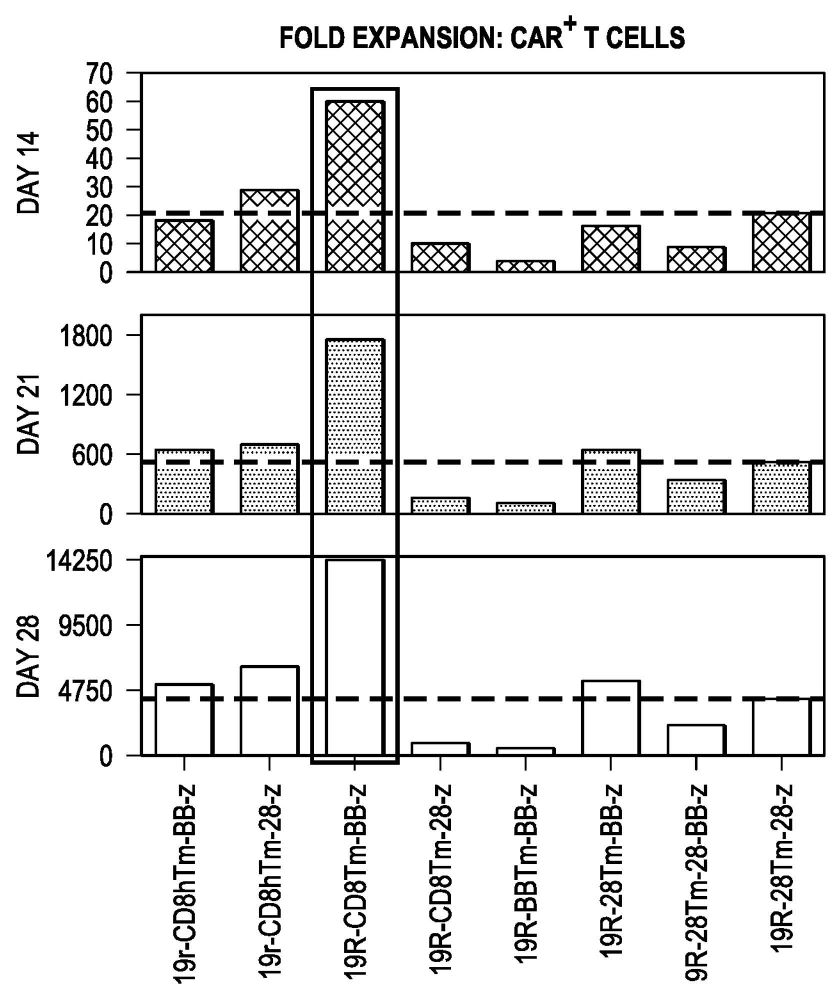
FIG. 12: Fold Expansion: CAR+ T cells.
Figure 13:
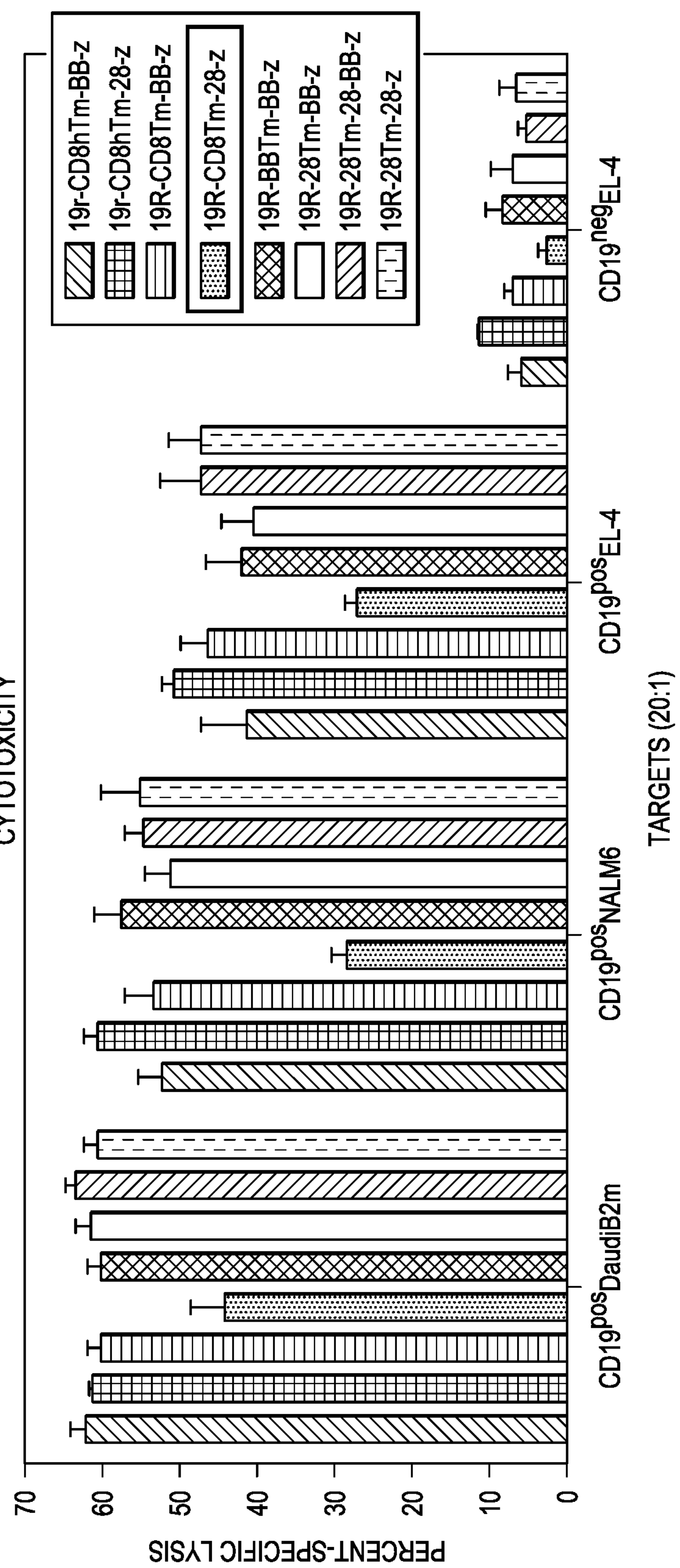
FIG. 13: Cytotoxicity.
Figure 14:
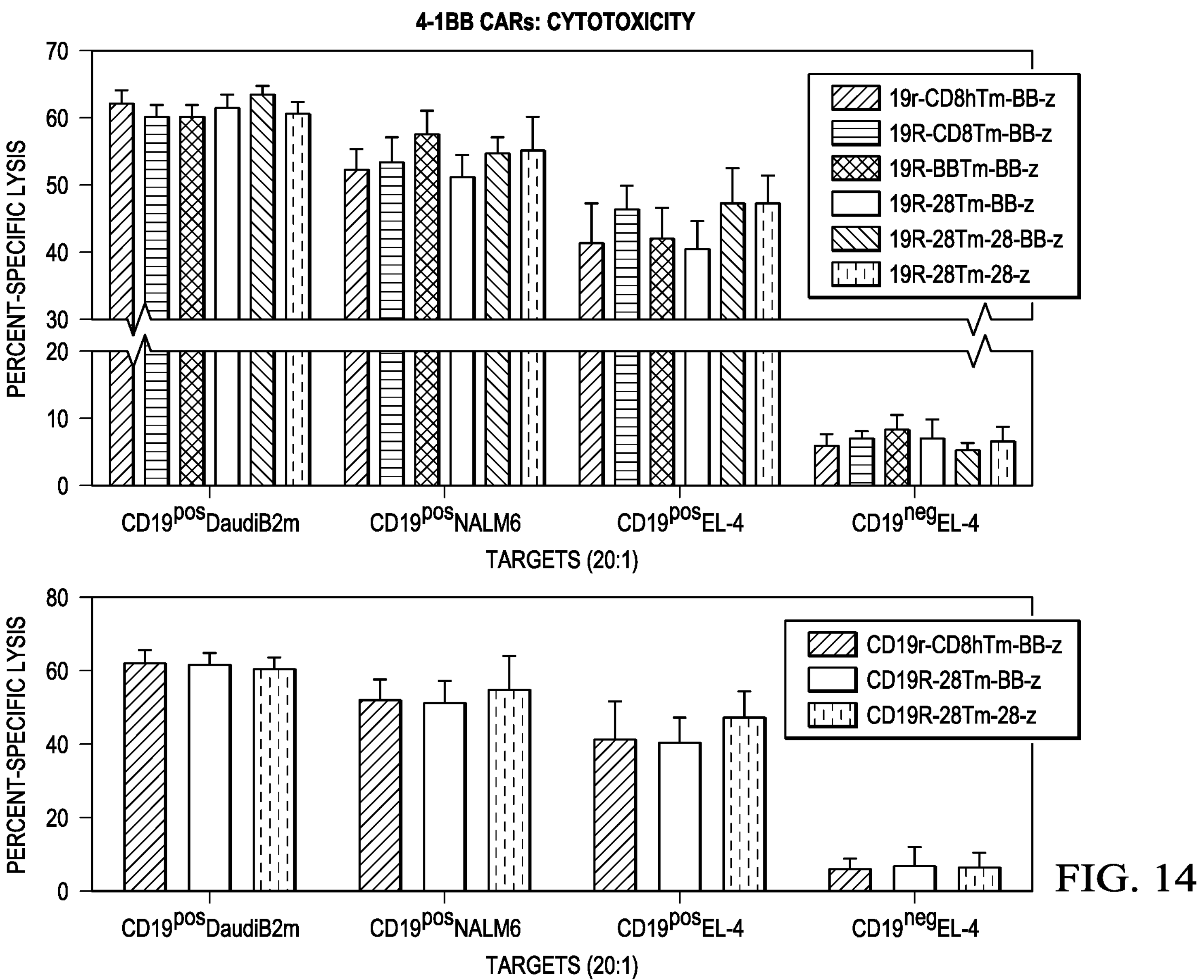
FIG. 14: 4-1BB CARs: Cytotoxicity.
Figure 15:
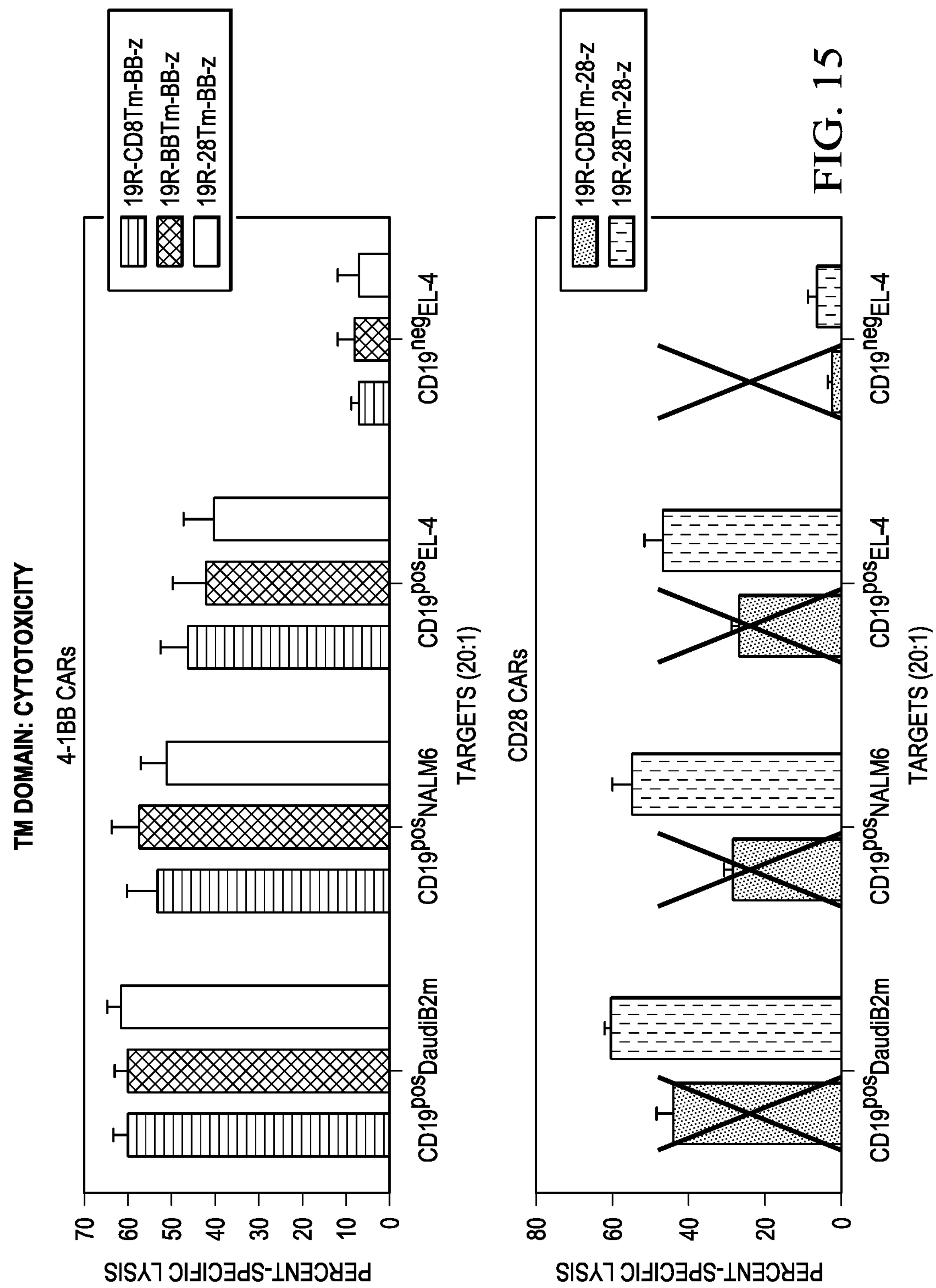
FIG. 15: TM domain: Cytotoxicity.
Figure 16:
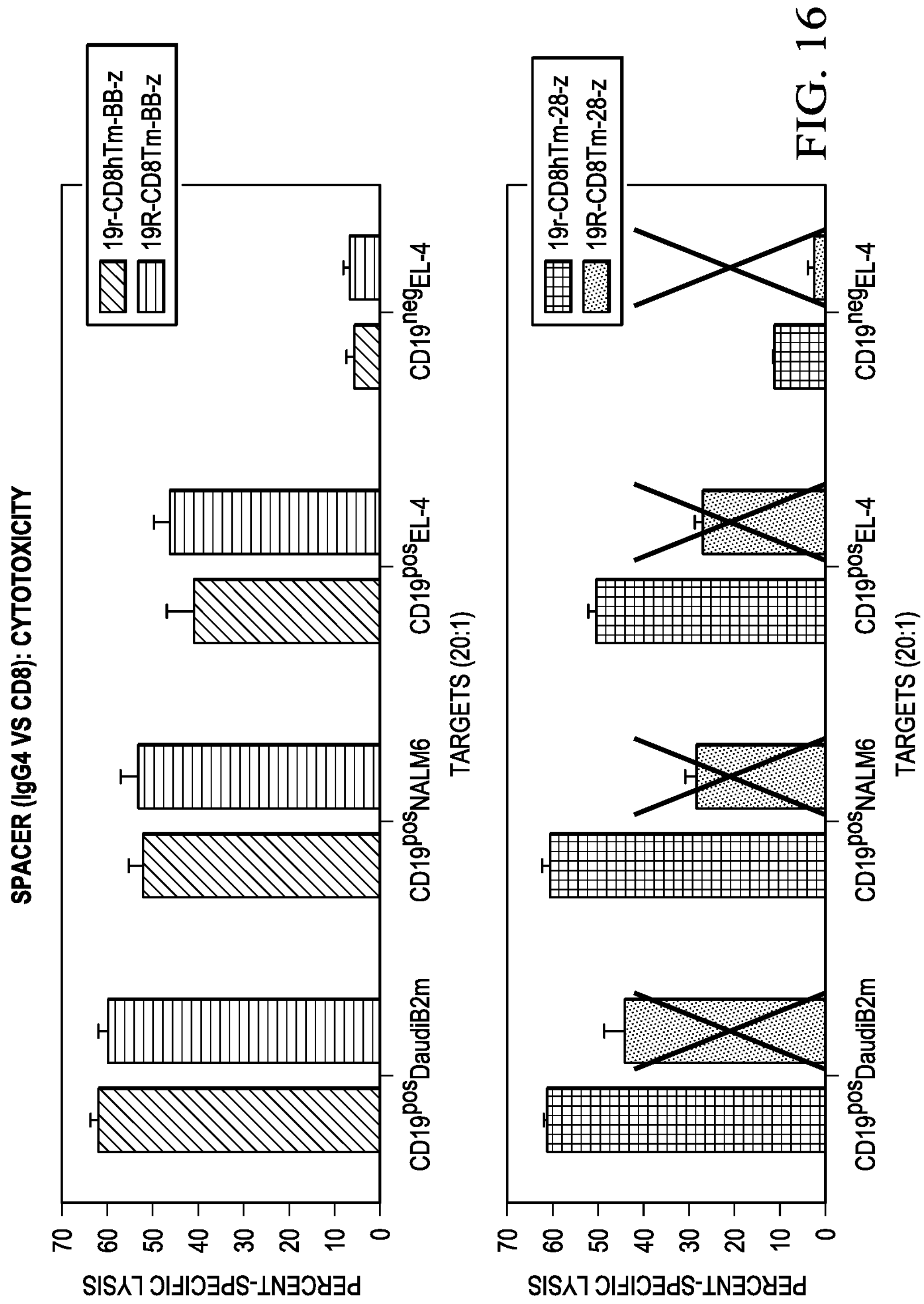
FIG. 16: Spacer (IgG4 vs CD8): Cytotoxicity
Figure 17:
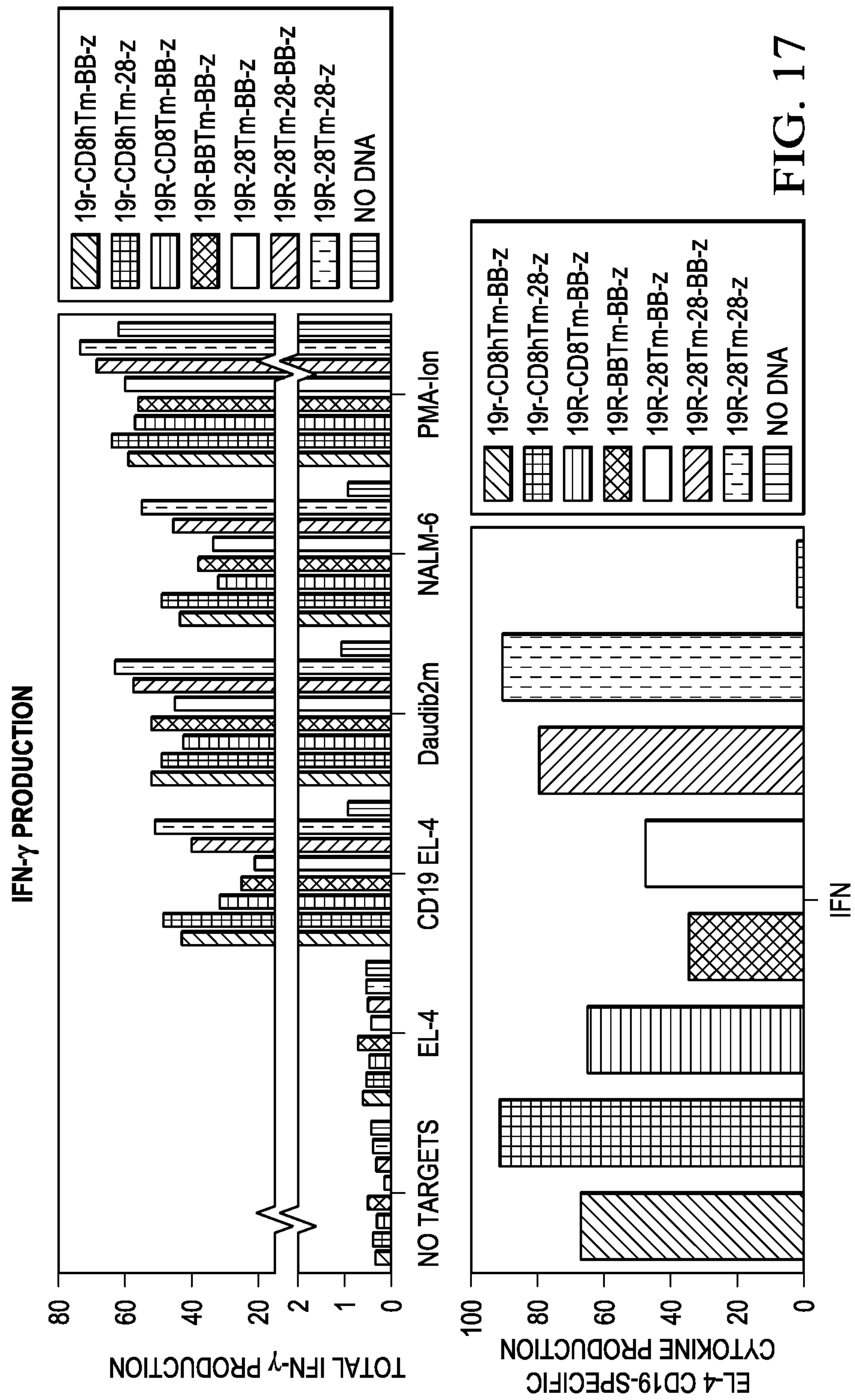
FIG. 17: IFN-γ production.
Figure 18:
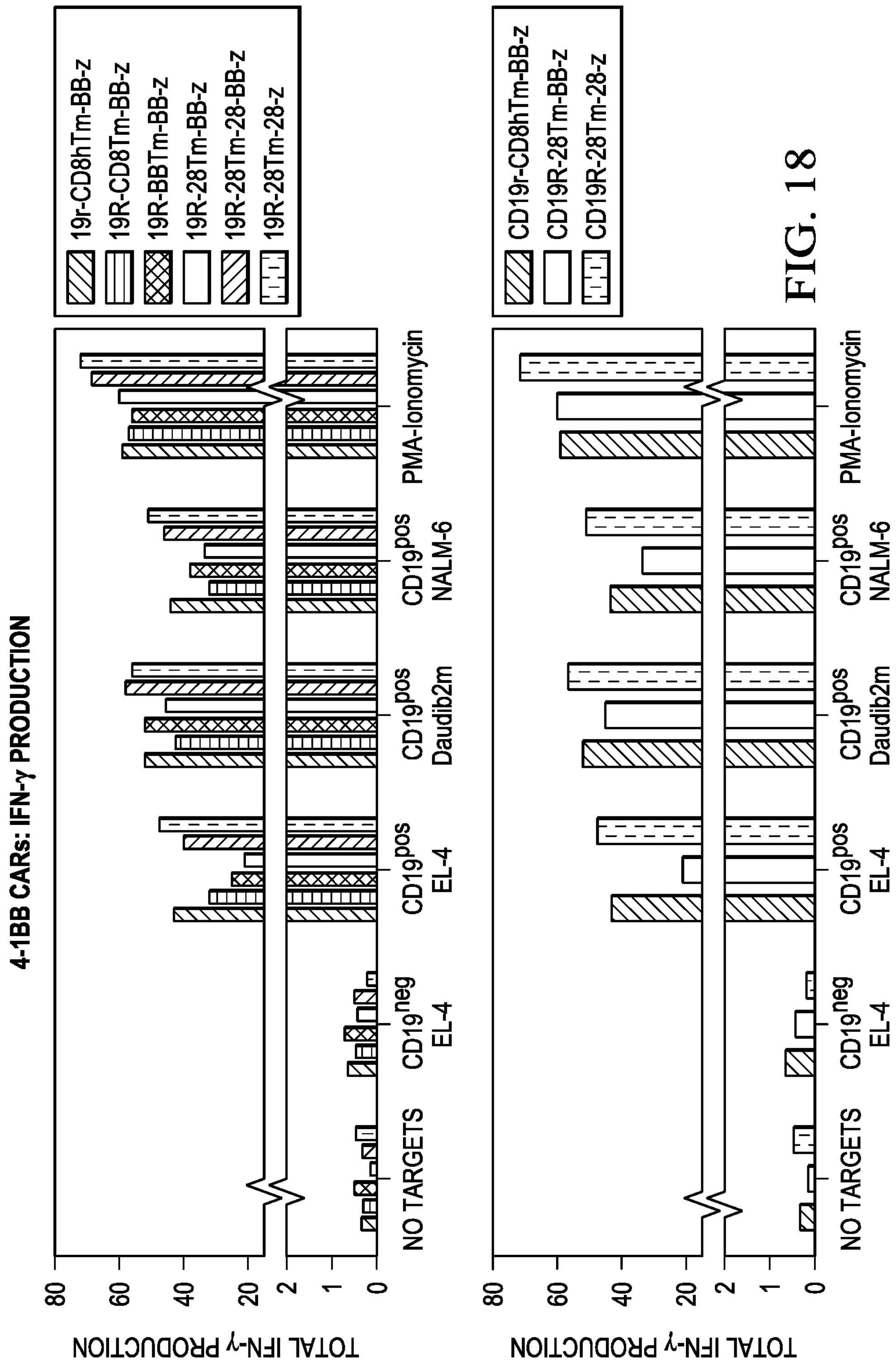
FIG. 18: 4-1BB CARs: IFN-γ production
Figure 19:
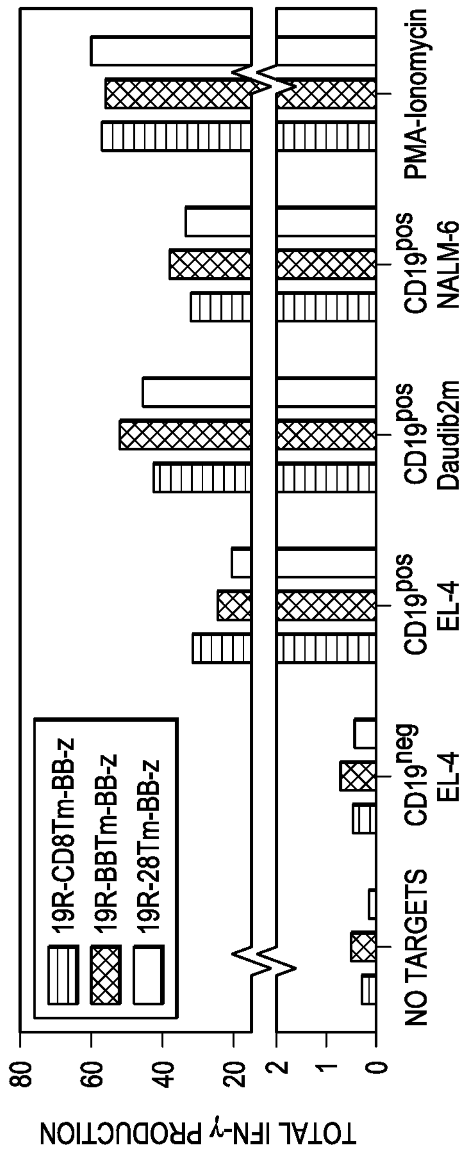
FIG. 19: TM domain: IFN-γ production
Figure 20:
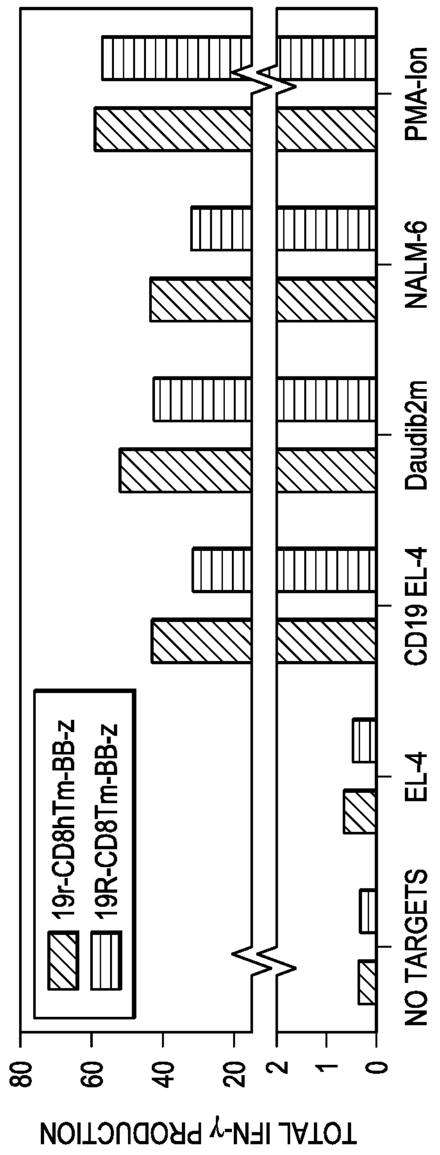
FIG. 20: Spacer (IgG4 vs CD8): IFN-γ production.

Expansion of cells was measured. Fold expansion for Total Cells (FIG. 11) and $CAR^+$ (FIG. 12) T cells was calculated at day 14, 21 and 28 days of co-culture by comparing counts to day 1 (post electroporation). Results are shown in FIG. 11 and FIG. 12.

Cytotoxicity was measured for the CAR-expressing T Cells ($CAR^+$ T cells). $CAR^+$ T cells (expressing CAR described in FIG. 3) were evaluated for their cytotoxicity against $CD19^+$ tumor targets (Daudi$\beta_2$m, NALM-6 and $CD19^+$ EL-4) as compared to $CD19^{neg}$ EL-4 in a standard 4-hr chromium release assay. Results are shown in FIG. 13, FIG. 14, FIG. 15, and FIG. 16.

Intracellular IFN-γ production. $CAR^+$ T cells (expressing the constructs described in FIG. 3) were incubated with ($CD19^+$ and $CD19^{neg}$) stimulator cells in the presence of protein transport inhibitor for 4-6 hr, fixed, permeabilized and stained with IFN-γ specific mAb. PMA-Ionomycin was used as a positive control. Results for intracellular IFN-γ production are shown in FIG. 17, FIG. 18, FIG. 19, and FIG. 20.

Figure 21:
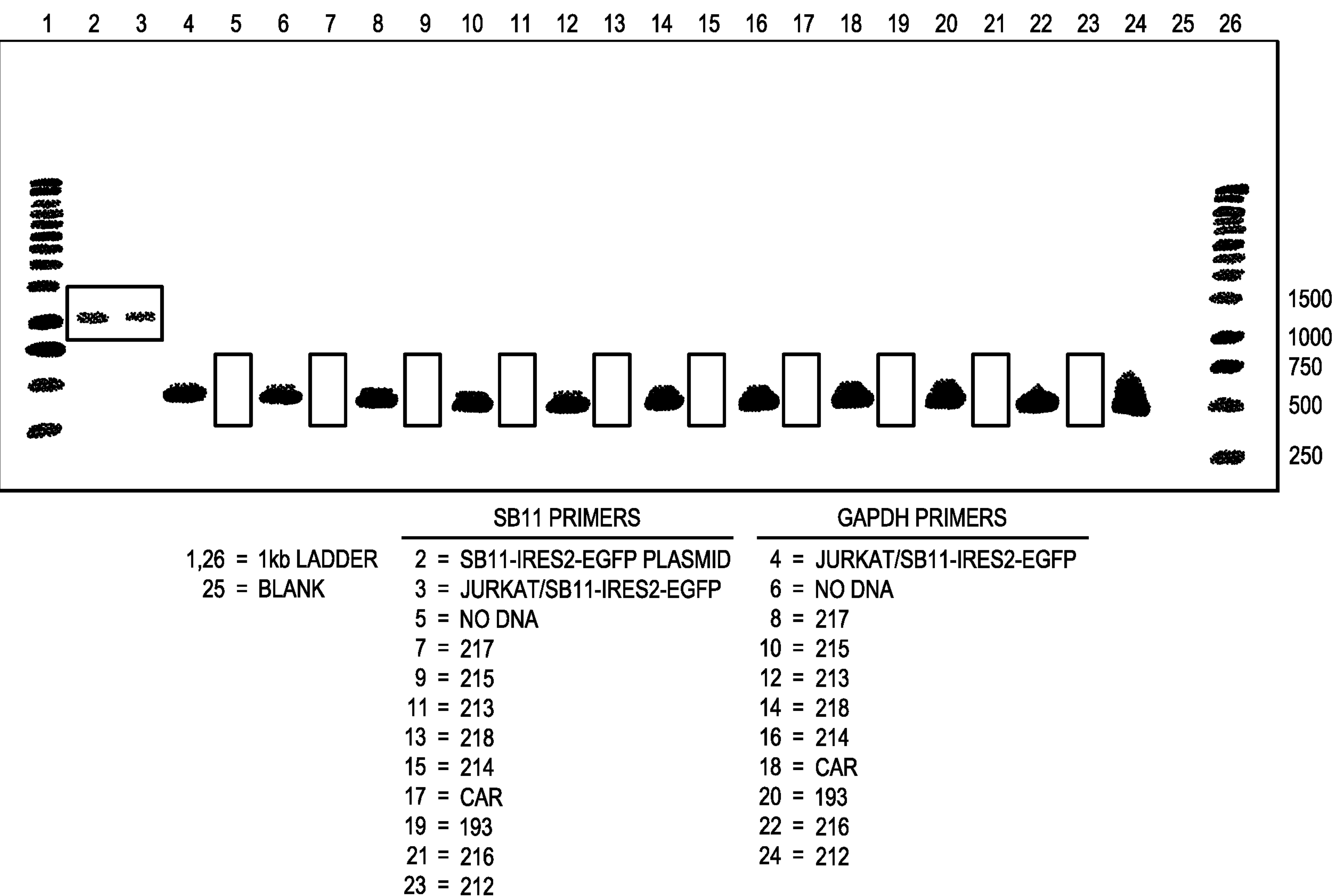
FIG. 21: Safety: PCR for SB11 transposase.

PCR for SB11 transposase. DNA isolated from CAR+ T cells (FIG. 3) was amplified using SB11 specific primers in a thermal cycler. GAPDH was used as the housekeeping gene, and linearized pCMV-SB11 plasmid, genomic DNA from Jurkat cells expressing SB11 were used as positive controls. CAR' cells (No DNA) were used as negative controls. These PCR results are shown in FIG. 21.

Figure 22:
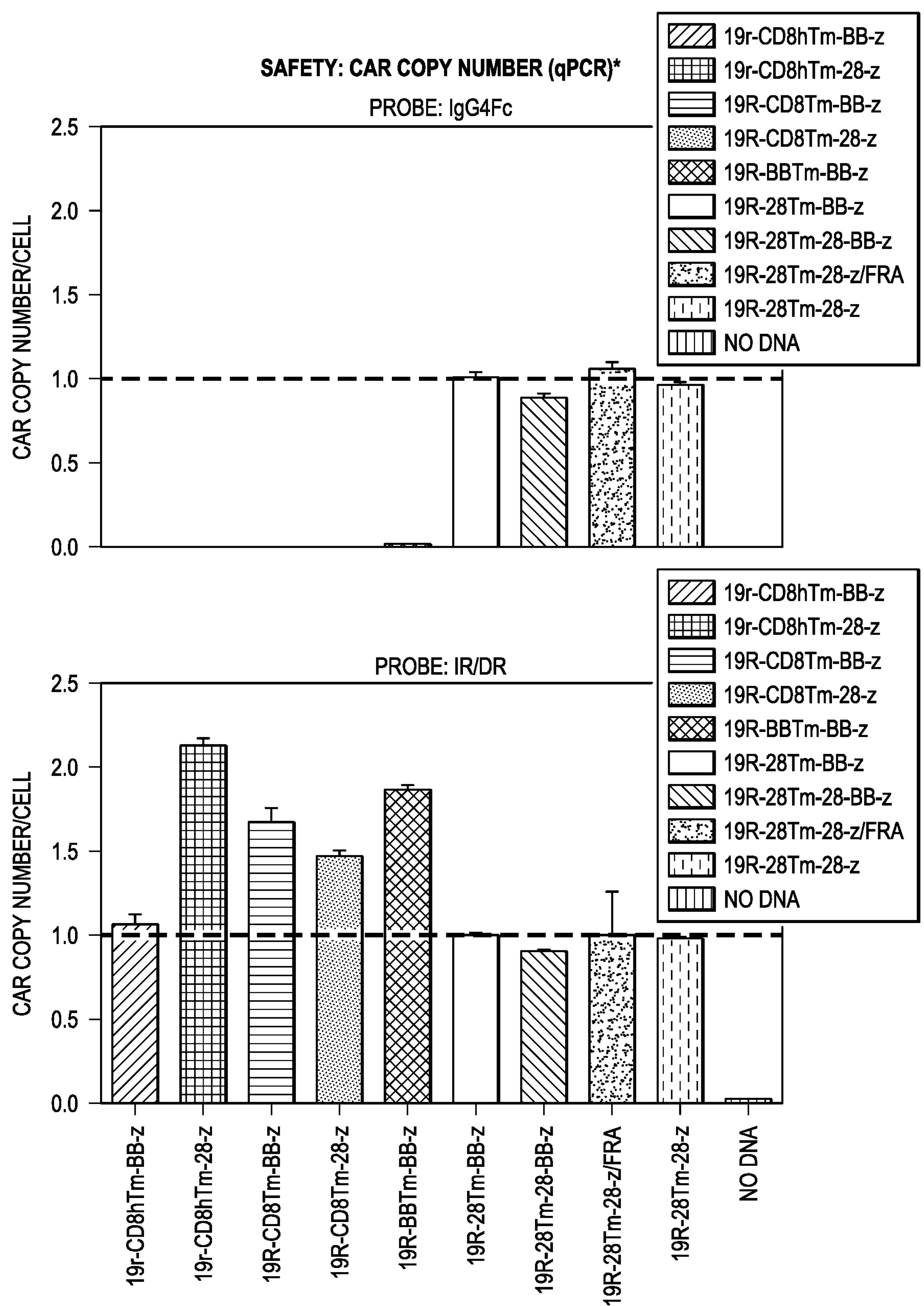
FIG. 22: Safety: CAR copy number (qPCR).

CAR copy number was measured using quantitative PCR (qPCR). The integrated number of CAR transgene in cells (of the CAR constructs shown in FIG. 3) were evaluated by amplifying genomic DNA using primers and probes specific for the IgG4 Fc stalk and inverted/direct repeats (IR/DR). RNAse P gene was used as an internal control, and the Jurkat cell line expressing a single copy of CAR was used to generate a standard curve. Results are shown in FIG. 22.

Figure 23:
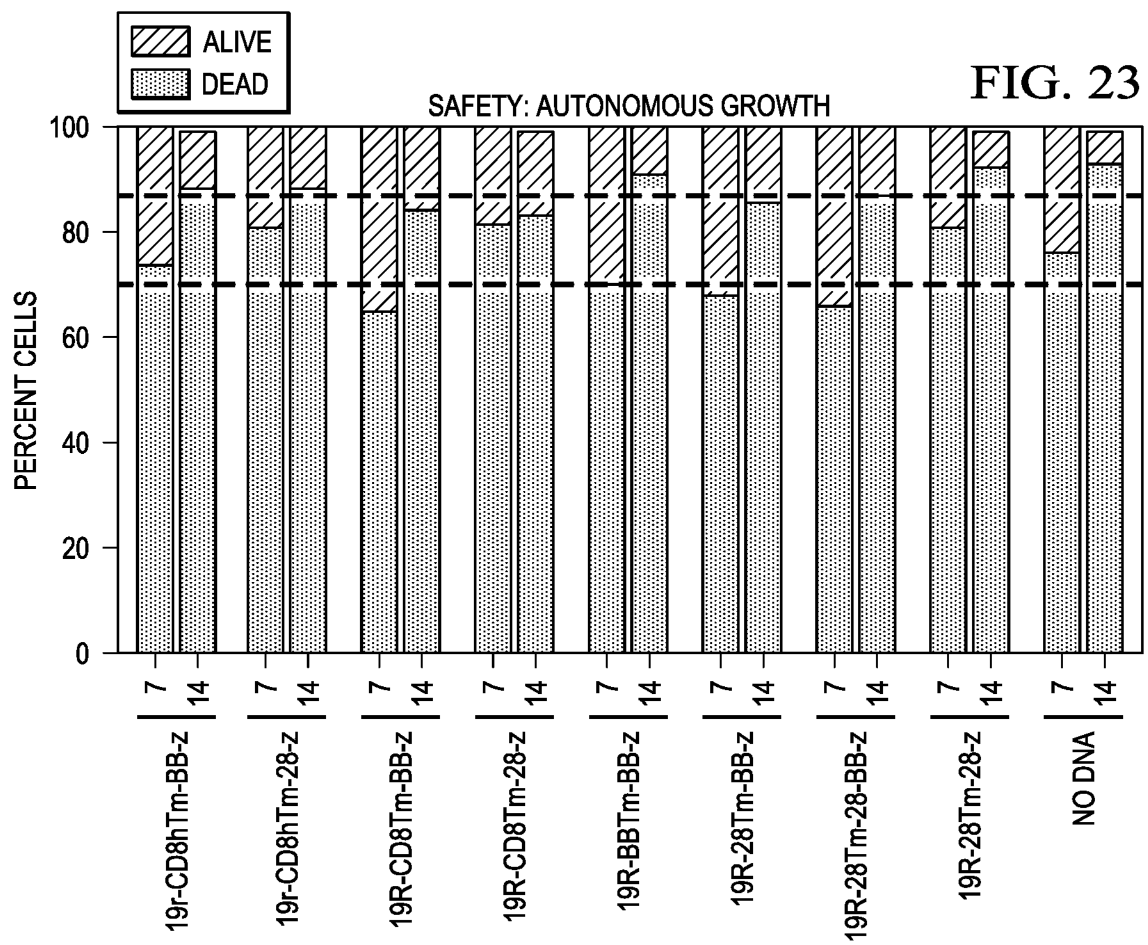
FIG. 23: Safety: Autonomous Growth. As shown in the figure, a lack of autonomous growth was observed.

Next, CAR+ T cells were measured for the presence or absence of autonomous growth. Aberrant growth of CAR+ T cells (expressing CAR constructs shown in FIG. 3) was monitored and measured by culturing T cells in the absence of cytokines and aAPC. Cells were counted every 7 days and the percents alive/dead cells (from day 1) were calculated and plotted. As shown in FIG. 23, more than 80% of T cells were observed to be dead by day 14 showing lack of autonomous growth.

Various CARs could be expressed (>80%), expanded (~1010) and were cytotoxic (~60%, Daudi) to similar extend. Scaffolding domains (IgG4 or CD8α) were used to build CAR and didn't effect expression or potency. Transmembrane domains (CD8, CD28) did not affect potency. 4-1BB transmembrane domain (216) affected expression (anti-scFv Ab), but not cytoxicity and cytokine production. Combination of signaling domains, CD28 and 4-1BB did not have an additive effect. CAR+ T cells exhibited memory/effector phenotype. CARs containing only 4-1BB domain (212, 214, 217) had higher CCR7 expression as compared to others. Cells expressed markers for memory (CD27hi, CD45RAhi, CCR7lo), activation (CD69med, HLA-DRhi), cytolysis (granzymehi, perforinlo), and adhesion (CD39hi, CD150lo), but negligible amounts of inhibitory markers (CD57, PD1, KLRG1) were observed. All the CARs including the ones containing 4-1BB domain lacked SB11 transposase and did not auto-proliferate.

Example 4

Generation of CAR Containing CD3-Zeta

Figure 24:
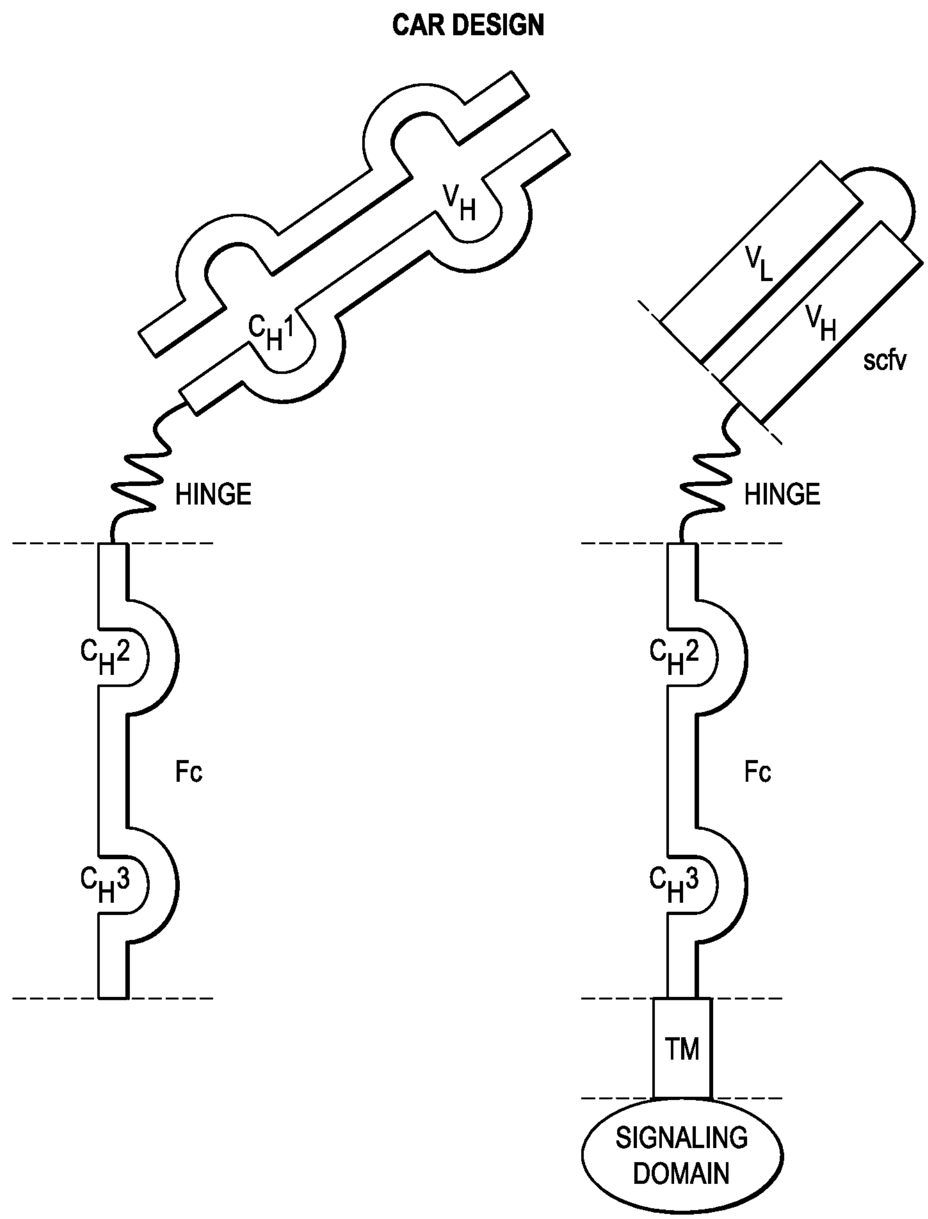
FIG. 24: CAR design. An example of a CAR is provided on the right-hand side of the figure.

CAR containing CD3ζ are provided in this example. A general diagram of CAR design is shown in FIG. 24. As shown in FIG. 24, a comparison of CAR design (FIG. 24, right) with an antibody molecule (FIG. 24, left) are shown.

CD3ζ sequences are shown in FIG. 25. The sequence of CD3zeta and its isoform are shown in FIG. 25. The CAR designs included CD3 zeta (isoform 1) which forms one of the endodomain signaling moieties and has three ITAMs.

Figures 26, 27:
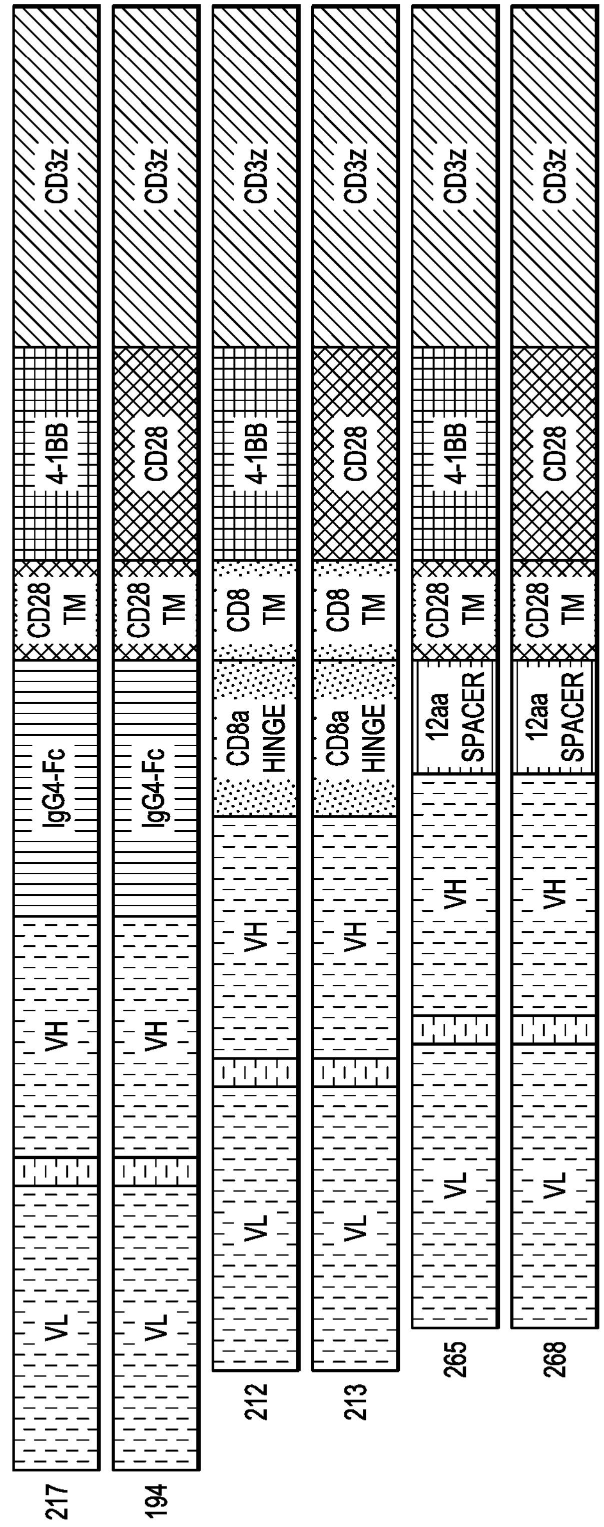
FIG. 26: CAR designs.
FIG. 27: CARs.

Specific CAR constructs are shown in FIG. 26 and FIG. 27. FIG. 26 shows a schematic of CD19-specific CARs having long (IgG4), medium (CD8a hinge) and small (IgG 12 aa) stalks which signaling through CD28 or CD137 endodomains. Nomenclature of CAR molecules with different stalks and signaling are shown in FIG. 27.

Figure 28:
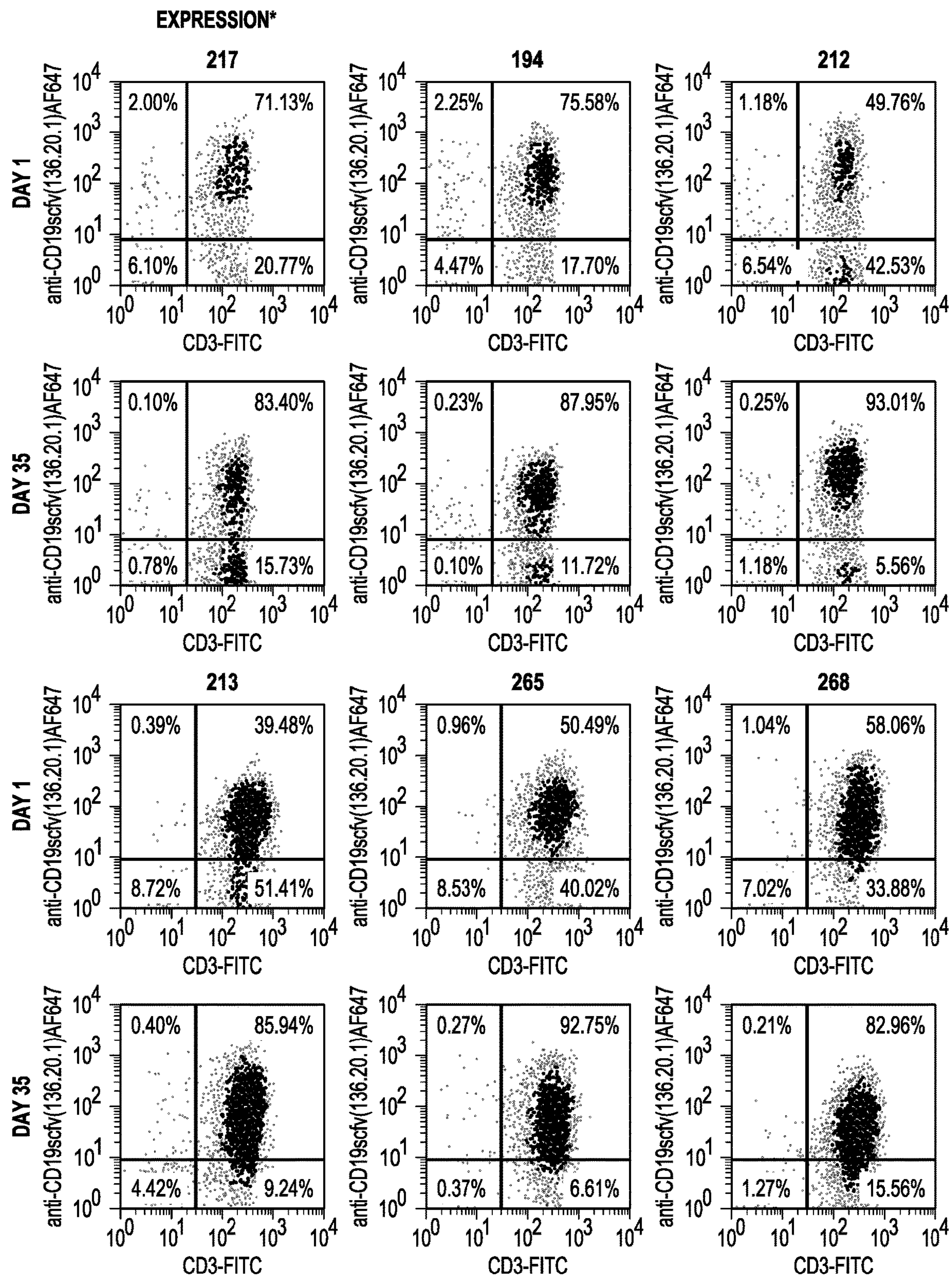
FIG. 28: CAR Expression.

CAR expression was measured. Expression of CAR (as described in FIG. 26) was measured the day after electroporation (day 1) and after 28 days of co-culture on aAPC (day 28). Dot plots of CD3 and CAR (as measured by CD19scfv-specific mAb) are shown in FIG. 28.

Figure 29:
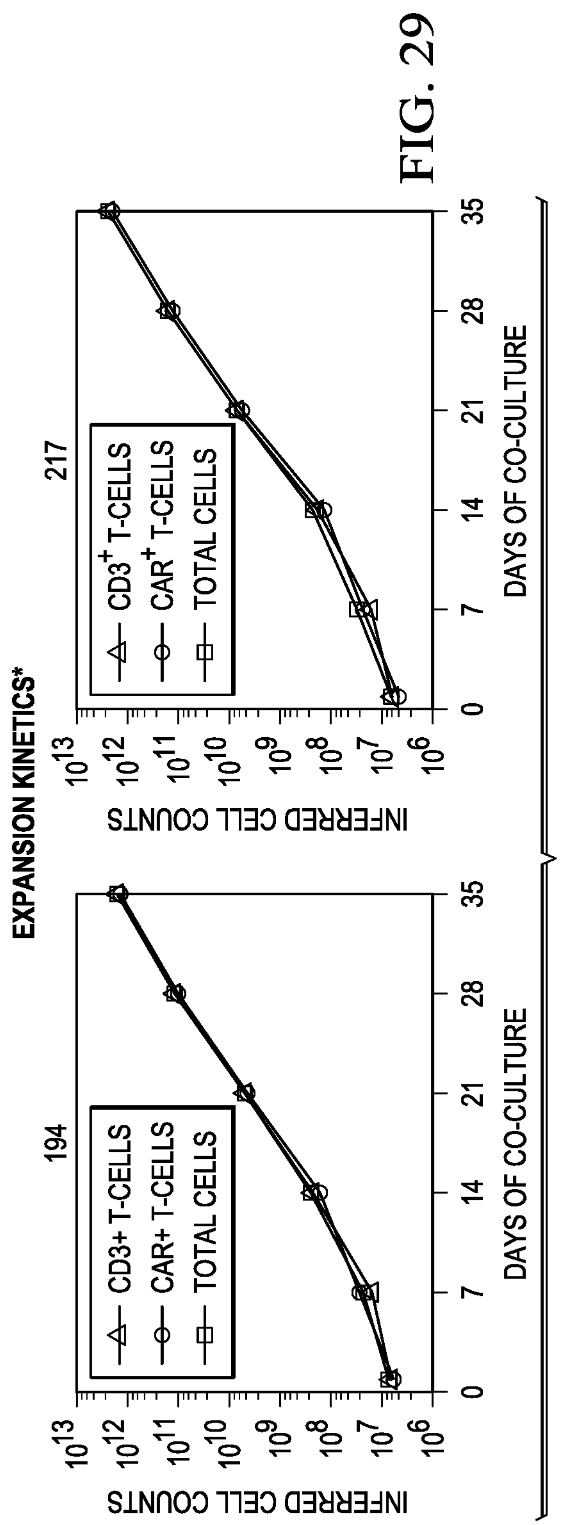
FIG. 29: Expansion Kinetics.
Figure 30:
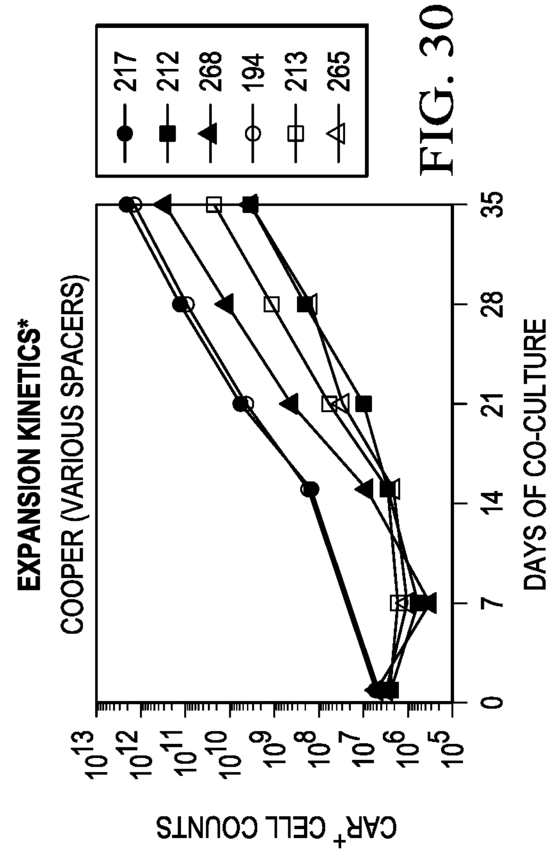
FIG. 30: Expansion Kinetics.

Expansion kinetics were measured for the CAR. T cells electroporated with CAR constructs (shown in FIG. 26) were co-cultured on aAPC in a 7-day stimulation cycle. Cells were counted and evaluated for expression of CD3 and CAR. Results are shown in FIG. 29 and FIG. 30.

Figure 33:
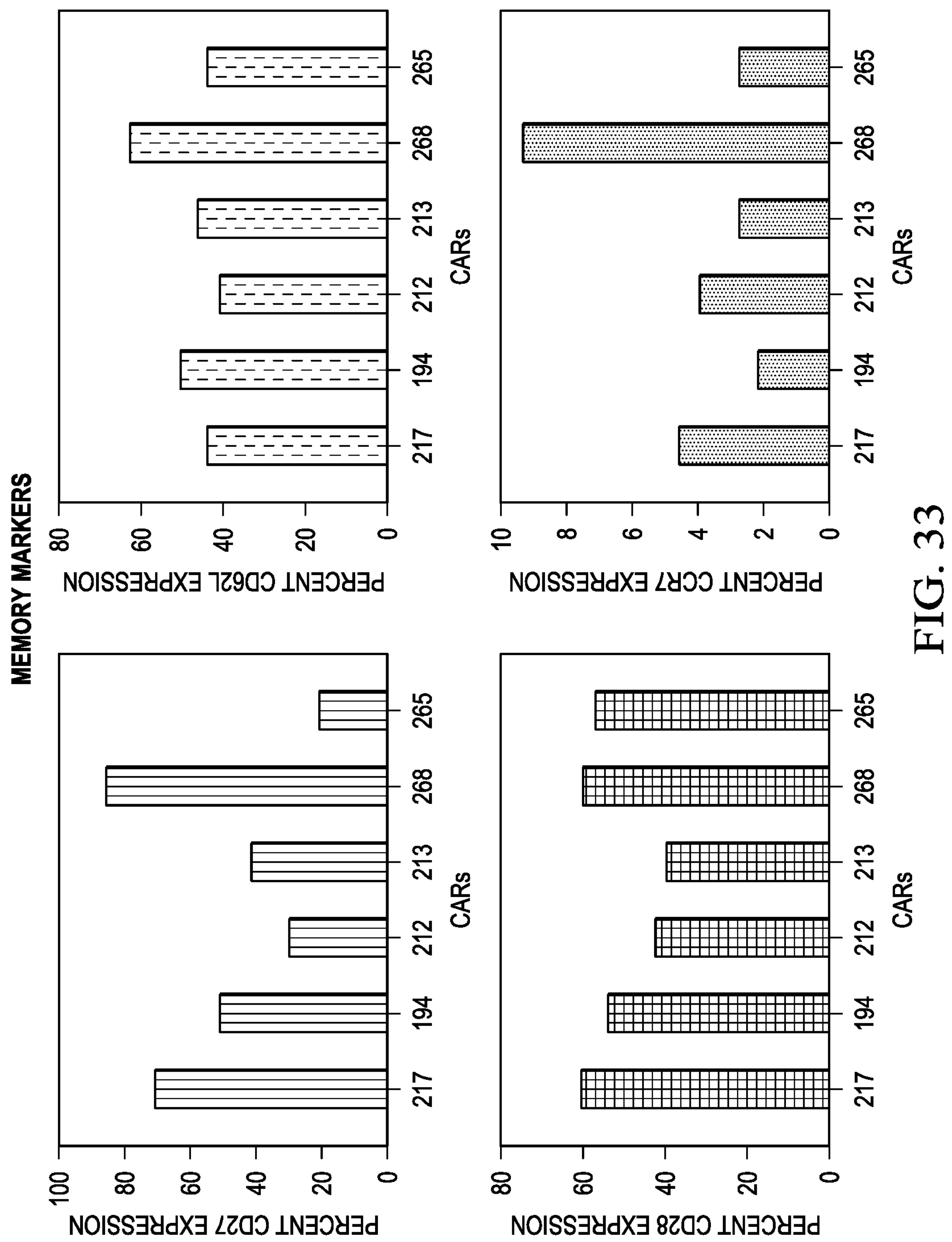
FIG. 33: Memory Markers. Percent expression of CD27, CD62L, CD28 and CCR7 on $CAR^+$ T cells (expressing constructs shown in FIG. 26) are shown.

Cytotoxicity of the CAR$^+$ T cells was measured. At the end of 28 days of co-culture CAR$^+$ T cells (expressing constructs shown in FIG. 26) were evaluated for cytotoxicity against tumor targets in a chromium release assay. As shown in FIG. 31, percent cytotoxicity was measured at various effector-to-target ratio for CD19RCD28 (CAR 194) and CD19RCD137 (CAR 217) CARs against CD19$^+$ and CD19$^{neg}$ tumor targets. As shown in FIG. 32, data were obtained for percent lysis of CD19$^+$ EL-4 by CAR$^+$ T cells (expressing CAR constructs shown in FIG. 26) at E:T ratio of 20:1. The percent expression of CD27, CD62L, CD28 and CCR7 on CAR$^+$ T cells (expressing constructs shown in FIG. 26) was measured, and results are shown in FIG. 33.

Figure 35:
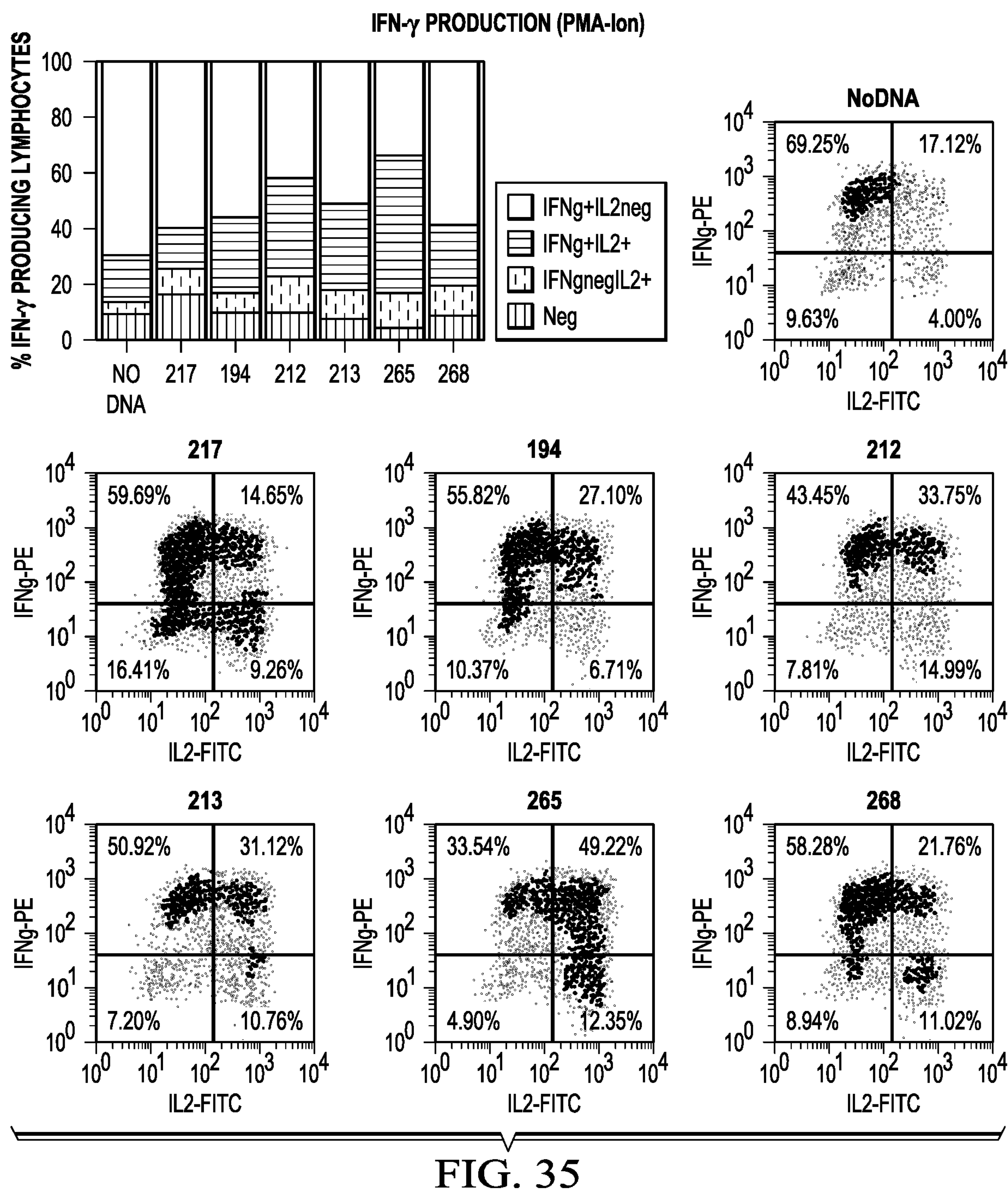
FIG. 35: IFN-γ production (PMA-Ion)

Intracellular cytokine production was measured for the CAR$^+$ T cells. Stimulator cells (CD19$^+$ and CD19$^{neg}$) were incubated with CAR$^+$ T cells (expressing CAR shown in FIG. 26) for 4 hr in the presence of protein transport inhibitor and stained with IFN-γ and IL-2 mAb. PMA-Ionomycin served as a positive control and T cells alone served as negative control. FIG. 34 shows percentage of IFN-γ producing cells after stimulation. FIG. 35 shows breakdown of IFN-γ and or, IL-2 producing cells after incubation with cell stimulation cocktail (PMA-Ionomycin).

Figure 36:
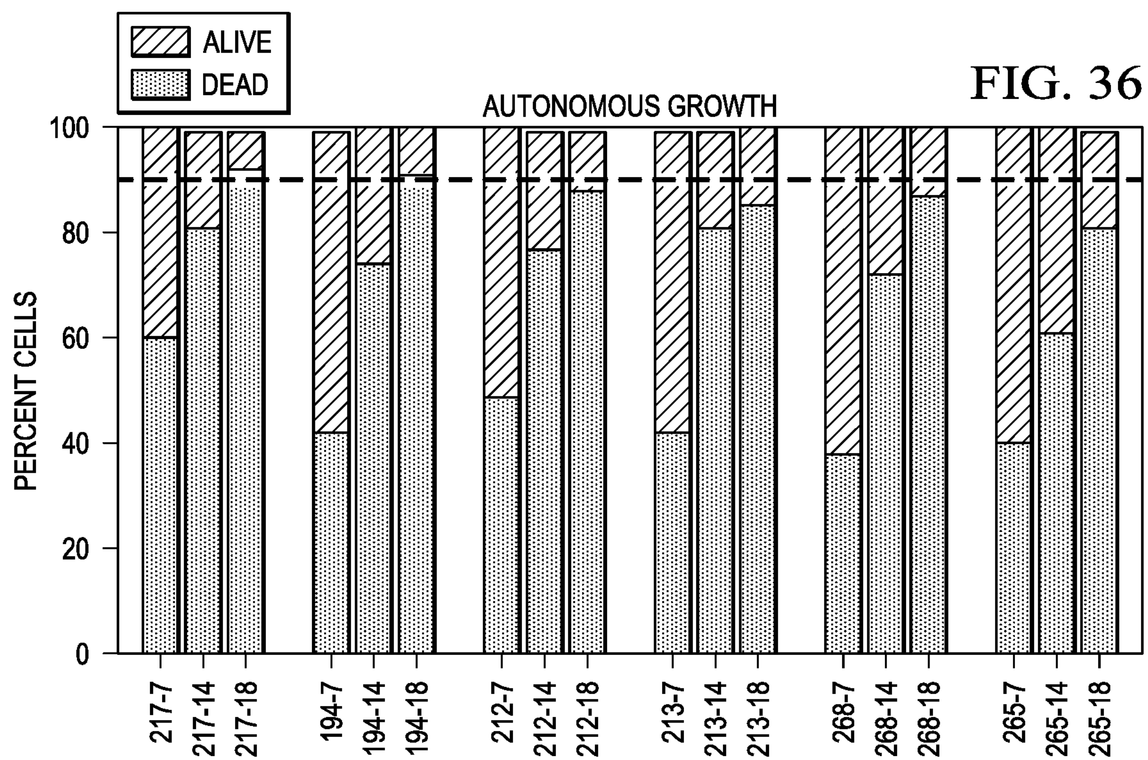
FIG. 36: Autonomous Growth.

The CAR$^+$ T cells were measured for the presence of absence of autonomous growth. CAR$^+$ T cells (expressing CAR described in FIG. 26) were evaluated for their lack of aberrant growth in the absence of external stimulation (cytokines and aAPC) for 18 days. At the end of 18 days, more than 80% of the cells were dead showing lack of unwanted growth. As shown in FIG. 36, a lack of autonomous growth was observed.

Figure 37:
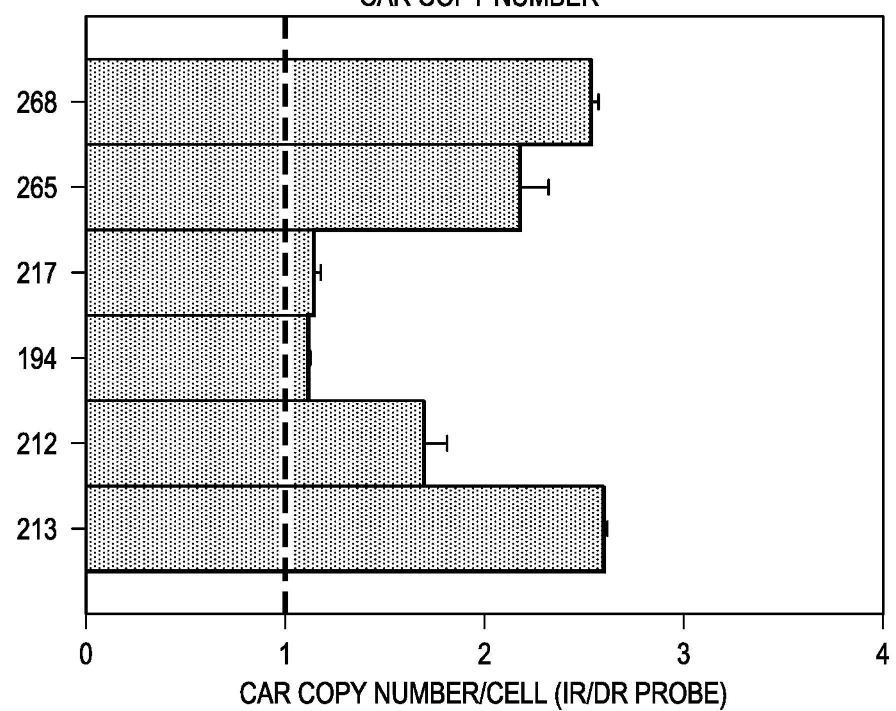
FIG. 37: CAR Copy Number.
Figures 38, 39:
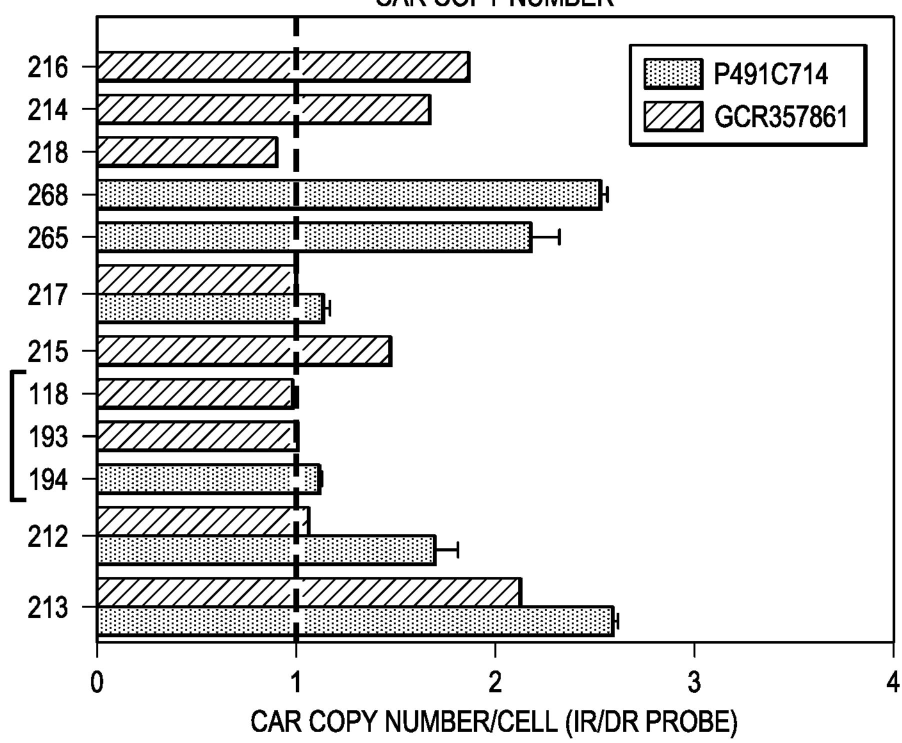
FIG. 38: CAR Copy Number.
FIG. 39: CAR Copy Number.
Figure 40A:
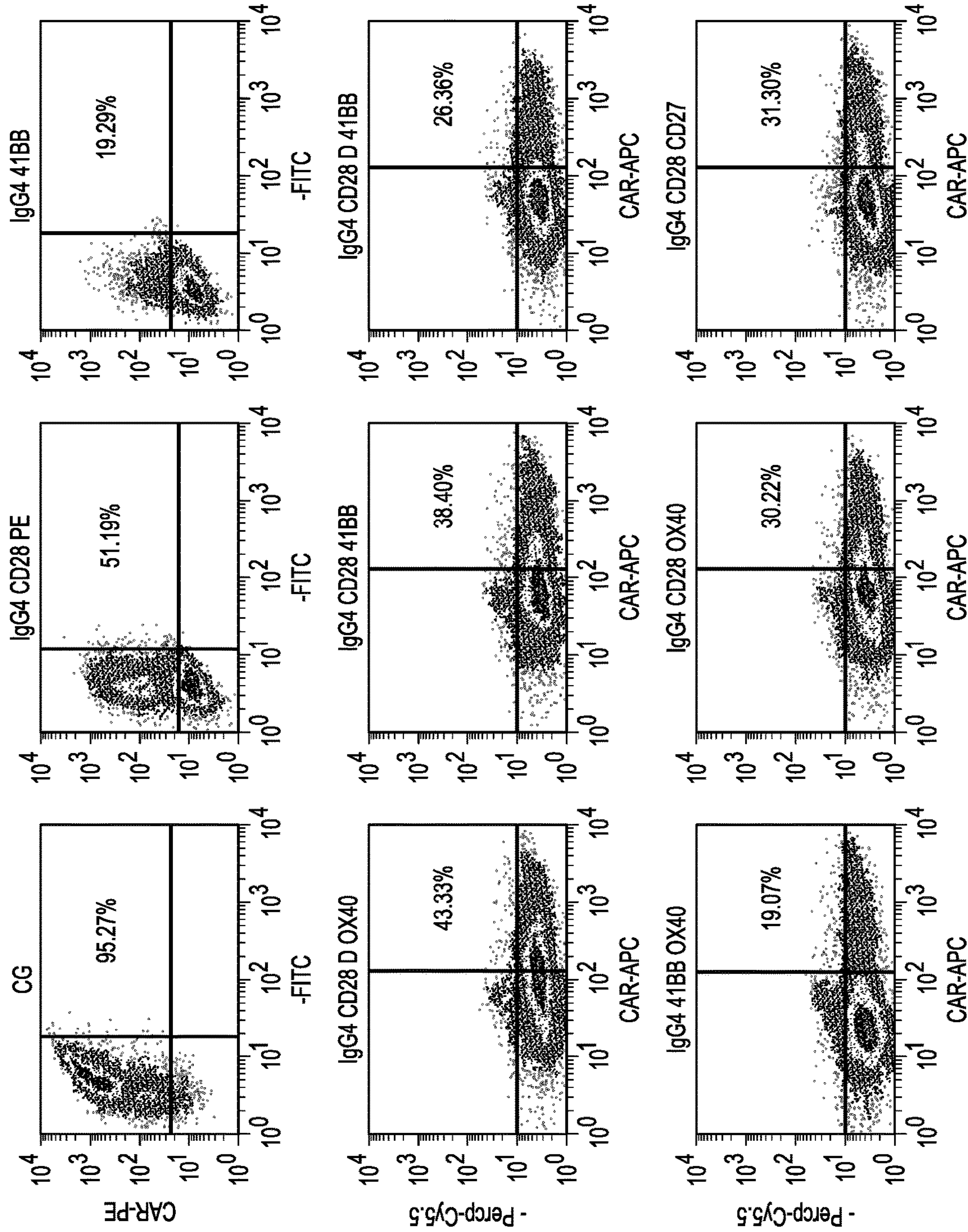
FIGS. 40A-E: Transfection of 293-HEK cells with plasmids carrying the CAR DNA (pSBSO EZ CAR) by lipofectamine was performed. The transfected cells were analyzed by flow cytometry after stained with anti-Fc or anti-idiotipic (antiCD19svFv) antibodies.
Figure 40B:
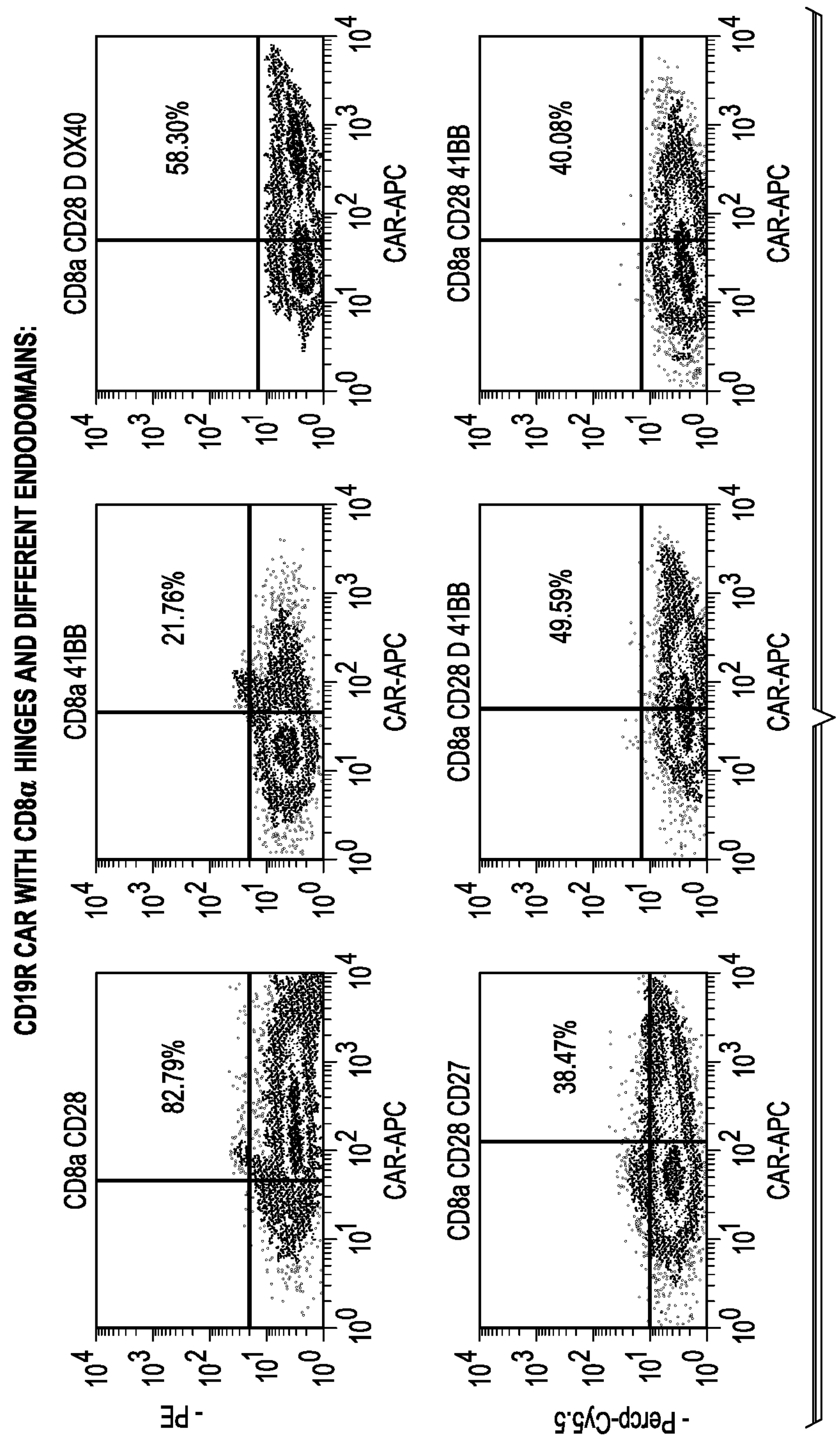
Figure 40C:
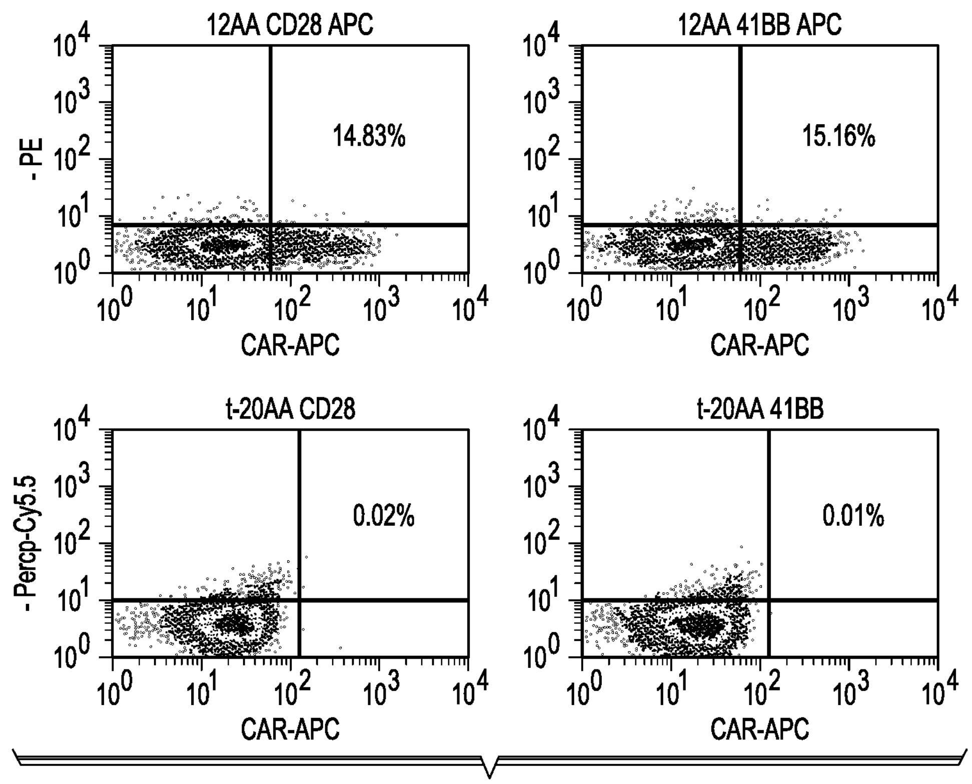
Figure 40D:
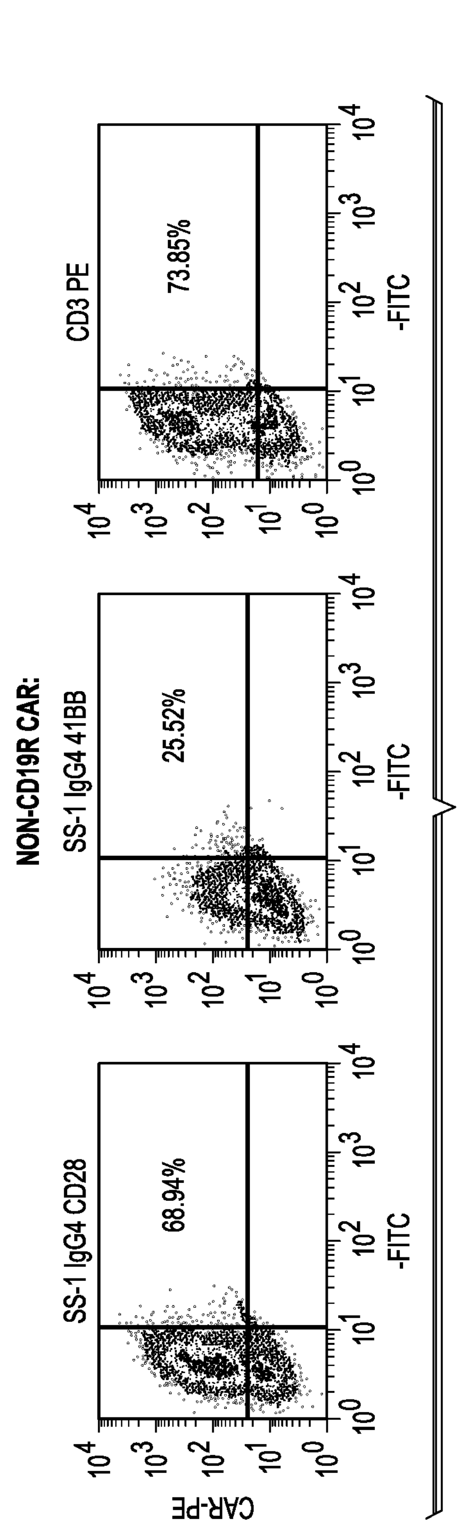
Figure 40E:
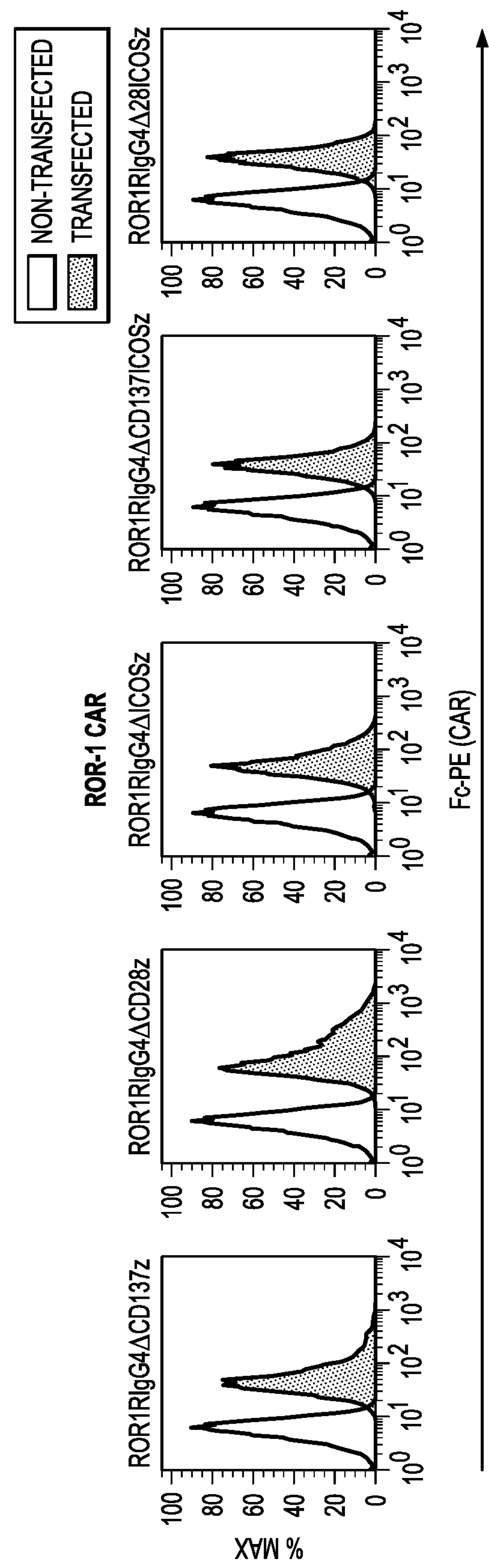

CAR copy number was measured in the CAR$^+$ T cells. The number of copies of integrated CAR molecule was evaluated using primers/probes specific for IgG4-Fc and IR/DR regions by qPCR. As shown in FIG. 37, CAR copy number integrated (of CAR shown in FIG. 26) was observed using the IR/DR probe. As shown in FIG. 38 and FIG. 39, a compilation of CAR copy number data are provided in a table and graphical form for CAR constructs (for both CAR constructs shown in FIG. 3 and CAR constructs shown in FIG. 26) as tested in two separate experiments (P491; C714 and GCR357861).

These data show that CARs with various spacers can be expressed and grown in vitro in the culture system as described herein. All CARs were observed to have similar CAR expression. The maximum cytotoxicity of CD19+ EL-4s was observed in CARs with a CD8 hinge region. Similar expression of CD62L and CD28 was observed on all CARs tested. High integration frequency as measured by CAR copy number was observed in all CAR, except for CAR containing IgG4-Fc stalk. A lack of autonomous growth and SB11 was observed by PCR. Contrary to previous reports, inclusion of a 12 aa spacer in the CAR did not confer improved functionality in these studies.

Example 5

Rapid Assembly of CARs from Principal Components

The inventors generated a CD19-specific CAR that is activated through chimeric CD28/CD3-zeta using the EZ CAR platform in parallel with clinical-grade CD19RCD28mζ CAR+ T cells (CG CAR). Both, Clinical Grade CD28/CD3-ζ and EZ CAR CD19RCD28mζ CARs sequences were inserted into Sleeping Beauty transposon vectors and electroporated into T cells. After electroporation the T cells were cultivated in presence of CD19+ artificial Antigen Presenting Cells (also called Activating and Propagating Cells, or AaPCs) for antigen specific expansion of the T cells. The expression of the CARs in the T cell's surface was measured every week by flow cytometry (Fc+ expression), showing similar CAR expression in Clinical Grade CD19 CAR T cells and EZ CD19 CAR T cells. A Chromium Release Assay (CRA) was also performed to evaluate the killing function of T cells CD19 CAR+ generated by EZ CAR platform against tumor cells. After 4 hours of incubation the percentage of specific cell lysis was observed to be 52% by the EZ CAR T cells and 49% by the CG CAR T cells.

These results demonstrate that functional CAR$^+$ T cells were generated using these methods. The inventors then performed a rapid production of CARs using methods as described above in combination with a library of plasmids containing the following three components of a CAR molecule: (i) anti-CD19 scFv (ii) 5 hinges with different sizes (long—IgG4a and IgG4ΔEQ, medium—CD8α, short—t-20AA and t-12AA) and (iii) different combinations of 7 signaling domains (CD27, CD28, CD28ΔY$^{173}$→F$^{173}$, CD134, CD137, CD278) with the CD3ζ domain. Transfection of HEK 293 cells with plasmid containing the CAR transgene were used to screen 27 different CARs constructs to ensure the expression of the CAR protein in the cell surface. The high throughput testing of individual CAR molecules was undertaken using the iQue™ Screener (Intelicyt, Albuquerque, NM), a high throughput flow cytometer, where cytotoxic assays are performed using engineered target cells expressing a fluorescent granzyme B reporter or GFP. Results are shown in FIGS. 40A-E.

Figure 41A:
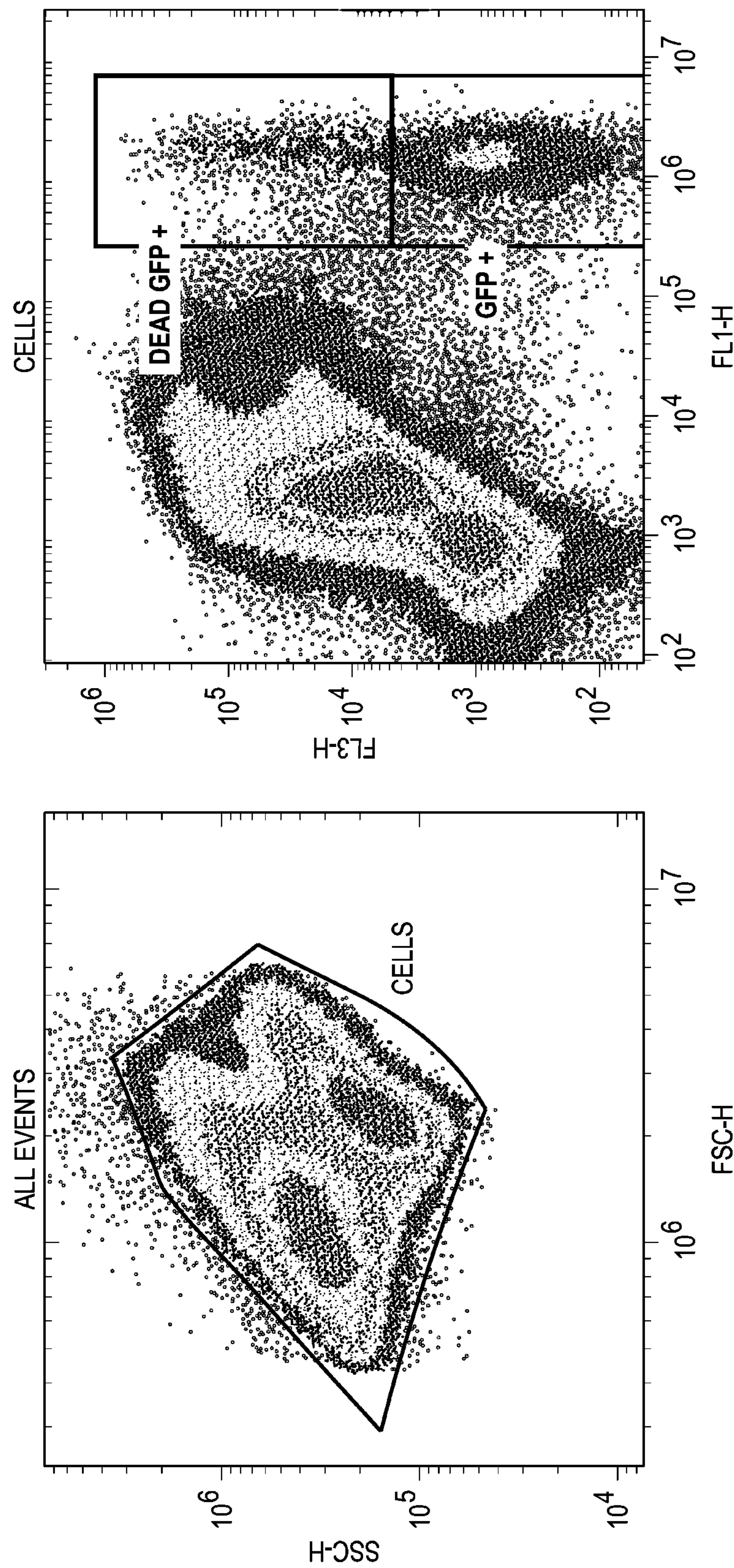
Figure 41C:
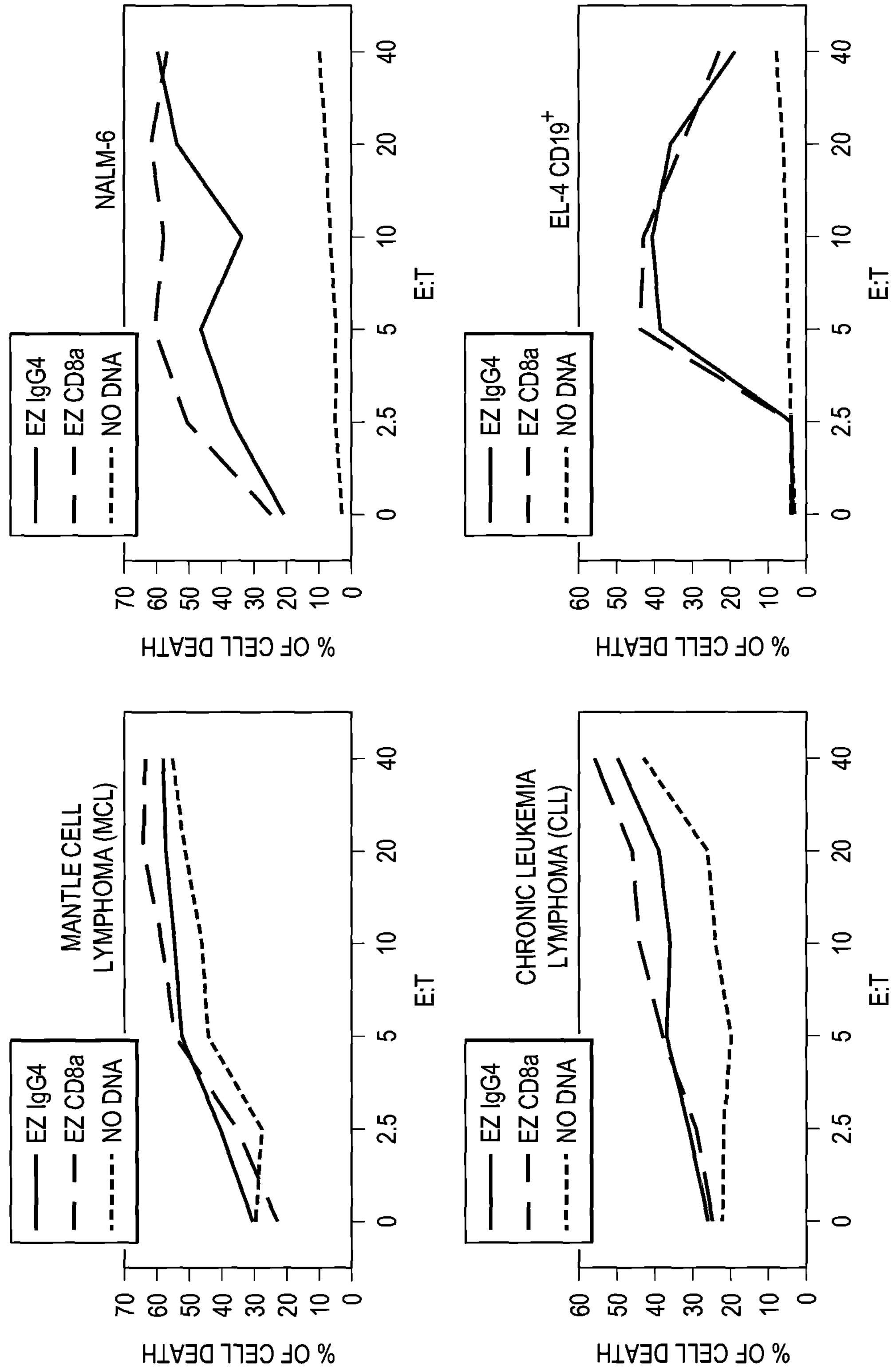
Figure 42:
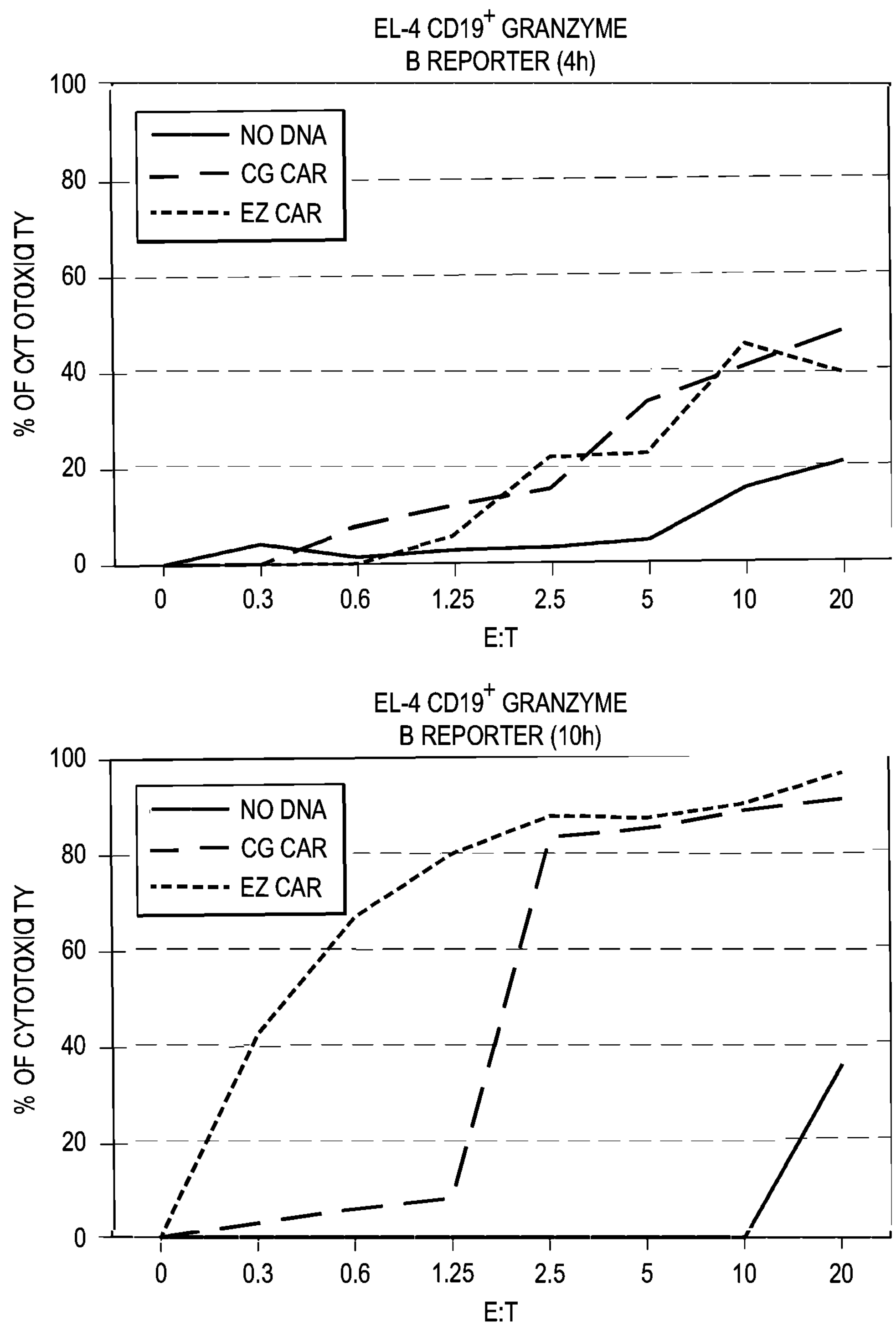
FIG. 42: $5\times10^3$ target cells (EL-4 CD19+Granzyme B cells reporter) were incubated with increasing concentration of Clinical-grade CD19RIgG4CD28CAR T cells, EZ CD19RCD8αCD28 CAR T cells and $CAR^{neg}$ T cells (used as the control) for 4 and 10 hours. After incubation time the cells were acquired by IntelliCyt's iQue and the data analyses were made in their proprietary software. The graphs are representing the killing percentage of CAR T cells against tumor cells. The ratio between effector and target cells ranged from 0 to 20 cells.

Additional experiments were performed to screen the CAR molecules using IntelliCyt's iQue™. iQue™ uses high throughput flow cytometry, a complementary technology that generates information by studying large populations using multiplexing capabilities and cell-by-cell analysis. The inventors adapted this technology to inform on the therapeutic potential of T cells modified with panels of CARs. T cells from the wells can be stained for viability, as well as activation signals (e.g., upregulation of CD25), cytokine release, and killing. Thus the inventors adapted the iQue Screener and harnessed its ability to perform multiplexed bead-based cytokine detection and cell-based assays. The results obtained indicate that this technology may be used to test a large number of different CAR T cells generated by the EZ CAR platform. Data was generated using IntelliCyt's iQue™, where 2 populations of CAR T cells were evaluated on their abilities to kill target cells. Results are shown in FIGS. 41A-B and FIG. 42. These results demonstrate that the CAR molecules were active and the iQue™ method may be effectively used to evaluate CAR activity.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pub. No. 2009/0017000
U.S. Pub. No. 2009/0004142
U.S. Pat. No. 6,225,042
U.S. Pat. No. 6,355,479
U.S. Pat. No. 6,362,001
U.S. Pat. No. 6,410,319
U.S. Pat. No. 6,790,662
U.S. Pat. No. 7,109,304
WO2007/103009
Ahmed and Cheung, FEBS Lett. 2014 Jan. 21; 588(2):288-97.
Altenschmidt et al., Adoptive transfer of in vitro-targeted, activated T lymphocytes results in total tumor regression, J Immunol. 1997 Dec. 1; 159(11):5509-15.
Audet et al., Sci Rep. 2014 Nov. 6; 4:6881.
Berry et al. Adoptive immunotherapy for cancer: the next generation of gene-engineered immune cells. *Tissue Antigens.* 2009 October; 74(4):277-89.
Brocker et al., *Adv. Immunol.,* 68:257, 1998.
Curtin et al., MAbs. 2015 Jan. 2; 7(1):265-75.
Czerwiński et al., Drug Metab Dispos. 2015 January; 43(1): 42-52.
Davies J K, Singh H, Huls H, Yuk D, Lee D A, et al. (2010) Combining CD19 redirection and alloanergization to generate tumor-specific human T cells for allogeneic cell therapy of B-cell malignancies. Cancer Res 70: 3915-3924.
de Weers et al., J Immunol. 2011 Feb. 1; 186(3):1840-8.
Duong et al., (2013) Engineering T Cell Function Using Chimeric Antigen Receptors Identified Using a DNA Library Approach. PLOS ONE 8(5):e63037.
Eshhar et al., Specific activation and targeting of cytotoxic lymphocytes through chimeric single chains consisting of antibody-binding domains and the gamma or zeta subunits of the immunoglobulin and T-cell receptors. Proc Natl Acad Sci USA.; 90(2):720-4, 1993.
Eshhar, Tumor-specific T-bodies: towards clinical application. Cancer Immunol Immunother. 1997 November-December; 45(3-4):131-6. 1997
Fitzer-Attas et al., Harnessing Syk family tyrosine kinases as signaling domains for chimeric single chain of the variable domain receptors: optimal design for T cell activation. J Immunol. 1998 Jan. 1; 160(1):145-54. 1998
Funakoshi et al., Cancer Treat Rev. 2014 December; 40(10): 1221-9.
Gerber et al., Clin Cancer Res. 2011 Nov. 1; 17(21):6888-96.
Goldberg et al., J Clin Oncol. 2014 May 10; 32(14):1445-52.
Gross et al., Expression of immunoglobulin-T-cell receptor chimeric molecules as functional receptors with antibody-type specificity. *Proc. Natl. Acad. Sci. USA,* 86:10024-10028, 1989.
Gross et al. (1992) Endowing T cells with antibody specificity using chimeric T cell receptors. FASEB J. 1992 December; 6(15):3370-8.
Hackett et al., A transposon and transposase system for human application, *Mol Ther.* 2010 April; 18(4):674-83).
Hekele et al. Growth retardation of tumors by adoptive transfer of cytotoxic T lymphocytes reprogrammed by CD44v6-specific scFv:zeta-chimera. Int J Cancer. 1996 Oct. 9; 68(2):232-8, 1996.
Huls et al., Clinical Application of Sleeping Beauty and Artificial Antigen Presenting Cells to Genetically Modify T Cells from Peripheral and Umbilical Cord Blood. *J. Vis. Exp., doi:*10.3791/50070, 2013.
Huls et al. "Clinical application of Sleeping Beauty and artificial antigen presenting cells to genetically modify T cells from peripheral and umbilical cord blood" J Vis Exp. 2013 Feb. 1; (72):e50070.
Humblet-Baron and Baron, Immunol Cell Biol. 2015 Feb. 10. doi: 10.1038/icb.2014.120.
Hwu et al. (1995) In vivo antitumor activity of T cells redirected with chimeric antibody/T-cell receptor genes. Cancer Res. 1995 Aug. 1; 55(15):3369-73.

Ikeda et al., Clin Cancer Res. 2009 Jun. 15; 15(12):4028-37.
Jabbour et al., *Am J Hematol.* 2014 Nov. 18.
Kaufmann et al., *Hum Pathol.* 1997 December; 28(12): 1373-8.
Kaufman et al., *Br J Haematol.* 2013 November; 163(4): 478-86.
Kim D W, Uetsuki T, Kaziro Y, Yamaguchi N, Sugano S (1990) Use of the human elongation factor 1 alpha promoter as a versatile and efficient expression system. Gene 91: 217-223.
Kim et al., 2004, Nature, Vol. 22(4), pp. 403-410.
Kim et al., Immunology. 2010 August; 130(4):545-55.
Kong et al., *Leuk Res.* 2014 November; 38(11):1320-6.
Krebs et al., T cells expressing a chimeric antigen receptor that binds hepatitis B virus envelope proteins control virus replication in mice. *Gastroenterology.* 2013 August; 145 (2):456-65.
Le Garff-Tavernier et al., Haematologica. 2014 Dec. 31.
Lennard S., Standard protocols for the construction of scFv libraries. Methods Mol Biol. 2002; 178:59-71.
Leung, Molecular Imaging and Contrast Agent Database (MICAD), Bethesda (Md.): National Center for Biotechnology Information (US); 2004-2013. 2010 Mar. 25
Leung 2011, IRDye800CW-anti-CD105 TRC105 chimeric monoclonal antibody. Molecular Imaging and Contrast Agent Database (MICAD). Bethesda (Md.): National Center for Biotechnology Information (US); 2004-2013. 2011 Dec. 1
Maiti et al., Sleeping beauty system to redirect T-cell specificity for human applications. *J Immunother.* 36(2):112-23, 2013.
Manero et al., Haematologica. 2013 February; 98(2):217-21.
Molecular Therapy 17 (8): 1453-1464, 2009.
Moritz et al. (1994) Cytotoxic T lymphocytes with a grafted recognition specificity for ERBB2-expressing tumor cells. Proc Natl Acad Sci USA. 1994 May 10; 91(10): 4318-22.
Patel et al., Anticancer Res. 2008 September-October; 28(5A):2679-86.
Qiu et al., PLoS Negl Trop Dis. 2012; 6(3):e1575.
Remington's Pharmaceutical Sciences, 16th Ed., Mack, ed. (1980)
Rushworth et al., (2014) "Universal Artificial Antigen Presenting Cells to Selectively Propagate T Cells Expressing Chimeric Antigen Receptor Independent of Specificity" *J Immunother*. May; 37(4):204-13.
Sarup et al., Mol Cancer Ther. 2008 October; 7(10):3223-36.
Schneider, J. Embryol. Exp. Morph. 1972 Vol 27, pp. 353-365
Schultz-Thater et al., Br J Cancer. 2000 July; 83(2):204-8.
Shin et al, Immune Netw. 2011 April; 11(2):114-22.
Singh et al., Redirecting specificity of T-cell populations for CD19 using the Sleeping Beauty system. *Cancer Res.,* 68:2961-2971, 2008.
Singh H, Figliola M J, Dawson M J, Huls H, Olivares S, et al. (2011) Reprogramming CD19-specific T cells with IL-21 signaling can improve adoptive immunotherapy of B-lineage malignancies. Cancer Res 71: 3516-3527.
Singh et al. "A new approach to gene therapy using Sleeping Beauty to genetically modify clinical-grade T cells to target CD19." *Immunol Rev.* 2014 January; 257(1):181-90.
Singh et al., "Manufacture of T cells using the Sleeping Beauty system to enforce expression of a CD19-specific chimeric antigen receptor." Cancer Gene Ther. 2015 Jan. 16.
Stancovski et al. (1993)
Stynen et al., Fungal Cell Wall and Immune Response, NATO ASI Series Volume 53, 1991, pp 181-193.
Sun et al., Cell Mol Immunol. 2007 June; 4(3):209-14.
Turtle et al., "Artificial antigen-presenting cells for use in adoptive immunotherapy" *Cancer J.* 2010 July-August; 16(4):374-81.
Verel, Int J Cancer. 2002 May 20; 99(3):396-402.
Vincent and Samuel, Journal of Immunological Methods, Volume 165, Issue 2, 15 Oct. 1993, Pages 177-182.
Wang et al., Immunology. 2015 February; 144(2):254-62.
Weijtens et al. (1996) Single chain Ig/gamma gene-redirected human T lymphocytes produce cytokines, specifically lyse tumor cells, and recycle lytic capacity. J Immunol. 1996 Jul. 15; 157(2):836-43.
Wieczorek et al., Genetically Modified T Cells for the Treatment of Malignant Disease. *Transfus Med Hemother.* 2013 December; 40(6):388-402.
Winiarska et al., MAbs. 2014; 6(5):1300-13.
Zhuang et al., Cancer Cell Int. 2014 Nov. 30; 14(1):109.
Zhang et al., Angiogenesis. 2002; 5(1-2):35-44.

What is claimed is:

1. A polypeptide encoded by a nucleic acid sequence comprising nucleotides 67-1485 of SEQ ID NO: 5.

2. The polypeptide of claim 1, wherein the nucleic acid sequence comprises nucleotides 1-1485 of SEQ ID NO: 5.

3. The polypeptide of claim 1, wherein the nucleic acid sequence comprises SEQ ID NO: 5.

4. A T cell comprising the polypeptide of claim 1.

5. The T cell of claim 4, wherein the T cell is an alpha beta T cell, a gamma delta T cell, or an NKT cell.

6. The T cell of claim 4, further comprising a membrane-bound cytokine.

7. The T cell of claim 6, wherein the membrane-bound cytokine is membrane-bound IL-15.

8. A pharmaceutical preparation comprising the T cell of claim 4.

9. A method of treating a B-cell malignancy in a human subject in need thereof, the method comprising administering the T cell of claim 4 to the human subject.

10. The method of claim 9, wherein the B-cell malignancy is a lymphoma or a leukemia.

11. A nucleic acid comprising nucleotides 67-1485 of SEQ ID NO: 5.

12. The nucleic acid of claim 11, wherein the nucleic acid comprises nucleotides 1-1485 of SEQ ID NO:5.

13. A transposon comprising the nucleic acid of claim 11.

14. A T cell comprising the nucleic acid of claim 11.

15. The T cell of claim 14, wherein the T cell is an alpha beta T cell, a gamma delta T cell, or an NKT cell.

16. The T cell of claim 14, further comprising a membrane-bound cytokine.

17. The T cell of claim 16, wherein the membrane-bound cytokine is membrane-bound IL-15.

18. A pharmaceutical preparation comprising the T cell of claim 14.

19. A method of treating a B-cell malignancy in a human subject in need thereof, the method comprising administering the T cell of claim 14 to the human subject.

20. The method of claim 19, wherein the B-cell malignancy is a lymphoma or a leukemia.

* * * * *

SEQUENCE LISTING

```
<160> NUMBER OF SEQ ID NOS: 59

<210> SEQ ID NO 1
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 1

gagagcaagt acggccctcc ctgccccct tgccct                              36


<210> SEQ ID NO 2
<211> LENGTH: 2037
<212> TYPE: DNA
<213> ORGANISM: Artificial sequence
<220> FEATURE:
<223> OTHER INFORMATION: Synthetic oligonucleotide

<400> SEQUENCE: 2
```

```
atgctgctgc tggtgaccag cctgctgctg tgtgagctgc cccaccccgc ctttctgctg     60
atccccgaca tccagatgac ccagaccacc tccagcctga gcgccagcct gggcgaccgg    120
gtgaccatca gctgccgggc cagccaggac atcagcaagt acctgaactg gtatcagcag    180
aagcccgacg gcaccgtcaa gctgctgatc taccacacca gccggctgca cagcggcgtg    240
cccagccggt ttagcggcag cggctccggc accgactaca gcctgaccat ctccaacctg    300
gagcaggagg acatcgccac ctacttttgc cagcagggca acacactgcc ctacaccttt    360
ggcggcggaa caaagctgga gatcaccggc agcacctccg gcagcggcaa gcctggcagc    420
ggcgagggca gcaccaaggg cgaggtgaag ctgcaggaga gcggccctgg cctggtggcc    480
cccagccaga gcctgagcgt gacctgtacc gtgtccggcg tgtccctgcc cgactacggc    540
gtgtcctgga tccggcagcc ccctaggaag ggcctggagt ggctgggcgt gatctggggc    600
agcgagacca cctactacaa cagcgccctg aagagccggc tgaccatcat caaggacaac    660
agcaagagcc aggtgttcct gaagatgaac agcctgcaga ccgacgacac cgccatctac    720
tactgtgcca agcactacta ctacggcggc agctacgcca tggactactg gggccagggc    780
accagcgtga ccgtgtccag cgagagcaag tacggccctc cctgcccccc ttgccctgcc    840
cccgagttcc tgggcggacc cagcgtgttc ctgttccccc ccaagcccaa ggacaccctg    900
atgatcagcc ggacccccga ggtgacctgt gtggtggtgg acgtgtccca ggaggacccc    960
gaggtccagt tcaactggta cgtggacggc gtggaggtgc acaacgccaa gaccaagccc   1020
cgggaggagc agttcaatag cacctaccgg gtggtgtccg tgctgaccgt gctgcaccag   1080
gactggctga acggcaagga atacaagtgt aaggtgtcca acaagggcct gcccagcagc   1140
atcgagaaaa ccatcagcaa ggccaagggc cagcctcggg agccccaggt gtacaccctg   1200
cccccctagcc aagaggagat gaccaagaat caggtgtccc tgacctgcct ggtgaagggc   1260
ttctacccca gcgacatcgc cgtggagtgg gagagcaacg gccagcccga gaacaactac   1320
aagaccaccc cccctgtgct ggacagcgac ggcagcttct tcctgtacag caggctgacc   1380
gtggacaaga gccggtggca ggagggcaac gtctttagct gctccgtgat gcacgaggcc   1440
ctgcacaacc actacaccca gaagagcctg tccctgagcc tgggcaagat gttctgggtg   1500
ctggtcgtgg tgggtggcgt gctggcctgc tacagcctgc tggtgacagt ggccttcatc   1560
atcttttggg tgaagagagg ccggaagaaa ctgctgtaca tcttcaagca gcccttcatg   1620
cggcccgtgc agaccaccca ggaagaggac ggctgcagct gccggttccc cgaggaagag   1680
gaaggcggct gcgaactgcg ggtgaagttc agccggagcg ccgacgcccc tgcctaccag   1740
cagggccaga accagctgta caacgagctg aacctgggcc ggagggagga gtacgacgtg   1800
ctggacaagc ggagaggccg ggaccctgag atgggcggca agccccggag aaagaaccct   1860
caggagggcc tgtataacga actgcagaaa gacaagatgg ccgaggccta cagcgagatc   1920
ggcatgaagg gcgagcggcg gaggggcaag ggccacgacg gcctgtacca gggcctgagc   1980
accgccacca aggataccta cgacgccctg cacatgcagg ccctgccccc cagatga      2037
```

```
<210> SEQ ID NO 3
<211> LENGTH: 2034
<212> TYPE: DNA
<213> ORGANISM: Artificial sequence
<220> FEATURE:
<223> OTHER INFORMATION: Synthetic oligonucleotide

<400> SEQUENCE: 3
```

```
atgctgctgc tggtgaccag cctgctgctg tgtgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480

cccagccaga gcctgagcgt gacctgtacc gtgtccggcg tgtccctgcc cgactacggc    540

gtgtcctgga tccggcagcc ccctaggaag ggcctggagt ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgtgcca agcactacta ctacggcggc agctacgcca tggactactg gggccagggc    780

accagcgtga ccgtgtccag cgagagcaag tacggccctc cctgcccccc ttgccctgcc    840

cccgagttcc tgggcggacc cagcgtgttc ctgttccccc ccaagcccaa ggacaccctg    900

atgatcagcc ggacccccga ggtgacctgt gtggtggtgg acgtgtccca ggaggacccc    960

gaggtccagt tcaactggta cgtggacggc gtggaggtgc acaacgccaa gaccaagccc   1020

cgggaggagc agttcaatag cacctaccgg gtggtgtccg tgctgaccgt gctgcaccag   1080

gactggctga acggcaagga atacaagtgt aaggtgtcca acaagggcct gcccagcagc   1140

atcgagaaaa ccatcagcaa ggccaagggc cagcctcggg agccccaggt gtacaccctg   1200

cccccctagcc aagaggagat gaccaagaat caggtgtccc tgacctgcct ggtgaagggc   1260

ttctacccca gcgacatcgc cgtggagtgg gagagcaacg gccagcccga gaacaactac   1320

aagaccaccc cccctgtgct ggacagcgac ggcagcttct tcctgtacag caggctgacc   1380

gtggacaaga gccggtggca ggagggcaac gtctttagct gctccgtgat gcacgaggcc   1440

ctgcacaacc actacaccca gaagagcctg tccctgagcc tgggcaagat gttctgggtg   1500

ctggtcgtgg tgggtggcgt gctggcctgc tacagcctgc tggtgacagt ggccttcatc   1560

atcttttggg tgaggagcaa gcggagcaga ggcggccaca gcgactacat gaacatgacc   1620

ccccggaggc ctggccccac ccggaagcac taccagccct acgcccctcc cagggacttc   1680

gccgcctacc ggagccgggt gaagttcagc cggagcgccg acgcccctgc ctaccagcag   1740

ggccagaacc agctgtacaa cgagctgaac ctgggccgga gggaggagta cgacgtgctg   1800

gacaagcgga gaggccggga ccctgagatg ggcggcaagc cccggagaaa gaaccctcag   1860

gagggcctgt ataacgaact gcagaaagac aagatggccg aggcctacag cgagatcggc   1920

atgaagggcg agcggcggag gggcaagggc cacgacggcc tgtaccaggg cctgagcacc   1980

gccaccaagg atacctacga cgccctgcac atgcaggccc tgccccccag atga         2034
```

```
<210> SEQ ID NO 4
<211> LENGTH: 1491
<212> TYPE: DNA
<213> ORGANISM: Artificial sequence
<220> FEATURE:
<223> OTHER INFORMATION: Synthetic oligonucleotide

<400> SEQUENCE: 4

atgctgctgc tggtgaccag cctgctgctg tgtgagctgc cccaccccgc ctttctgctg     60
```

```
atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480

cccagccaga gcctgagcgt gacctgtacc gtgtccggcg tgtccctgcc cgactacggc    540

gtgtcctgga tccggcagcc ccctaggaag ggcctggagt ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgtgcca agcactacta ctacggcggc agctacgcca tggactactg gggccagggc    780

accagcgtga ccgtgtccag caagcccacc accacccctg cccccagacc tccaacccca    840

gcccctacaa tcgccagcca gcccctgagc ctgaggcccg aagcctgtag acctgccgct    900

ggcggagccg tgcacaccag aggcctggat ttcgcctgcg acatctacat ctgggcccct    960

ctggccggca cctgtggcgt gctgctgctg agcctggtca tcaccctgta ctgcaaccac   1020

cggaacaaga gaggccggaa gaaactgctg tacatcttca agcagccctt catgcggccc   1080

gtgcagacca cccaggaaga ggacggctgc agctgccggt tccccgagga agaggaaggc   1140

ggctgcgaac tgcgggtgaa gttcagccgg agcgccgacg cccctgccta ccagcagggc   1200

cagaaccagc tgtacaacga gctgaacctg ggccggaggg aggagtacga cgtgctggac   1260

aagcggagag gccgggaccc tgagatgggc ggcaagcccc ggagaaagaa ccctcaggag   1320

ggcctgtata acgaactgca gaaagacaag atggccgagg cctacagcga gatcggcatg   1380

aagggcgagc ggcggagggg caagggccac gacggcctgt accagggcct gagcaccgcc   1440

accaaggata cctacgacgc cctgcacatg caggccctgc cccccagatg a            1491
```

```
<210> SEQ ID NO 5
<211> LENGTH: 1488
<212> TYPE: DNA
<213> ORGANISM: Artificial sequence
<220> FEATURE:
<223> OTHER INFORMATION: Synthetic oligonucleotide

<400> SEQUENCE: 5

atgctgctgc tggtgaccag cctgctgctg tgtgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480

cccagccaga gcctgagcgt gacctgtacc gtgtccggcg tgtccctgcc cgactacggc    540

gtgtcctgga tccggcagcc ccctaggaag ggcctggagt ggctgggcgt gatctggggc    600
```

-continued

```
agcgagacca cctactacaa cagcgccctg aagagccggc tgaccatcat caaggacaac     660

agcaagagcc aggtgttcct gaagatgaac agcctgcaga ccgacgacac cgccatctac     720

tactgtgcca agcactacta ctacggcggc agctacgcca tggactactg gggccagggc     780

accagcgtga ccgtgtccag caagcccacc accacccctg cccctagacc tccaacccca     840

gcccctacaa tcgccagcca gcccctgagc ctgaggcccg aagcctgtag acctgccgct     900

ggcggagccg tgcacaccag aggcctggat ttcgcctgcg acatctacat ctgggcccct     960

ctggccggca cctgtggcgt gctgctgctg agcctggtca tcaccctgta ctgcaaccac    1020

cggaatagga gcaagcggag cagaggcggc cacagcgact acatgaacat gacccccccgg    1080

aggcctggcc ccacccggaa gcactaccag ccctacgccc ctcccaggga cttcgccgcc    1140

taccggagcc gggtgaagtt cagccggagc gccgacgccc ctgcctacca gcagggccag    1200

aaccagctgt acaacgagct gaacctgggc cggagggagg agtacgacgt gctggacaag    1260

cggagaggcc gggaccctga gatgggcggc aagccccgga gaaagaaccc tcaggagggc    1320

ctgtataacg aactgcagaa agacaagatg gccgaggcct acagcgagat cggcatgaag    1380

ggcgagcggc ggaggggcaa gggccacgac ggcctgtacc agggcctgag caccgccacc    1440

aaggatacct acgacgccct gcacatgcag gccctgcccc ccagatga                 1488
```

```
<210> SEQ ID NO 6
<211> LENGTH: 1380
<212> TYPE: DNA
<213> ORGANISM: Artificial sequence
<220> FEATURE:
<223> OTHER INFORMATION: Synthetic oligonucleotide

<400> SEQUENCE: 6

atgctgctgc tggtgaccag cctgctgctg tgtgagctgc cccaccccgc ctttctgctg      60

atccccgaca tccagatgac ccagaccacc tccagcctga gcgccagcct gggcgaccgg     120

gtgaccatca gctgccgggc cagccaggac atcagcaagt acctgaactg gtatcagcag     180

aagcccgacg gcaccgtcaa gctgctgatc taccacacca gccggctgca cagcggcgtg     240

cccagccggt ttagcggcag cggctccggc accgactaca gcctgaccat ctccaacctg     300

gagcaggagg acatcgccac ctacttttgc cagcagggca acacactgcc ctacaccttt     360

ggcggcggaa caaagctgga gatcaccggc agcacctccg gcagcggcaa gcctggcagc     420

ggcgagggca gcaccaaggg cgaggtgaag ctgcaggaga gcggccctgg cctggtggcc     480

cccagccaga gcctgagcgt gacctgtacc gtgtccggcg tgtccctgcc cgactacggc     540

gtgtcctgga tccggcagcc ccctaggaag ggcctggagt ggctgggcgt gatctggggc     600

agcgagacca cctactacaa cagcgccctg aagagccggc tgaccatcat caaggacaac     660

agcaagagcc aggtgttcct gaagatgaac agcctgcaga ccgacgacac cgccatctac     720

tactgtgcca agcactacta ctacggcggc agctacgcca tggactactg gggccagggc     780

accagcgtga ccgtgtccag cgagagcaag tacggccctc cctgcccccc ttgccctttc     840

tgggtgctgg tcgtggtggg tggcgtgctg gcctgctaca gcctgctggt gacagtggcc     900

ttcatcatct tttgggtgag gagcaagcgg agcagaggcg gccacagcga ctacatgaac     960

atgacccccc ggaggcctgg ccccacccgg aagcactacc agccctacgc ccctcccagg    1020

gacttcgccg cctaccggag ccgggtgaag ttcagccgga gcgccgacgc ccctgcctac    1080

cagcagggcc agaaccagct gtacaacgag ctgaacctgg gccggaggga ggagtacgac    1140

gtgctggaca agcggagagg ccgggaccct gagatgggcg gcaagccccg gagaaagaac    1200
```

```
cctcaggagg gcctgtataa cgaactgcag aaagacaaga tggccgaggc ctacagcgag   1260

atcggcatga agggcgagcg gcggaggggc aagggccacg acggcctgta ccagggcctg   1320

agcaccgcca ccaaggatac ctacgacgcc ctgcacatgc aggccctgcc ccccagatga   1380
```

<210> SEQ ID NO 7
<211> LENGTH: 1383
<212> TYPE: DNA
<213> ORGANISM: Artificial sequence
<220> FEATURE:
<223> OTHER INFORMATION: Synthetic oligonucleotide

<400> SEQUENCE: 7

```
atgctgctgc tggtgaccag cctgctgctg tgtgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480

cccagccaga gcctgagcgt gacctgtacc gtgtccggcg tgtccctgcc cgactacggc    540

gtgtcctgga tccggcagcc ccctaggaag ggcctggagt ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgtgcca agcactacta ctacggcggc agctacgcca tggactactg gggccagggc    780

accagcgtga ccgtgtccag cgagagcaag tacggccctc cctgcccccc ttgccctttc    840

tgggtgctgg tcgtggtggg tggcgtgctg gcctgctaca gcctgctggt gacagtggcc    900

ttcatcatct tttgggtgaa gagaggccgg aagaaactgc tgtacatctt caagcagccc    960

ttcatgcggc ccgtgcagac cacccaggaa gaggacggct gcagctgccg gttccccgag   1020

gaagaggaag gcggctgcga actgcgggtg aagttcagcc ggagcgccga cgcccctgcc   1080

taccagcagg gccagaacca gctgtacaac gagctgaacc tgggccggag ggaggagtac   1140

gacgtgctgg acaagcggag aggccgggac cctgagatgg gcggcaagcc ccggagaaag   1200

aaccctcagg agggcctgta taacgaactg cagaaagaca agatggccga ggcctacagc   1260

gagatcggca tgaagggcga gcggcggagg ggcaagggcc acgacggcct gtaccagggc   1320

ctgagcaccg ccaccaagga tacctacgac gccctgcaca tgcaggccct gccccccaga   1380

tga                                                                 1383
```

<210> SEQ ID NO 8
<211> LENGTH: 720
<212> TYPE: DNA
<213> ORGANISM: Artificial sequence
<220> FEATURE:
<223> OTHER INFORMATION: Synthetic oligonucleotide

<400> SEQUENCE: 8

```
atctgcgaca tccagatgac ccagagccct gccagcctgt ctaccagcct gggcgagaca     60

gtgaccatcc agtgtcaggc cagcgaggac atctactctg gcctggcttg gtatcagcag    120
```

```
aagcccggca agagccctca gctgctgatc tacggcgcca gcgacctgca ggacggcgtg    180

ccaagcagat tcagcggcag cggctccgga acccagtaca gcctgaagat caccagcatg    240

cagaccgagg acgagggcgt gtacttctgc cagcaaggcc tgacctaccc tagaaccttc    300

ggaggaggca ccaagctgga actgaagggc ggaggcggaa gtggaggcgg aggatctggc    360

ggcggaggct ctgaagtgca gctgcagcag tctggcgctg aactggtccg gcctggcact    420

agcgtgaagc tgtcctgcaa ggtgtccggc gacaccatca ccttctacta catgcacttc    480

gtgaagcaga ggccaggaca gggcctggaa tggatcggca gaatcgaccc tgaggacgag    540

agcaccaagt acagcgagaa gttcaagaac aaggccaccc tgaccgccga caccagcagc    600

aacaccgcct acctgaagct gtctagcctg acctccgagg acaccgccac ctacttttgc    660

atctacggcg gctactactt cgactactgg ggccagggcg tgatggtcac cgtgtccagc    720
```

```
<210> SEQ ID NO 9
<211> LENGTH: 741
<212> TYPE: DNA
<213> ORGANISM: Artificial sequence
<220> FEATURE:
<223> OTHER INFORMATION: Synthetic oligonucleotide

<400> SEQUENCE: 9

ctgatccccg acatccagat gacccagacc acctccagcc tgagcgccag cctgggcgac     60

cgggtgacca tcagctgccg ggccagccag gacatcagca agtacctgaa ctggtatcag    120

cagaagcccg acggcaccgt caagctgctg atctaccaca ccagccggct gcacagcggc    180

gtgcccagcc ggtttagcgg cagcggctcc ggcaccgact acagcctgac catctccaac    240

ctggagcagg aggacatcgc cacctacttt tgccagcagg gcaacacact gccctacacc    300

tttggcggcg gaacaaagct ggagatcacc ggcagcacct ccggcagcgg caagcctggc    360

agcggcgagg gcagcaccaa gggcgaggtg aagctgcagg agagcggccc tggcctggtg    420

gcccccagcc agagcctgag cgtgacctgt accgtgtccg gcgtgtccct gcccgactac    480

ggcgtgtcct ggatccggca gccccctagg aagggcctgg agtggctggg cgtgatctgg    540

ggcagcgaga ccacctacta caacagcgcc ctgaagagcc ggctgaccat catcaaggac    600

aacagcaaga gccaggtgtt cctgaagatg aacagcctgc agaccgacga caccgccatc    660

tactactgtg ccaagcacta ctactacggc ggcagctacg ccatggacta ctggggccag    720

ggcaccagcg tgaccgtgtc c                                              741
```

```
<210> SEQ ID NO 10
<211> LENGTH: 723
<212> TYPE: DNA
<213> ORGANISM: Artificial sequence
<220> FEATURE:
<223> OTHER INFORMATION: Synthetic oligonucleotide

<400> SEQUENCE: 10

cagatcgtgc tgacccagag ccccgccatc atgagcgcca gccctggcga gaaggtgacc     60

atgacctgca gcgccagcag cagcgtgagc tacatgaact ggtatcagca gaagagcggc    120

accagcccca agcggtggat ctacgacacc agcaagctgg ccagcggcgt gcccgcccac    180

ttcaggggca gcggatctgg gacttcctac tctctgacca tcagcggcat ggaagccgag    240

gatgccgcta cttactactg ccagcagtgg agcagcaacc ccttcacctt cggctccggc    300

accaagctgg aaatcaaccg gggaggcggc ggttccggcg gaggtggctc tggcggtggc    360

ggaagtcagg tgcagctgca gcagagcgga gccgagctgg ccagacctgg cgcctccgtg    420
```

aagatgagct gcaaggccag cggctacacc ttcacccggt acaccatgca ctgggtgaag 480
cagagacccg gccagggcct ggaatggatc ggctacatca accccagccg gggctacacc 540
aactacaacc agaagttcaa ggacaaggcc accctgacca ccgacaagag cagcagcacc 600
gcctacatgc agctgtccag cctgacctcc gaggacagcg ccgtgtacta ctgcgcccgg 660
tactacgacg accactactg cctggactac tggggccagg gcaccacact gaccgtgagc 720
agc 723

<210> SEQ ID NO 11
<211> LENGTH: 735
<212> TYPE: DNA
<213> ORGANISM: Artificial sequence
<220> FEATURE:
<223> OTHER INFORMATION: Synthetic oligonucleotide

<400> SEQUENCE: 11
ctgatccccg acgtgcagat cacccagagc cccagctacc tggccgccag ccctggcgag 60
acaatcacca tcaactgccg ggccagcaag agcatcagca aggacctggc ctggtatcag 120
gaaaagcccg gcaagaccaa caagctgctg atctacagcg gcagcaccct gcagagcggc 180
atccccagca gattcagcgg cagcggctcc ggaaccgact tcaccctgac catcagcagc 240
ctggaacccg aggacttcgc catgtactac tgccagcagc acaacaagta cccctacacc 300
ttcggcggag gcaccaagct ggaaatcaag ggcagcacct ccggcagcgg caagcctggc 360
agcggcgagg gcagcaccaa gggccaggtg cagctgcagc agccaggcgc cgagctggtg 420
aaacctggcg cccctgtgaa gctgagctgc aaggccagcg gctacacctt caccaactac 480
tggatgaact ggatcaagca gaggcccggc agaggcctgg aatggatcgg cagaatcgac 540
cccagcgaca gcgagagcca ctacaaccag aagttcaagg acaaggccac actgaccgtg 600
gacaagagca gcaacaccgc ctacatccag ctgtcttctc tgaccagcga ggacagcgcc 660
gtgtactatt gcgccagata cgactacgac gacaccatgg actactgggg ccagggcacc 720
agcgtgaccg tgtct 735

<210> SEQ ID NO 12
<211> LENGTH: 810
<212> TYPE: DNA
<213> ORGANISM: Artificial sequence
<220> FEATURE:
<223> OTHER INFORMATION: Synthetic oligonucleotide

<400> SEQUENCE: 12
atggattttc aggtgcagat tttcagcttc ctgctaatca gtgcctcagt cataatgtct 60
agaatggccc aggtgcaact gcagcagtca ggggctgagc tggctagacc tggggcttca 120
gtgaagatgt cctgcaaggc ttctggctac acctttacta cctacacaat acactgggta 180
agacggaggc ctggacacga tctggaatgg attggataca ttaatcctag cagtggatgt 240
tctgactaca atcaaaactt caagggcaag accacattga ctgcagacaa gtcctccaac 300
acagcctaca tgcaactgaa cagcctgaca tctgaggact ctgcggtcta ttactgtgca 360
agaagagcgg actatggtaa ctacgaatat acctggtttg cttactgggg ccaagggacc 420
acggtcaccg tctcctcaag tggaggcggt tcaggtggag gtggctctgg cggtggcgga 480
tcggtcatcg agctcactca gtctccaaaa ttcatgtcca catcagtagg agacagggtc 540
aacgtcacct acaaggccag tcagaatgtg ggtactaatg tagcctggtt tcaacaaaaa 600

```
ccagggcaat ctcctaaagt tctgatttac tcggcatctt accgatacag tggagtccct    660

gatcgcttca caggcagtgg atctggaaca gatttcactc tcaccatcag caatgtgcag    720

tctgaagact tggcagagta tttctgtcag caatatcaca cctatcctct cacgttcgga    780

gggggcacca agctggaaat caaacggtcg                                     810


<210> SEQ ID NO 13
<211> LENGTH: 735
<212> TYPE: DNA
<213> ORGANISM: Artificial sequence
<220> FEATURE:
<223> OTHER INFORMATION: Synthetic oligonucleotide

<400> SEQUENCE: 13

caggtgcagc tggtgcagag cggcggcggc ctggtgcagc atggcggcag cctgcgcctg     60

agctgcgcgg cgagcggctt tacctttagc agctatgaaa tgaactgggt gcgccaggcg    120

ccgggcaaag gcctggaatg ggtgagcggc attagcggca gcggcggcag cacctattat    180

gcggatagcg tgaaaggccg ctttaccccc attagccgcg ataacagcaa aaacaccctg    240

tatctgcaga tgaaccgcct gcgcgcggaa gataccgcgg tgtattattg cgcgcgcgat    300

aacggctggg aactgaccga ttggtatttt gatctgtggg gccgcggcac catggtgacc    360

gtgagcagcg gcggcggcgg cagcggcggc ggcggcagcg gcggcggcgg cagcgatatt    420

cagatgaccc agagcccgag caccctgagc gcgagcattg gcgatcgcgt gaccattacc    480

tgccgcgcga gcgaaggcat ttatcattgg ctggcgtggt atcagcagaa accgggcaaa    540

gcgccgaaac tgctgattta taaagcgagc agcctggcga gcggcgcgcc gagccgcttt    600

agcggcagcg gcagcggcac cgattttacc ctgaccatta gcagcctgca gccggatgat    660

tttgcgacct attattgcca gcagtatagc aactatccgc tgacctttgg cggcggcacc    720

aaactggaaa ttaaa                                                     735


<210> SEQ ID NO 14
<211> LENGTH: 747
<212> TYPE: DNA
<213> ORGANISM: Artificial sequence
<220> FEATURE:
<223> OTHER INFORMATION: Synthetic oligonucleotide

<400> SEQUENCE: 14

gacgttgtga tgacccagac ccctctgagc ctgcctgtgt ccctgggaga tcaggccagc     60

atcagctgca gaagcagcca gagcctgctg aagaacaacg gcaacacctt cctgcactgg    120

tatctgcaga agtccggcca gtcccccaag ctgctgatct acaaggtgtc caaccggctg    180

agcggcgtgc ccgatagatt ttctggctct ggcagcggca cctacttcac cctgaagatc    240

agccgggtgg aagccgagga cctgggcgtg tacttctgta gccagagcac ccacatccct    300

tacaccttcg gcggaggcac caagctggaa ctgaagcggg gcagcacctc cggcagcggc    360

aagcctggca gcggcgaggg cagcaccaag ggcgaagtga agctggtgga aagcggcgga    420

ggcctggtgc tgcctggcga ttctctgaga ctgagctgcg ccaccagcga gttcaccttc    480

accgactact acatgacctg ggtgcgccag cccccccagaa aggctctgga atggctgggc   540

ttcatccgga accgggccaa cggctacacc accgagtaca accctagcgt gaagggccgg    600

ttcaccatca gccgggacaa cagccagagc atcctgtacc tgcagatgaa caccctgcgg    660

accgaggaca gcgccaccta ctactgtgct cgggtgtcca actgggcctt cgactattgg    720

ggccagggca ccaccctgac cgtgtct                                        747
```

<210> SEQ ID NO 15
<211> LENGTH: 759
<212> TYPE: DNA
<213> ORGANISM: Artificial sequence
<220> FEATURE:
<223> OTHER INFORMATION: Synthetic oligonucleotide

<400> SEQUENCE: 15
gacatcaaga tgacccagag ccccagctct atgtacgcca gcctgggcga gcgcgtgacc 60
atcacctgta aagccagccc cgacatcaac agctacctga gctggttcca gcagaagccc 120
ggcaagagcc ccaagaccct gatctaccgg gccaacagac tggtggatgg cgtgcccagc 180
agattcagcg gcggaggctc tggccaggac tacagcctga ccatcaactc cctggaatac 240
gaggacatgg gcatctacta ctgcctgcag tacgacgagt tcccctacac cttcggaggc 300
ggcaccaagc tggaaatgaa gggcagcaca agcggcagcg gcaagcctgg atctggcgag 360
ggaagcacca agggcgaagt gaagctggtg gaatctggcg gcggactcgt gaagcctggc 420
ggctctctga agctgtcttg tgccgccagc ggcttcacct tcagcagcta cgccatgagc 480
tgggtgcggc agatccccga gaagcggctg gaatgggtgg ccagcatcag cagaggcgga 540
accacctact accccgactc tgtgaagggc cggttcacca tcagccggga caacgtgcgg 600
aacatcctgt acctgcagat gagcagcctg cggagcgagg acaccgccat gtactactgt 660
ggcagatacg actacgacgg ctactatgcc atggattact ggggccaggg caccagcgtg 720
accgtgtcta gccagggaac ctccgtgaca gtgtccagc 759

<210> SEQ ID NO 16
<211> LENGTH: 759
<212> TYPE: DNA
<213> ORGANISM: Artificial sequence
<220> FEATURE:
<223> OTHER INFORMATION: Synthetic oligonucleotide

<400> SEQUENCE: 16
gaagtacatc tggttgagtc tggtggagac ttagtgaagc ctggagggtc cctgaaactc 60
tcctgtgcag cctctggatt cactttcagt cactatggca tgtcttgggt tcgccagact 120
ccagacaaga ggctggagtg ggtcgcaacc attggtagtc gtggtactta cacccactat 180
ccagacagtg tgaagggacg attcaccatc tccagagaca atgacaagaa cgccctgtac 240
ctgcaaatga acagtctgaa gtctgaagac acagccatgt attactgtgc aagaagaagt 300
gaattttatt actacggtaa tacctactat tactctgcta tggactactg gggccaaggc 360
accacggtca ccgtctcctc aggtggcggt ggcagcggcg gtggtgggtc cggtggcggc 420
ggatctgaca tcgtactcac acagtctcca gctagcctgg ctgtatctct aggacagagg 480
gccaccatct cctgcagagc cagcgaaagt gttgataatt atggctttag ttttatgaac 540
tggttccaac agaaaccagg acagccaccc aaactcctca tctatgctat atccaaccga 600
ggatccgggg tccctgccag gtttagtggc agtgggtctg ggacagactt cagcctcaac 660
atccatcctg tagaggagga tgatcctgca atgtatttct gtcagcaaac taaggaggtt 720
ccgtggacgt tcggagctgg caccaagctc gagatcaaa 759

<210> SEQ ID NO 17
<211> LENGTH: 543
<212> TYPE: DNA
<213> ORGANISM: Artificial sequence
<220> FEATURE:

<223> OTHER INFORMATION: Synthetic oligonucleotide

<400> SEQUENCE: 17

```
atggccatct ggcggagcaa cagcggcagc aacaccctgg aaaacggcta cttcctgagc     60

cggaacaaag agaaccacag ccagcccacc cagagcagcc tggaagatag cgtgaccccc    120

accaaggccg tgaaaaccac cggcgtgctg tccagcccct gccctcccaa ctggatcatc    180

tacgagaaga gctgctacct gttcagcatg agcctgaaca gctgggacgg cagcaagcgg    240

cagtgctggc agctgggcag caacctgctg aagatcgaca gcagcaacga gctgggcttc    300

atcgtgaagc aggtgtccag ccagcccgac aactccttct ggatcggcct gagcaggccc    360

cagaccgagg tgccctggct gtgggaggac ggctccacct tcagctccaa cctgttccag    420

atccggacca ccgccacaca ggaaaacccc agccccaact gcgtgtggat ccacgtgagc    480

gtgatctacg accagctgtg cagcgtgccc agctacagca tctgcgagaa gaaattcagc    540

atg                                                                  543
```

<210> SEQ ID NO 18
<211> LENGTH: 987
<212> TYPE: DNA
<213> ORGANISM: Artificial sequence
<220> FEATURE:
<223> OTHER INFORMATION: Synthetic oligonucleotide

<400> SEQUENCE: 18

```
atggattttc aggtgcagat tttcagcttc ctgctaatca gtgcctcagt cataatgtct     60

agacaattcc aagtgaagct ggaggagtct ggggctgagc ttgtgaggcc aggggccttg    120

gtcaagttgt cctgcaaaac ttctggcttc aacattaaag actacttttt acactgggtg    180

agacagaggc ctgaccaggg cctggagtgg attggatgga ttaatcctga taatggtaat    240

actgtttatg acccgaagct tcagggcacg gccagtttaa cagcagacac atcctccaac    300

acagtctact tgcagctcag cggcctgaca tctgaggaca ctgccgtcta tttctgtact    360

cggagggact atacttatga aaaggctgct ctggactact ggggtcaggg agcctcagtc    420

atcgtctcct cagccaaaac aacagcccca tcggtctatc cactggcccc tgtgtgtgga    480

gatacaactg gctcctcggt gactctagga tgcctggtca agagatctgg cggtggcggt    540

tctggtggcg gtggctccgg cggtggcggt tctggagctc gacattgtgc tcacacagac    600

tccaaatcca tgtccatgtc agtaggagag agggtcacct tgacctgcaa ggccagtgag    660

aatgtggtta cttatgtttc ctggtatcaa cagaaaccag agcagtctcc taaactgctg    720

atatacgggg catccaaccg gtacactggg gtccccgatc gcttcacagg cagtggatct    780

gcaacagatt tcactctgac catcagcagt gtgcaggctg aagaccttgc agattatcac    840

tgtggacagg gttacagcta tccgtacacg ttcggagggg ggaccaagct ggaaataaaa    900

cgggctgatg ctgcaccaac ttatccgcat caccatcatc atcatcatct gcagatatcc    960

agcacagtgg cggccgctcg agtctag                                        987
```

<210> SEQ ID NO 19
<211> LENGTH: 753
<212> TYPE: DNA
<213> ORGANISM: Artificial sequence
<220> FEATURE:
<223> OTHER INFORMATION: Synthetic oligonucleotide

<400> SEQUENCE: 19

```
ctgatcccca tggcccaggt gaagctgcag cagagcggcc ctgatctggt gaagcctggc     60
```

```
gccagcgtga agatcagctg caaggccagc ggctacagct tcaccggcta ctacatgcac    120

tgggtgaaac agagccacgg caagagcctg gaatggatcg gcagagtgaa ccccaatagc    180

ggcggcacca gctacaacca gaagttcaag gacaaggcca tcctgaccgt ggacaagagc    240

agcagcaccg cctacatgga actgcggagc ctgaccagcg aggacagcgc cgtgtactac    300

tgcgcccggt ccaagggcaa ctacttctac gccatggact actggggcca gggcaccacc    360

gtgaccgtgt ctagcagcgg cggaggaagc ggagggggag gatctggcgg aggcggcagc    420

gatatcgagc tgacccagag ccctagcagc ctggccgtgt cactgggcca gagagccacc    480

atcagctgca gagcctccga gagcgtggat agccacggca ccagcctgat gcactggtat    540

cagcagaagc ccggccagcc ccccaagttc ctgatctacc gggccagcaa cctggaaagc    600

ggcatccccg ccagattttc cggcagcggc agcagaaccg acttcaccct gaccatcaac    660

cccgtggaga cagacgacgt ggccatctac tactgccagc agagcaacga ggaccctccc    720

acctttggcg gaggcaccaa gctggaactg aag                                 753
```

```
<210> SEQ ID NO 20
<211> LENGTH: 732
<212> TYPE: DNA
<213> ORGANISM: Artificial sequence
<220> FEATURE:
<223> OTHER INFORMATION: Synthetic oligonucleotide

<400> SEQUENCE: 20

gaagtgcagc tggtggaatc tggcggcgga ctggtgcagc ctggcggatc tctgagactg     60

agctgtgccg ccagcggctt cgacttcagc cggtactgga tgagctgggt gcgccaggcc    120

cctggcaaag gcctggaatg gatcggcgag atcaaccccg acagcagcac catcaactac    180

gcccccagcc tgaaggacaa gttcatcatc agccgggaca acgccaagaa cagcctgtac    240

ctgcagatga actccctgcg ggccgaggac accgccgtgt actattgcgc cagacccgac    300

ggcaactact ggtacttcga cgtgtggggc cagggcaccc tcgtgacagt gtctggcagc    360

acaagcggct ctggcaagcc tggatctggc gagggctcta ccaagggcga catccagatg    420

acccagagcc ccagcagcct gtctgccagc gtgggcgaca gagtgaccat cacatgcaag    480

gccagccagg acgtgggaat cgccgtggcc tggtatcagc agaaacccgg caaggtgccc    540

aagctgctga tctactgggc cagcaccaga cacaccggcg tgcccgatag attttccggc    600

agcggctccg gcaccgactt caccctgaca atcagctccc tgcagcctga ggacgtggcc    660

acctactact gccagcagta cagcagctac ccctacacct tcggacaggg caccaaggtg    720

gaaatcaagc gg                                                        732
```

```
<210> SEQ ID NO 21
<211> LENGTH: 720
<212> TYPE: DNA
<213> ORGANISM: Artificial sequence
<220> FEATURE:
<223> OTHER INFORMATION: Synthetic oligonucleotide

<400> SEQUENCE: 21

caggtgcagc tgcagcagtc tggccccgag ctggaaaaac ctggcgcctc cgtgaagatc     60

agctgcaagg ccagcggcta cagcttcacc ggctacacca tgaactgggt caagcagagc    120

cacggcaaga gcctggaatg gatcggcctg atcacccct acaacggcgc cagcagctac     180

aaccagaagt tccggggcaa ggccaccctg accgtggaca agtctagcag caccgcctac    240
```

```
atggacctgc tgagcctgac cagcgaggac agcgccgtgt acttctgtgc cagaggcggc    300

tacgacggca gaggcttcga ttattggggc cagggcacca ccgtgacagt gtctagcgga    360

gtgggaggat ctggcggagg cggaagtggc ggagggggat ctgatatcga gctgacccag    420

agccccgcca tcatgtctgc tagccctggc gagaaagtga ccatgacctg cagcgccagc    480

tccagcgtgt cctacatgca ctggtatcag cagaagtccg gcaccagccc caagcggtgg    540

atctacgaca caagcaagct ggcctctggc gtgcccggca gattttctgg cagcggctcc    600

ggcaacagct actccctgac aatcagcagc gtggaagccg aggacgacgc cacctactac    660

tgccagcagt ggagcggcta ccccctgact tttggagccg gcaccaagct ggaaatcaag    720


<210> SEQ ID NO 22
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 22

agccaggaag agatgaccaa gaaccaggtg tccctgacct gcctcgtgaa gggcttctac     60


<210> SEQ ID NO 23
<211> LENGTH: 141
<212> TYPE: DNA
<213> ORGANISM: Artificial sequence
<220> FEATURE:
<223> OTHER INFORMATION: Synthetic oligonucleotide

<400> SEQUENCE: 23

aagcctacca caacccctgc ccccagacct cctacacccg cccctacaat tgccagccag     60

cctctgtctc tgaggcccga ggcttgtaga cctgctgctg gcggagccgt gcacaccaga    120

ggactggatt tcgcctgcga c                                              141


<210> SEQ ID NO 24
<211> LENGTH: 696
<212> TYPE: DNA
<213> ORGANISM: Artificial sequence
<220> FEATURE:
<223> OTHER INFORMATION: Synthetic oligonucleotide

<400> SEQUENCE: 24

agcgagagca agtacggccc tccctgcccc ccttgccctg cccccgagtt cctgggcgga     60

cccagcgtgt tcctgttccc ccccaagccc aaggacaccc tgatgatcag ccggaccccc    120

gaggtgacct gtgtggtggt ggacgtgtcc caggaggacc ccgaggtcca gttcaactgg    180

tacgtggacg gcgtggaggt gcacaacgcc aagaccaagc cccgggagga gcagttcaat    240

agcacctacc gggtggtgtc cgtgctgacc gtgctgcacc aggactggct gaacggcaag    300

gaatacaagt gtaaggtgtc caacaagggc ctgcccagca gcatcgagaa aaccatcagc    360

aaggccaagg gccagcctcg ggagccccag gtgtacaccc tgccccctag ccaagaggag    420

atgaccaaga atcaggtgtc cctgacctgc ctggtgaagg gcttctaccc cagcgacatc    480

gccgtggagt gggagagcaa cggccagccc gagaacaact acaagaccac cccccctgtg    540

ctggacagcg acggcagctt cttcctgtac agcaggctga ccgtggacaa gagccggtgg    600

caggagggca acgtctttag ctgctccgtg atgcacgagg ccctgcacaa ccactacacc    660

cagaagagcc tgtccctgag cctgggcaag atgttc                              696
```

<210> SEQ ID NO 25
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 25
agccaggaag agatgaccaa gaaccaggtg tccctgacct gcctcgtgaa gggcttctac 60

<210> SEQ ID NO 26
<211> LENGTH: 696
<212> TYPE: DNA
<213> ORGANISM: Artificial sequence
<220> FEATURE:
<223> OTHER INFORMATION: Synthetic oligonucleotide

<400> SEQUENCE: 26
agcgagagca agtacggccc tccctgcccc ccttgccctg cccccgagtt cctgggcgga 60
cccagcgtgt tcctgttccc ccccaagccc aaggacaccc tgatgatcag ccggaccccc 120
gaggtgacct gtgtggtggt ggacgtgtcc caggaggacc ccgaggtcca gttcaactgg 180
tacgtggacg gcgtggaggt gcacaacgcc aagaccaagc cccgggagga gcagttccag 240
agcacctacc gggtggtgtc cgtgctgacc gtgctgcacc aggactggct gaacggcaag 300
gaatacaagt gtaaggtgtc caacaagggc ctgcccagca gcatcgagaa aaccatcagc 360
aaggccaagg gccagcctcg ggagccccag gtgtacaccc tgccccctag ccaagaggag 420
atgaccaaga atcaggtgtc cctgacctgc ctggtgaagg gcttctaccc cagcgacatc 480
gccgtggagt gggagagcaa cggccagccc gagaacaact acaagaccac cccccctgtg 540
ctggacagcg acggcagctt cttcctgtac agcaggctga ccgtggacaa gagccggtgg 600
caggagggca acgtctttag ctgctccgtg atgcacgagg ccctgcacaa ccactacacc 660
cagaagagcc tgtccctgag cctgggcaag atgttc 696

<210> SEQ ID NO 27
<211> LENGTH: 696
<212> TYPE: DNA
<213> ORGANISM: Artificial sequence
<220> FEATURE:
<223> OTHER INFORMATION: Synthetic oligonucleotide

<400> SEQUENCE: 27
agcgagagca agtacggccc tccctgcccc ccttgccctg cccccgagtt cgaaggcgga 60
cccagcgtgt tcctgttccc ccccaagccc aaggacaccc tgatgatcag ccggaccccc 120
gaggtgacct gtgtggtggt ggacgtgtcc caggaggacc ccgaggtcca gttcaactgg 180
tacgtggacg gcgtggaggt gcacaacgcc aagaccaagc cccgggagga gcagttccag 240
agcacctacc gggtggtgtc cgtgctgacc gtgctgcacc aggactggct gaacggcaag 300
gaatacaagt gtaaggtgtc caacaagggc ctgcccagca gcatcgagaa aaccatcagc 360
aaggccaagg gccagcctcg ggagccccag gtgtacaccc tgccccctag ccaagaggag 420
atgaccaaga atcaggtgtc cctgacctgc ctggtgaagg gcttctaccc cagcgacatc 480
gccgtggagt gggagagcaa cggccagccc gagaacaact acaagaccac cccccctgtg 540
ctggacagcg acggcagctt cttcctgtac agcaggctga ccgtggacaa gagccggtgg 600
caggagggca acgtctttag ctgctccgtg atgcacgagg ccctgcacaa ccactacacc 660
cagaagagcc tgtccctgag cctgggcaag atgttc 696

<210> SEQ ID NO 28
<211> LENGTH: 711
<212> TYPE: DNA
<213> ORGANISM: Artificial sequence
<220> FEATURE:
<223> OTHER INFORMATION: Synthetic oligonucleotide

<400> SEQUENCE: 28

```
atggtgtcca agggcgagga actgatcaaa gaaaacatgc acatgaagct gtacatggaa     60

ggcaccgtga acaaccacca cttcaagtgc accagcgagg gagagggcaa gccctacgag    120

ggcacccaga ccatgcggat caaggtggtc gagggcggac ctctgccctt cgccttcgac    180

atcctggcca caagcttcat gtacggcagc aagaccttca tcaaccacac ccagggcatc    240

cccgatttct tcaagcagag cttccccgag ggcttcacct gggagagagt gaccacctac    300

gaggacggcg gcgtgctgac cgccacccag gacaccagcc tgcaggacgg ctgcctgatc    360

tacaacgtga agatccgggg cgtgaacttc cccagcaacg gccccgtgat gcagaagaaa    420

accctgggct gggaggccag caccgagatg ctgtaccctg ccgatggcgg cctggaaggc    480

agagccgaca tggccctgaa actggtcggc ggagggcacc tgatctgcaa cctgaaaacc    540

acctacagaa gcaagaagcc cgccaagaac ctgaagatgc ccggcgtgta ctacgtggac    600

cggcggctgg aaaggatcaa agaggccgac aaagaaacct acgtggagca gcacgaggtg    660

gccgtggccc ggtactgcga cctgccctcc aagctgggcc acaaactgaa c             711
```

<210> SEQ ID NO 29
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 29

```
atgatcgaga agtccttcgt gatcaccgac ccccggctgc ccgactaccc tatcatcttt     60

gccagcgacg gcttcctgga actgaccgag tacagccggg aagagatcat gggccggaac    120

gccagattcc tgcagggccc cgaaaccgat caggccaccg tgcagaagat ccgggacgcc    180

atcagggacc agcgggaaac cacagtgcag ctgatcaact acaccaagag cggcaagaag    240

ttctggaacc tgctgcatct gcagcccgtg cgggatagaa agggcggcct gcagtacttc    300

atcggcgtgc agctcgtggg cagcgaccac gtg                                 333
```

<210> SEQ ID NO 30
<211> LENGTH: 675
<212> TYPE: DNA
<213> ORGANISM: Artificial sequence
<220> FEATURE:
<223> OTHER INFORMATION: Synthetic oligonucleotide

<400> SEQUENCE: 30

```
atggccagca gcgaggacgt gatcaaagaa ttcatgcggt tcaaagtgcg gatggaaggc     60

agcgtgaacg gccacgagtt cgagattgag ggcgagggcg aaggcagacc ctacgaggga    120

acacagaccg ccaagctgaa agtgaccaag ggcggacccc tgcccttcgc ctgggatatc    180

ctgagccccc agttccagta cggcagcaag gtgtacgtga agcaccccgc cgacatcccc    240

gactacaaga agctgagctt ccccgagggc ttcaagtggg agagagtgat gaacttcgag    300

gacggcggcg tcgtgaccgt gacccaggat agctctctgc aggacggcag cttcatctac    360

aaagtgaagt ttatcggcgt gaacttcccc agcgacggcc ccgtgatgca gaaaaagacc    420
```

```
atgggctggg aggccagcac cgagagactg taccctagag atggcgtgct gaagggcgag    480

atccacaagg ccctgaagct gaaggatggc ggccactacc tggtggaatt caagagcatc    540

tacatggcca agaaacccgt gcagctgccc ggctactact acgtggacag caagctggac    600

atcaccagcc acaacgagga ctacaccatc gtggaacagt acgagcgggc cgagggccgg    660

caccatctgt ttctg                                                     675
```

<210> SEQ ID NO 31
<211> LENGTH: 717
<212> TYPE: DNA
<213> ORGANISM: Artificial sequence
<220> FEATURE:
<223> OTHER INFORMATION: Synthetic oligonucleotide

<400> SEQUENCE: 31

```
atggtgtcca agggcgagga actgttcacc ggcgtggtgc ccatcctggt ggaactggat     60

ggcgacgtga acggccacaa gttcagcgtg tccggcgagg gcgaaggcga cgccacatat    120

ggcaagctga ccctgaagct gatctgcacc accggcaagc tgcccgtgcc ttggcctacc    180

ctcgtgacca cactgggcta cggcctgcag tgcttcgcca gataccccga ccatatgaag    240

cagcacgact tcttcaagag cgccatgccc gagggctacg tgcaggaacg gaccatcttc    300

tttaaggacg acggcaacta caagaccagg gccgaagtga agttcgaggg cgacaccctc    360

gtgaaccgga tcgagctgaa gggcatcgac ttcaaagagg acggcaacat cctgggccac    420

aagctggagt acaactacaa cagccacaac gtgtacatca ccgccgacaa gcagaagaac    480

ggcatcaagg ccaacttcaa gatccggcac aacatcgagg acggcggcgt gcagctggcc    540

gatcactacc agcagaacac ccctatcggc gacggccctg tgctgctgcc cgacaatcac    600

tacctgagct accagagcgc cctgagcaag gaccccaacg agaagcggga ccacatggtg    660

ctgctggaat tcgtgaccgc cgctggcatc accctgggca tggacgagct gtacaag       717
```

<210> SEQ ID NO 32
<211> LENGTH: 717
<212> TYPE: DNA
<213> ORGANISM: Artificial sequence
<220> FEATURE:
<223> OTHER INFORMATION: Synthetic oligonucleotide

<400> SEQUENCE: 32

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaag       717
```

<210> SEQ ID NO 33
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 33
gccaagggcc agcctcggga gccccaggtg tacaccctgc cccctagcca agaggagatg 60
accaagaatc aggtgtccct gacctgcctg gtgaagggct tctaccccag cgacatcgcc 120
gtggagtggg agagcaacgg ccagcccgag aacaactaca agaccacccc ccctgtgctg 180
gacagcgacg gcagcttctt cctgtacagc aggctgaccg tggacaagag ccggtggcag 240
gagggcaacg tctttagctg ctccgtgatg cacgaggccc tgcacaacca ctacacccag 300
aagagcctgt ccctgagcct gggcaagatg ttctacccat acgatgttcc agattacgct 360
tac 363

<210> SEQ ID NO 34
<211> LENGTH: 708
<212> TYPE: DNA
<213> ORGANISM: Artificial sequence
<220> FEATURE:
<223> OTHER INFORMATION: Synthetic oligonucleotide

<400> SEQUENCE: 34
atggtgagca agggcgagga gaccacaatg ggcgtaatca agcccgacat gaagatcaag 60
ctgaagatgg agggcaacgt gaatggccac gccttcgtga tcgagggcga gggcgagggc 120
aagccctacg acggcaccaa caccatcaac ctggaggtga aggagggagc ccccctgccc 180
ttctcctacg acattctgac caccgcgttc gcctacggca acagggcctt caccaagtac 240
cccgacgaca tccccaacta cttcaagcag tccttccccg agggctactc ttgggagcgc 300
accatgacct tcgaggacaa gggcatcgtg aaggtgaagt ccgacatctc catggaggag 360
gactccttca tctacgagat acacctcaag ggcgagaact tccccccaa cggccccgtg 420 atgcagaaga agaccaccgg ctgggacgcc tccaccgaga ggatgtacgt gcgcgacggc 480
gtgctgaagg gcgacgtcaa gcacaagctg ctgctggagg gcggcggcca ccaccgcgtt 540
gacttcaaga ccatctacag ggccaagaag gcggtgaagc tgcccgacta tcactttgtg 600
gaccaccgca tcgagatcct gaaccacgac aaggactaca acaaggtgac cgtttacgag 660
agcgccgtgg cccgcaactc caccgacggc atggacgagc tgtacaag 708

<210> SEQ ID NO 35
<211> LENGTH: 423
<212> TYPE: DNA
<213> ORGANISM: Artificial sequence
<220> FEATURE:
<223> OTHER INFORMATION: Synthetic oligonucleotide

<400> SEQUENCE: 35
aagcctacca caacccctgc ccccagacct cctacacccg cccctacaat tgccagccag 60
cctctgtctc tgaggcccga ggcttgtaga cctgctgctg gcggagccgt gcacaccaga 120
ggactggatt tcgcctgcga caagcctacc acaacccctg cccccagacc tcctacaccc 180
gcccctacaa ttgccagcca gcctctgtct ctgaggcccg aggcttgtag acctgctgct 240
ggcggagccg tgcacaccag aggactggat ttcgcctgcg acagcagcgg cggcggcggc 300
agcggcggcg gcggcagcgg cggcggcggc agcgcgcagc tgaaaaaaaa actgcaggcg 360
ctgaaaaaaa aaaacgcgca gctgaaatgg aaactgcagg cgctgaaaaa aaaactggcg 420
cag 423

<210> SEQ ID NO 36
<211> LENGTH: 423
<212> TYPE: DNA
<213> ORGANISM: Artificial sequence
<220> FEATURE:
<223> OTHER INFORMATION: Synthetic oligonucleotide

<400> SEQUENCE: 36
aagcctacca caacccctgc ccccagacct cctacacccg cccctacaat tgccagccag 60
cctctgtctc tgaggcccga ggcttgtaga cctgctgctg gcggagccgt gcacaccaga 120
ggactggatt tcgcctgcga caagcctacc acaacccctg cccccagacc tcctacaccc 180
gcccctacaa ttgccagcca gcctctgtct ctgaggcccg aggcttgtag acctgctgct 240
ggcggagccg tgcacaccag aggactggat ttcgcctgcg acagcagcgg cggcggcggc 300
agcggcggcg gcggcagcgg cggcggcggc agcgcccagc tggaaaaaga gctgcaggcc 360
ctggaaaaag aaaacgctca gctggaatgg gaactgcagg ctctggaaaa agagctggcc 420
cag 423

<210> SEQ ID NO 37
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 37
tgggtgctgg tcgtggtggg tggcgtgctg gcctgctaca gcctgctggt gacagtggcc 60
ttcatcatc 69

<210> SEQ ID NO 38
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 38
attatctcat tcttcctggc cctgacctct accgccctgc tgtttctgct gttctttctg 60
accctgcggt tcagcgtggt g 81

<210> SEQ ID NO 39
<211> LENGTH: 84
<212> TYPE: DNA
<213> ORGANISM: Artificial sequence
<220> FEATURE:
<223> OTHER INFORMATION: Synthetic oligonucleotide

<400> SEQUENCE: 39
atctacatct gggcgccctt ggccgggact tgtggggtcc ttctcctgtc actggttatc 60
accctttact gcaaccacag gaac 84

<210> SEQ ID NO 40
<211> LENGTH: 63
<212> TYPE: DNA
<213> ORGANISM: Artificial sequence
<220> FEATURE:

<223> OTHER INFORMATION: Synthetic oligonucleotide

<400> SEQUENCE: 40
ctctgctacc tgctggatgg aatcctcttc atctatggtg tcattctcac tgccttgttc 60
ctg 63

<210> SEQ ID NO 41
<211> LENGTH: 144
<212> TYPE: DNA
<213> ORGANISM: Artificial sequence
<220> FEATURE:
<223> OTHER INFORMATION: Synthetic oligonucleotide

<400> SEQUENCE: 41
cagcggcgga agtacagaag caacaagggc gagagccccg tggaacctgc cgagccttgc 60
agatacagct gccccagaga ggaagagggc agcaccatcc caatccagga agattaccgg 120
aagcccgagc ccgcctgtag ccct 144

<210> SEQ ID NO 42
<211> LENGTH: 132
<212> TYPE: DNA
<213> ORGANISM: Artificial sequence
<220> FEATURE:
<223> OTHER INFORMATION: Synthetic oligonucleotide

<400> SEQUENCE: 42
ttttgggtga ggagcaagcg gagcagaggc ggccacagcg actacatgaa catgaccccc 60
cggaggcctg gccccacccg gaagcactac cagccctacg cccctcccag ggacttcgcc 120
gcctaccgga gc 132

<210> SEQ ID NO 43
<211> LENGTH: 132
<212> TYPE: DNA
<213> ORGANISM: Artificial sequence
<220> FEATURE:
<223> OTHER INFORMATION: Synthetic oligonucleotide

<400> SEQUENCE: 43
ttttgggtga ggagcaagcg gagcagaggc ggccacagcg acttcatgaa catgaccccc 60
cggaggcctg gccccacccg gaagcactac cagccctacg cccctcccag ggacttcgcc 120
gcctaccgga gc 132

<210> SEQ ID NO 44
<211> LENGTH: 108
<212> TYPE: DNA
<213> ORGANISM: Artificial sequence
<220> FEATURE:
<223> OTHER INFORMATION: Synthetic oligonucleotide

<400> SEQUENCE: 44
agggaccaga gactgcctcc cgatgcccac aaacctccag gcggcggaag cttcagaacc 60
cccatccagg aagaacaggc cgacgcccac agcaccctgg ccaagatt 108

<210> SEQ ID NO 45
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 45
aagcggggca gaaagaagct gctgtacatc ttcaagcagc ccttcatgcg gcccgtgcag 60
accacccagg aagaggacgg ctgctcctgc agattccccg aggaagaaga aggcggctgc 120
gagctg 126

<210> SEQ ID NO 46
<211> LENGTH: 102
<212> TYPE: DNA
<213> ORGANISM: Artificial sequence
<220> FEATURE:
<223> OTHER INFORMATION: Synthetic oligonucleotide

<400> SEQUENCE: 46
aagaaaaagt acagcagcag cgtgcacgac cccaacggcg agtacatgtt catgcgggcc 60
gtgaacaccg ccaagaagtc cagactgacc gacgtgaccc tg 102

<210> SEQ ID NO 47
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 47
cgggtgaagt tcagccggag cgccgacgcc cctgcctacc agcagggcca gaaccagctg 60
tacaacgagc tgaacctggg ccggagggag gagtacgacg tgctggacaa gcggagaggc 120
cgggaccctg agatgggcgg caagccccgg agaaagaacc ctcaggaggg cctgtataac 180
gaactgcaga aagacaagat ggccgaggcc tacagcgaga tcggcatgaa gggcgagcgg 240
cggaggggca agggccacga cggcctgtac cagggcctga gcaccgccac caaggatacc 300
tacgacgccc tgcacatgca ggccctgccc cccaga 336

<210> SEQ ID NO 48
<211> LENGTH: 759
<212> TYPE: DNA
<213> ORGANISM: Artificial sequence
<220> FEATURE:
<223> OTHER INFORMATION: Synthetic oligonucleotide

<400> SEQUENCE: 48
gatattcaga tgacccagag cccgagcagc ctgagcgcga gcgtgggcga tcgcgtgacc 60
attacctgcc gcagcagcca gaacattgtg catagcaacg gcaacaccta tctggattgg 120
tatcagcaga ccccgggcaa agcgccgaaa ctgctgattt ataaagtgag caaccgcttt 180
agcggcgtgc cgagccgctt tagcggcagc ggcagcggca ccgattttac ctttaccatt 240
agcagcctgc agccggaaga tattgcgacc tattattgct ttcagtatag ccatgtgccg 300
tggacctttg gccagggcac caaactgcag attaccggca gcacctccgg cagcggcaag 360
cctggcagcg gcgagggcag caccaagggc agccaggtgc agctgcagca gagcggcgcg 420
gaagtgaaaa aaccgggcag cagcgtgaaa gtgagctgca aagcgagcgg ctataccttt 480
accaactatt atatttattg ggtgcgccag gcgccgggcc agggcctgga atggattggc 540
ggcattaacc cgaccagcgg cggcagcaac tttaacgaaa aatttaaaac ccgcgtgacc 600
attaccgcgg atgaaagcag caccaccgcg tatatggaac tgagcagcct gcgcagcgaa 660
gataccgcgt tttatttttg cacccgccag ggcctgtggt ttgatagcga tggccgcggc 720
tttgattttt ggggccaggg caccaccgtg accgtgagc 759

<210> SEQ ID NO 49
<211> LENGTH: 732
<212> TYPE: DNA
<213> ORGANISM: Artificial sequence
<220> FEATURE:
<223> OTHER INFORMATION: Synthetic oligonucleotide

<400> SEQUENCE: 49
gatattctgc tgacccagag cccggtgatt ctgagcgtga gcccgggcga acgcgtgagc 60
tttagctgcc gcgcgagcca gagcattggc accaacattc attggtatca gcagcgcacc 120
aacggcagcc cgcgcctgct gattaaatat gcgagcgaaa gcattagcgg cattccgagc 180
cgctttagcg gcagcggcag cggcaccgat tttaccctga gcattaacag cgtggaaagc 240
gaagatattg cggattatta ttgccagcag aacaacaact ggccgaccac ctttggcgcg 300
ggcaccaaac tggaactgaa aggcagcacc tccggcagcg gcaagcctgg cagcggcgag 360
ggcagcacca agggcagcca ggtgcagctg aaacagagcg gcccgggcct ggtgcagccg 420
agccagagcc tgagcattac ctgcaccgtg agcggcttta gcctgaccaa ctatggcgtg 480
cattgggtgc gccagagccc gggcaaaggc ctggaatggc tgggcgtgat ttggagcggc 540
ggcaacaccg attataacac cccgtttacc agccgcctga gcattaacaa agataacagc 600
aaaagccagg tgttttttaa aatgaacagc ctgcagagca acgataccgc gatttattat 660
tgcgcgcgcg cgctgaccta ttatgattat gaatttgcgt attggggcca gggcaccctg 720
gtgaccgtga gc 732

<210> SEQ ID NO 50
<211> LENGTH: 726
<212> TYPE: DNA
<213> ORGANISM: Artificial sequence
<220> FEATURE:
<223> OTHER INFORMATION: Synthetic oligonucleotide

<400> SEQUENCE: 50
gaagtgcagc tgcagcagag cggcccggaa ctggaaaaac cgggcgcgag cgtgaaactg 60
agctgcaaag cgagcggcta tagctttacc ggctataaca tgaactgggt gaaacagagc 120
catggcaaaa gcctggaatg gattggccat attgatccgt attatggcga taccagctat 180
aaccagaaat ttcgcggcaa agcgaccctg accgtggata aaagcagcag caccgcgtat 240
atgcagctga aaagcctgac cagcgaagat agcgcggtgt attattgcgt gaaaggcggc 300
tattatggcc attggtattt tgatgtgtgg ggcgcgggca ccaccgtgac cgtgagcagc 360
ggcggaggcg gctctggcgg cggaggatca ggtggcggag gatccgatat tcagatgacc 420
cagagcccga gcagcctgag cgcgagcctg ggcgaacgcg tgagcctgac ctgccgcgcg 480
agccaggata ttggcagcag cctgaactgg ctgcagcagg gcccggatgg caccattaaa 540
cgcctgattt atgcgaccag cagcctggat agcggcgtgc cgaaacgctt tagcggcagc 600
cgcagcggca gcgattatag cctgaccatt agcagcctgg aaagcgaaga ttttgtggat 660
tattattgcc tgcagtatgt gagcagcccg ccgacctttg gcgcgggcac caaactggaa 720
ctgaaa 726

<210> SEQ ID NO 51
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 51

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110
```

<210> SEQ ID NO 52
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 52

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala
            100                 105
```

<210> SEQ ID NO 53
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 53

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80
```

```
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 54
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 54

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110


<210> SEQ ID NO 55
<211> LENGTH: 2034
<212> TYPE: DNA
<213> ORGANISM: Artificial sequence
<220> FEATURE:
<223> OTHER INFORMATION: Synthetic oligonucleotide

<400> SEQUENCE: 55

atgctgctgc tggtgaccag cctgctgctg tgtgagctgc cccaccccgc ctttctgctg      60

atccccgaca tccagatgac ccagaccacc tccagcctga gcgccagcct gggcgaccgg     120

gtgaccatca gctgccgggc cagccaggac atcagcaagt acctgaactg gtatcagcag     180

aagcccgacg gcaccgtcaa gctgctgatc taccacacca gccggctgca cagcggcgtg     240

cccagccggt ttagcggcag cggctccggc accgactaca gcctgaccat ctccaacctg     300

gagcaggagg acatcgccac ctacttttgc cagcagggca acacactgcc ctacaccttt     360

ggcggcggaa caaagctgga gatcaccggc agcacctccg gcagcggcaa gcctggcagc     420

ggcgagggca gcaccaaggg cgaggtgaag ctgcaggaga gcggccctgg cctggtggcc     480

cccagccaga gcctgagcgt gacctgtacc gtgtccggcg tgtccctgcc cgactacggc     540

gtgtcctgga tccggcagcc ccctaggaag ggcctggagt ggctgggcgt gatctggggc     600

agcgagacca cctactacaa cagcgccctg aagagccggc tgaccatcat caaggacaac     660

agcaagagcc aggtgttcct gaagatgaac agcctgcaga ccgacgacac cgccatctac     720

tactgtgcca agcactacta ctacggcggc agctacgcca tggactactg gggccagggc     780

accagcgtga ccgtgtccag cgagagcaag tacggccctc cctgcccccc ttgccctgcc     840

cccgagttcc tgggcggacc cagcgtgttc ctgttccccc ccaagcccaa ggacaccctg     900

atgatcagcc ggacccccga ggtgacctgt gtggtggtgg acgtgtccca ggaggacccc     960
```

```
gaggtccagt tcaactggta cgtggacggc gtggaggtgc acaacgccaa gaccaagccc   1020
cgggaggagc agttcaatag cacctaccgg gtggtgtccg tgctgaccgt gctgcaccag   1080
gactggctga acggcaagga atacaagtgt aaggtgtcca acaagggcct gcccagcagc   1140
atcgagaaaa ccatcagcaa ggccaagggc cagcctcggg agccccaggt gtacaccctg   1200
ccccctagcc aagaggagat gaccaagaat caggtgtccc tgacctgcct ggtgaagggc   1260
ttctacccca gcgacatcgc cgtggagtgg gagagcaacg gccagcccga gaacaactac   1320
aagaccaccc cccctgtgct ggacagcgac ggcagcttct tcctgtacag caggctgacc   1380
gtggacaaga gccggtggca ggagggcaac gtctttagct gctccgtgat gcacgaggcc   1440
ctgcacaacc actacaccca gaagagcctg tccctgagcc tgggcaagat gttctgggtg   1500
ctggtcgtgg tgggtggcgt gctggcctgc tacagcctgc tggtgacagt ggccttcatc   1560
atcttttggg tgaggagcaa gcggagcaga ggcggccaca gcgactacat gaacatgacc   1620
ccccggaggc ctggccccac ccggaagcac taccagccct acgcccctcc cagggacttc   1680
gccgcctacc ggagccgggt gaagttcagc cggagcgccg acgcccctgc ctaccagcag   1740
ggccagaacc agctgtacaa cgagctgaac ctgggccgga gggaggagta cgacgtgctg   1800
gacaagcgga gaggccggga ccctgagatg ggcggcaagc cccggagaaa gaaccctcag   1860
gagggcctgt ataacgaact gcagaaagac aagatggccg aggcctacag cgagatcggc   1920
atgaagggcg agcggcggag gggcaagggc cacgacggcc tgtaccaggg cctgagcacc   1980
gccaccaagg atacctacga cgccctgcac atgcaggccc tgccccccag atga         2034
```

<210> SEQ ID NO 56
<211> LENGTH: 2040
<212> TYPE: DNA
<213> ORGANISM: Artificial sequence
<220> FEATURE:
<223> OTHER INFORMATION: Synthetic oligonucleotide

<400> SEQUENCE: 56

```
atgctgctgc tggtgaccag cctgctgctg tgtgagctgc cccaccccgc ctttctgctg     60
atccccgaca tccagatgac ccagaccacc tccagcctga gcgccagcct gggcgaccgg    120
gtgaccatca gctgccgggc cagccaggac atcagcaagt acctgaactg gtatcagcag    180
aagcccgacg gcaccgtcaa gctgctgatc taccacacca gccggctgca cagcggcgtg    240
cccagccggt ttagcggcag cggctccggc accgactaca gcctgaccat ctccaacctg    300
gagcaggagg acatcgccac ctacttttgc cagcagggca acacactgcc ctacaccttt    360
ggcggcggaa caaagctgga gatcaccggc agcacctccg gcagcggcaa gcctggcagc    420
ggcgagggca gcaccaaggg cgaggtgaag ctgcaggaga gcggccctgg cctggtggcc    480
cccagccaga gcctgagcgt gacctgtacc gtgtccggcg tgtccctgcc cgactacggc    540
gtgtcctgga tccggcagcc ccctaggaag ggcctggagt ggctgggcgt gatctggggc    600
agcgagacca cctactacaa cagcgccctg aagagccggc tgaccatcat caaggacaac    660
agcaagagcc aggtgttcct gaagatgaac agcctgcaga ccgacgacac cgccatctac    720
tactgtgcca agcactacta ctacggcggc agctacgcca tggactactg gggccagggc    780
accagcgtga ccgtgtccag cgagagcaag tacggccctc cctgccccc ttgccctgcc     840
cccgagttcc tgggcggacc cagcgtgttc ctgttccccc ccaagcccaa ggacaccctg    900
atgatcagcc ggacccccga ggtgacctgt gtggtggtgg acgtgtccca ggaggacccc    960
```

```
gaggtccagt tcaactggta cgtggacggc gtggaggtgc acaacgccaa gaccaagccc   1020

cgggaggagc agttcaatag cacctaccgg gtggtgtccg tgctgaccgt gctgcaccag   1080

gactggctga acggcaagga atacaagtgt aaggtgtcca acaagggcct gcccagcagc   1140

atcgagaaaa ccatcagcaa ggccaagggc cagcctcggg agccccaggt gtacaccctg   1200

cccccctagcc aagaggagat gaccaagaat caggtgtccc tgacctgcct ggtgaagggc   1260

ttctacccca gcgacatcgc cgtggagtgg gagagcaacg gccagcccga gaacaactac   1320

aagaccaccc cccctgtgct ggacagcgac ggcagcttct tcctgtacag caggctgacc   1380

gtggacaaga gccggtggca ggagggcaac gtctttagct gctccgtgat gcacgaggcc   1440

ctgcacaacc actacaccca gaagagcctg tccctgagcc tgggcaagat gatctacatc   1500

tgggcccctc tggccggcac ctgtggcgtg ctgctgctga gcctggtcat caccctgtac   1560

tgcaaccacc ggaacaagag aggccggaag aaactgctgt acatcttcaa gcagcccttc   1620

atgcggcccg tgcagaccac ccaggaagag gacggctgca gctgccggtt ccccgaggaa   1680

gaggaaggcg gctgcgaact gcgggtgaag ttcagccgga gcgccgacgc ccctgcctac   1740

cagcagggcc agaaccagct gtacaacgag ctgaacctgg gccggaggga ggagtacgac   1800

gtgctggaca agcggagagg ccgggaccct gagatgggcg gcaagccccg gagaaagaac   1860

cctcaggagg gcctgtataa cgaactgcag aaagacaaga tggccgaggc ctacagcgag   1920

atcggcatga agggcgagcg gcggaggggc aagggccacg acggcctgta ccagggcctg   1980

agcaccgcca ccaaggatac ctacgacgcc ctgcacatgc aggccctgcc ccccagatga   2040
```

```
<210> SEQ ID NO 57
<211> LENGTH: 2037
<212> TYPE: DNA
<213> ORGANISM: Artificial sequence
<220> FEATURE:
<223> OTHER INFORMATION: Synthetic oligonucleotide

<400> SEQUENCE: 57

atgctgctgc tggtgaccag cctgctgctg tgtgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480

cccagccaga gcctgagcgt gacctgtacc gtgtccggcg tgtccctgcc cgactacggc    540

gtgtcctgga tccggcagcc ccctaggaag ggcctggagt ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgtgcca agcactacta ctacggcggc agctacgcca tggactactg gggccagggc    780

accagcgtga ccgtgtccag cgagagcaag tacggccctc cctgcccccc ttgccctgcc    840

cccgagttcc tgggcggacc cagcgtgttc ctgttccccc ccaagcccaa ggacaccctg    900

atgatcagcc ggacccccga ggtgacctgt gtggtggtgg acgtgtccca ggaggacccc    960

gaggtccagt tcaactggta cgtggacggc gtggaggtgc acaacgccaa gaccaagccc   1020
```

cgggaggagc agttcaatag cacctaccgg gtggtgtccg tgctgaccgt gctgcaccag 1080
gactggctga acggcaagga atacaagtgt aaggtgtcca acaagggcct gcccagcagc 1140
atcgagaaaa ccatcagcaa ggccaagggc cagcctcggg agccccaggt gtacaccctg 1200
ccccctagcc aagaggagat gaccaagaat caggtgtccc tgacctgcct ggtgaagggc 1260
ttctacccca gcgacatcgc cgtggagtgg gagagcaacg gccagcccga gaacaactac 1320
aagaccaccc cccctgtgct ggacagcgac ggcagcttct tcctgtacag caggctgacc 1380
gtggacaaga gccggtggca ggagggcaac gtctttagct gctccgtgat gcacgaggcc 1440
ctgcacaacc actacaccca gaagagcctg tccctgagcc tgggcaagat gatctacatc 1500
tgggcccctc tggccggcac ctgtggcgtg ctgctgctga gcctggtcat caccctgtac 1560
tgcaaccacc ggaataggag caagcggagc agaggcggcc acagcgacta catgaacatg 1620
accccccgga ggcctggccc cacccggaag cactaccagc cctacgcccc tcccagggac 1680
ttcgccgcct accggagccg ggtgaagttc agccggagcg ccgacgcccc tgcctaccag 1740
cagggccaga accagctgta caacgagctg aacctgggcc ggagggagga gtacgacgtg 1800
ctggacaagc ggagaggccg ggaccctgag atgggcggca agccccggag aaagaaccct 1860
caggagggcc tgtataacga actgcagaaa gacaagatgg ccgaggccta cagcgagatc 1920
ggcatgaagg gcgagcggcg gaggggcaag ggccacgacg gcctgtacca gggcctgagc 1980
accgccacca aggataccta cgacgccctg cacatgcagg ccctgccccc cagatga 2037

<210> SEQ ID NO 58
<211> LENGTH: 2037
<212> TYPE: DNA
<213> ORGANISM: Artificial sequence
<220> FEATURE:
<223> OTHER INFORMATION: Synthetic oligonucleotide

<400> SEQUENCE: 58
atgctgctgc tggtgaccag cctgctgctg tgtgagctgc cccaccccgc ctttctgctg 60
atccccgaca tccagatgac ccagaccacc tccagcctga gcgccagcct gggcgaccgg 120
gtgaccatca gctgccgggc cagccaggac atcagcaagt acctgaactg gtatcagcag 180
aagcccgacg gcaccgtcaa gctgctgatc taccacacca gccggctgca cagcggcgtg 240
cccagccggt ttagcggcag cggctccggc accgactaca gcctgaccat ctccaacctg 300
gagcaggagg acatcgccac ctacttttgc cagcagggca acacactgcc ctacaccttt 360
ggcggcggaa caaagctgga gatcaccggc agcacctccg gcagcggcaa gcctggcagc 420
ggcgagggca gcaccaaggg cgaggtgaag ctgcaggaga gcggccctgg cctggtggcc 480
cccagccaga gcctgagcgt gacctgtacc gtgtccggcg tgtccctgcc cgactacggc 540
gtgtcctgga tccggcagcc ccctaggaag ggcctggagt ggctgggcgt gatctggggc 600
agcgagacca cctactacaa cagcgccctg aagagccggc tgaccatcat caaggacaac 660
agcaagagcc aggtgttcct gaagatgaac agcctgcaga ccgacgacac cgccatctac 720
tactgtgcca agcactacta ctacggcggc agctacgcca tggactactg gggccagggc 780
accagcgtga ccgtgtccag cgagagcaag tacggccctc cctgcccccc ttgccctgcc 840
cccgagttcc tgggcggacc cagcgtgttc ctgttccccc ccaagcccaa ggacaccctg 900
atgatcagcc ggacccccga ggtgacctgt gtggtggtgg acgtgtccca ggaggacccc 960
gaggtccagt tcaactggta cgtggacggc gtggaggtgc acaacgccaa gaccaagccc 1020

```
cgggaggagc agttcaatag cacctaccgg gtggtgtccg tgctgaccgt gctgcaccag   1080

gactggctga acggcaagga atacaagtgt aaggtgtcca acaagggcct gcccagcagc   1140

atcgagaaaa ccatcagcaa ggccaagggc cagcctcggg agccccaggt gtacaccctg   1200

ccccctagcc aagaggagat gaccaagaat caggtgtccc tgacctgcct ggtgaagggc   1260

ttctacccca gcgacatcgc cgtggagtgg gagagcaacg gccagcccga gaacaactac   1320

aagaccaccc cccctgtgct ggacagcgac ggcagcttct tcctgtacag caggctgacc   1380

gtggacaaga gccggtggca ggagggcaac gtctttagct gctccgtgat gcacgaggcc   1440

ctgcacaacc actacaccca gaagagcctg tccctgagcc tgggcaagat gattatctca   1500

ttcttcctgg ccctgacctc taccgccctg ctgtttctgc tgttctttct gaccctgcgg   1560

ttcagcgtgg tcaagagagg ccggaagaaa ctgctgtaca tcttcaagca gcccttcatg   1620

cggcccgtgc agaccaccca ggaagaggac ggctgcagct gccggttccc cgaggaagag   1680

gaaggcggct gcgaactgcg ggtgaagttc agccggagcg ccgacgcccc tgcctaccag   1740

cagggccaga accagctgta caacgagctg aacctgggcc ggagggagga gtacgacgtg   1800

ctggacaagc ggagaggccg ggaccctgag atgggcggca agccccggag aaagaaccct   1860

caggagggcc tgtataacga actgcagaaa gacaagatgg ccgaggccta cagcgagatc   1920

ggcatgaagg gcgagcggcg gaggggcaag ggccacgacg gcctgtacca gggcctgagc   1980

accgccacca aggataccta cgacgccctg cacatgcagg ccctgccccc cagatga      2037
```

<210> SEQ ID NO 59
<211> LENGTH: 2160
<212> TYPE: DNA
<213> ORGANISM: Artificial sequence
<220> FEATURE:
<223> OTHER INFORMATION: Synthetic oligonucleotide

<400> SEQUENCE: 59

```
atgctgctgc tggtgaccag cctgctgctg tgtgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gagcaggagg acatcgccac ctacttttgc cagcagggca acacactgcc ctacaccttt    360

ggcggcggaa caaagctgga gatcaccggc agcacctccg gcagcggcaa gcctggcagc    420

ggcgagggca gcaccaaggg cgaggtgaag ctgcaggaga gcggccctgg cctggtggcc    480

cccagccaga gcctgagcgt gacctgtacc gtgtccggcg tgtccctgcc cgactacggc    540

gtgtcctgga tccggcagcc ccctaggaag ggcctggagt ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgtgcca agcactacta ctacggcggc agctacgcca tggactactg gggccagggc    780

accagcgtga ccgtgtccag cgagagcaag tacggccctc cctgcccccc ttgccctgcc    840

cccgagttcc tgggcggacc cagcgtgttc ctgttccccc ccaagcccaa ggacaccctg    900

atgatcagcc ggacccccga ggtgacctgt gtggtggtgg acgtgtccca ggaggacccc    960

gaggtccagt tcaactggta cgtggacggc gtggaggtgc acaacgccaa gaccaagccc   1020

cgggaggagc agttcaatag cacctaccgg gtggtgtccg tgctgaccgt gctgcaccag   1080
```

-continued

```
gactggctga acggcaagga atacaagtgt aaggtgtcca acaagggcct gcccagcagc   1140

atcgagaaaa ccatcagcaa ggccaagggc cagcctcggg agccccaggt gtacaccctg   1200

ccccctagcc aagaggagat gaccaagaat caggtgtccc tgacctgcct ggtgaagggc   1260

ttctacccca gcgacatcgc cgtggagtgg gagagcaacg gccagcccga gaacaactac   1320

aagaccaccc cccctgtgct ggacagcgac ggcagcttct tcctgtacag caggctgacc   1380

gtggacaaga gccggtggca ggagggcaac gtctttagct gctccgtgat gcacgaggcc   1440

ctgcacaacc actacaccca gaagagcctg tccctgagcc tgggcaagat gttctgggtg   1500

ctggtcgtgg tgggtggcgt gctggcctgc tacagcctgc tggtgacagt ggccttcatc   1560

atcttttggg tgaggagcaa gcggagcaga ggcggccaca gcgactacat gaacatgacc   1620

ccccggaggc ctggccccac ccggaagcac taccagccct acgcccctcc cagggacttc   1680

gccgcctacc ggagcaagag aggccggaag aaactgctgt acatcttcaa gcagcccttc   1740

atgcggcccg tgcagaccac ccaggaagag gacggctgca gctgccggtt ccccgaggaa   1800

gaggaaggcg gctgcgaact gcgggtgaag ttcagccgga gcgccgacgc ccctgcctac   1860

cagcagggcc agaaccagct gtacaacgag ctgaacctgg gccggaggga ggagtacgac   1920

gtgctggaca agcggagagg ccgggaccct gagatgggcg gcaagccccg gagaaagaac   1980

cctcaggagg gcctgtataa cgaactgcag aaagacaaga tggccgaggc ctacagcgag   2040

atcggcatga agggcgagcg gcggaggggc aagggccacg acggcctgta ccagggcctg   2100

agcaccgcca ccaaggatac ctacgacgcc ctgcacatgc aggccctgcc ccccagatga   2160
```